(12) United States Patent
Zawacki et al.

(10) Patent No.: US 9,387,304 B2
(45) Date of Patent: *Jul. 12, 2016

(54) MULTI-LUMEN CATHETER WITH SEPARATE DISTAL TIPS

(71) Applicant: C. R. Bard, Inc., Murray Hill, NJ (US)

(72) Inventors: John A. Zawacki, Shorewood, MN (US); Kelly B. Powers, North Salt Lake, UT (US); John G. Evans, South Jordan, UT (US); Guy Rome, Herriman, UT (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/328,541

(22) Filed: Jul. 10, 2014

(65) Prior Publication Data
US 2014/0330220 A1 Nov. 6, 2014

Related U.S. Application Data

(63) Continuation of application No. 11/874,447, filed on Oct. 18, 2007, now Pat. No. 8,808,227, which is a continuation of application No. 10/371,774, filed on Feb. 21, 2003, now Pat. No. 7,393,339.

(51) Int. Cl.
*A61M 25/00* (2006.01)
*A61M 1/36* (2006.01)

(52) U.S. Cl.
CPC ......... *A61M 25/0026* (2013.01); *A61M 1/3653* (2013.01); *A61M 1/3661* (2014.02); *A61M 25/007* (2013.01); *A61M 25/0009* (2013.01); *A61M 25/0074* (2013.01); *A61M 2025/0031* (2013.01); *A61M 2025/0037* (2013.01)

(58) Field of Classification Search
CPC ................. A61M 25/0026; A61M 2025/0034; A61M 2025/0037; A61M 25/0071
See application file for complete search history.

(56) References Cited

U.S. PATENT DOCUMENTS 701,075 A 5/1902 McCully
1,696,018 A 12/1928 Scheliberg
(Continued)

FOREIGN PATENT DOCUMENTS

BE 834211 2/1976
CA 1150122 7/1983
(Continued)

OTHER PUBLICATIONS

Haire, et al, Thrombotic Complications of Subclavian Apheresis catheters in Cancer Patients: Prevention With Heparin Infusion, Journal of Clinical Apheresis, 1990, vol. 5, pp. 188-191.
(Continued)

*Primary Examiner* — Imani Hayman
*Assistant Examiner* — Shefali Patel
(74) *Attorney, Agent, or Firm* — Rutan & Tucker, LLP

(57) ABSTRACT

A multi-lumen catheter including a generally cylindrical body enclosing a first and second lumen separated by a generally planar septum. A first and second tip section extend from a distal end of the body. The first and second tip section may each include a generally planar surface. The second tip section may include a first segment extending from the distal end of the body to a transition segment and a second segment extending from the transition segment to a distal end of the second tip section.

6 Claims, 24 Drawing Sheets

(56) References Cited

U.S. PATENT DOCUMENTS

| | | | |
|---|---|---|---|
| 1,856,811 A | 5/1932 | Inaki | |
| 2,024,982 A | 12/1935 | Scott | |
| 2,173,527 A | 9/1939 | Agayoff | |
| 2,286,462 A | 6/1942 | Chaffin | |
| 2,393,002 A | 1/1946 | Smith | |
| 2,748,769 A | 6/1956 | Huber | |
| 2,910,981 A | 11/1959 | Wilson et al. | |
| 3,144,868 A | 8/1964 | Jascalevich | |
| 3,176,690 A | 4/1965 | H'Doubler | |
| 3,256,885 A | 6/1966 | Higgins et al. | |
| 3,308,822 A | 3/1967 | De Luca | |
| 3,416,532 A | 12/1968 | Grossman | |
| 3,426,759 A | 2/1969 | Smith | |
| 3,460,255 A | 8/1969 | Hutson | |
| D217,795 S | 6/1970 | Spaven | |
| 3,612,038 A | 10/1971 | Halligan | |
| 3,736,939 A | 6/1973 | Taylor | |
| 3,805,794 A | 4/1974 | Schlesinger | |
| 3,812,851 A | 5/1974 | Rodriguez | |
| 3,848,604 A | 11/1974 | Sackner | |
| 3,890,977 A | 6/1975 | Wilson | |
| 3,929,126 A | 12/1975 | Corsaut | |
| 3,935,857 A | 2/1976 | Co | |
| 3,995,623 A | 12/1976 | Blake et al. | |
| 4,068,659 A | 1/1978 | Moorehead | |
| 4,072,146 A | 2/1978 | Howes | |
| 4,072,153 A | 2/1978 | Swartz | |
| 4,098,275 A | 7/1978 | Consalvo | |
| 4,114,625 A | 9/1978 | Onat | |
| 4,117,836 A | 10/1978 | Erikson | |
| 4,129,129 A | 12/1978 | Amrine | |
| 4,134,402 A | 1/1979 | Mahurkar | |
| 4,149,535 A | 4/1979 | Volder et al. | |
| 4,180,068 A | 12/1979 | Jacobsen et al. | |
| D254,444 S | 3/1980 | Levine | |
| 4,248,224 A | 2/1981 | Jones | |
| 4,276,880 A | 7/1981 | Malmin | |
| 4,292,976 A | 10/1981 | Banka | |
| 4,299,228 A | 11/1981 | Peters | |
| 4,300,550 A | 11/1981 | Gandi et al. | |
| 4,309,994 A | 1/1982 | Grunwald | |
| 4,327,722 A | 5/1982 | Groshong et al. | |
| 4,385,631 A | 5/1983 | Uthmann et al. | |
| 4,392,855 A | 7/1983 | Oreopoulos et al. | |
| 4,403,983 A | 9/1983 | Edelman et al. | |
| 4,405,313 A | 9/1983 | Sisley et al. | |
| 4,406,656 A | 9/1983 | Hattler et al. | |
| D272,651 S | 2/1984 | Mahurkar | |
| 4,431,426 A | 2/1984 | Groshong et al. | |
| 4,432,722 A | 2/1984 | Bohan, Jr. et al. | |
| 4,432,752 A | 2/1984 | Marlon | |
| 4,445,893 A | 5/1984 | Bodicky | |
| 4,451,252 A | 5/1984 | Martin et al. | |
| 4,453,928 A | 6/1984 | Steiger | |
| 4,465,482 A | 8/1984 | Tittel et al. | |
| 4,490,138 A | 12/1984 | Lipsky et al. | |
| 4,493,696 A | 1/1985 | Uldall et al. | |
| RE31,873 E | 4/1985 | Howes | |
| 4,531,933 A | 7/1985 | Norton et al. | |
| 4,543,087 A | 9/1985 | Sommercorn et al. | |
| 4,545,373 A | 10/1985 | Christoudias | |
| 4,549,879 A | 10/1985 | Groshong et al. | |
| 4,557,261 A | 12/1985 | Rugheimer et al. | |
| 4,568,329 A | 2/1986 | Mahurkar | |
| 4,568,338 A | 2/1986 | Todd | |
| 4,573,476 A | 3/1986 | Ruiz | |
| 4,581,012 A | 4/1986 | Brown et al. | |
| 4,583,968 A | 4/1986 | Mahurkar | |
| 4,583,986 A | 4/1986 | Lapidus | |
| 4,601,697 A | 7/1986 | Mammolenti et al. | |
| 4,619,643 A | 10/1986 | Bai | |
| 4,623,327 A | 11/1986 | Mahurkar | |
| 4,626,240 A | 12/1986 | Edelman et al. | |
| 4,642,101 A | 2/1987 | Krolikowski et al. | |
| 4,643,711 A | 2/1987 | Bates | |
| 4,666,426 A | 5/1987 | Aigner et al. | |
| 4,668,221 A | 5/1987 | Luther | |
| 4,670,009 A | 6/1987 | Bullock | |
| 4,675,004 A | 6/1987 | Hadford et al. | |
| 4,681,122 A | 7/1987 | Winters et al. | |
| 4,681,564 A | 7/1987 | Landreneau | |
| 4,681,570 A | 7/1987 | Dalton | |
| 4,682,978 A | 7/1987 | Martin et al. | |
| 4,687,471 A | 8/1987 | Twardowski et al. | |
| 4,692,141 A | 9/1987 | Mahurkar | |
| 4,694,838 A | 9/1987 | Wijayarthna et al. | |
| 4,701,159 A | 10/1987 | Brown et al. | |
| 4,702,917 A | 10/1987 | Schindler | |
| 4,713,171 A | 12/1987 | Polaschegg | |
| 4,717,379 A | 1/1988 | Ekholmer et al. | |
| 4,735,620 A | 4/1988 | Ruiz | |
| 4,737,141 A | 4/1988 | Spits et al. | |
| 4,737,152 A | 4/1988 | Alchas | |
| 4,738,667 A | 4/1988 | Galloway | |
| 4,748,808 A | 6/1988 | Hill | |
| 4,755,176 A | 7/1988 | Patel | |
| 4,769,016 A | 9/1988 | Labianca | |
| 4,770,652 A | 9/1988 | Mahurkar | |
| 4,772,268 A | 9/1988 | Bates | |
| 4,772,269 A | 9/1988 | Twardowski et al. | |
| 4,776,841 A | 10/1988 | Catalano | |
| 4,777,951 A | 10/1988 | Cribier et al. | |
| 4,784,638 A | 11/1988 | Ghajar et al. | |
| 4,790,809 A | 12/1988 | Kuntz | |
| 4,795,439 A | 1/1989 | Guest | |
| 4,801,297 A | 1/1989 | Mueller | |
| D300,060 S | 2/1989 | Molgaard-Nielsen | |
| 4,804,359 A | 2/1989 | Grunwald et al. | |
| 4,808,155 A | 2/1989 | Mahurkar | |
| 4,808,163 A | 2/1989 | Laub | |
| 4,809,710 A | 3/1989 | Williamson | |
| 4,820,265 A | 4/1989 | DeSatnick et al. | |
| 4,832,687 A | 5/1989 | Smith, III | |
| 4,834,709 A | 5/1989 | Banning et al. | |
| 4,842,582 A | 6/1989 | Mahurkar | |
| 4,842,592 A | 6/1989 | Caggiani et al. | |
| 4,846,814 A | 7/1989 | Ruiz | |
| 4,863,441 A | 9/1989 | Lindsay et al. | |
| 4,867,742 A | 9/1989 | Calderon | |
| 4,892,518 A | 1/1990 | Cupp et al. | |
| 4,894,057 A | 1/1990 | Howes | |
| 4,895,561 A | 1/1990 | Mahurkar | |
| 4,898,591 A | 2/1990 | Jang et al. | |
| 4,906,238 A | 3/1990 | Greenfeld et al. | |
| 4,925,452 A | 5/1990 | Melinyshyn et al. | |
| 4,927,418 A | 5/1990 | Dake et al. | |
| 4,935,004 A | 6/1990 | Cruz | |
| 4,935,010 A | 6/1990 | Cox et al. | |
| 4,935,044 A | 6/1990 | Schoenpflug et al. | |
| 4,936,826 A | 6/1990 | Amarasinghe | |
| 4,950,232 A | 8/1990 | Ruzicka et al. | |
| 4,950,259 A | 8/1990 | Geary et al. | |
| 4,951,665 A | 8/1990 | Schneider | |
| 4,961,729 A | 10/1990 | Vaillancourt | |
| 4,961,731 A | 10/1990 | Bodicky et al. | |
| 4,961,809 A | 10/1990 | Martin et al. | |
| 4,968,307 A | 11/1990 | Dake et al. | |
| 4,969,890 A | 11/1990 | Sugita et al. | |
| 4,981,477 A | 1/1991 | Schon et al. | |
| 4,985,014 A | 1/1991 | Orejola | |
| 4,990,138 A * | 2/1991 | Bacich | A61M 25/0119 604/103.05 |
| 4,994,027 A | 2/1991 | Farrell | |
| 4,995,865 A | 2/1991 | Gahara et al. | |
| 5,009,636 A | 4/1991 | Wortley et al. | |
| 5,015,230 A | 5/1991 | Martin et al. | |
| 5,016,640 A | 5/1991 | Ruiz | |
| 5,021,044 A | 6/1991 | Sharkawy | |
| 5,041,101 A | 8/1991 | Seder et al. | |
| 5,041,107 A | 8/1991 | Heil, Jr. | |
| 5,049,138 A | 9/1991 | Chevalier et al. | |
| 5,053,003 A | 10/1991 | Dadson et al. | |
| 5,053,004 A | 10/1991 | Markel et al. | |
| 5,053,023 A | 10/1991 | Martin | |

(56) References Cited

U.S. PATENT DOCUMENTS

| | | |
|---|---|---|
| 5,057,073 A | 10/1991 | Martin |
| 5,059,170 A | 10/1991 | Cameron |
| 5,069,673 A | 12/1991 | Shwab |
| 5,074,841 A | 12/1991 | Ademovic et al. |
| 5,084,013 A | 1/1992 | Takase et al. |
| 5,098,412 A | 3/1992 | Shiu et al. |
| 5,100,395 A | 3/1992 | Rosenberg et al. |
| 5,102,402 A | 4/1992 | Dror et al. |
| 5,106,368 A | 4/1992 | Uldall et al. |
| 5,106,376 A | 4/1992 | Mononen et al. |
| 5,111,829 A | 5/1992 | Alvarez de Toledo |
| 5,112,301 A | 5/1992 | Fenton, Jr. et al. |
| 5,114,423 A | 5/1992 | Kasprzyk et al. |
| 5,117,836 A | 6/1992 | Millar |
| 5,120,299 A | 6/1992 | Lombardi |
| 5,120,304 A | 6/1992 | Sasaki |
| 5,122,125 A | 6/1992 | Deuss et al. |
| 5,125,904 A | 6/1992 | Lee |
| 5,129,891 A | 7/1992 | Young |
| 5,135,599 A | 8/1992 | Martin et al. |
| 5,139,486 A | 8/1992 | Moss |
| 5,156,592 A | 10/1992 | Martin et al. |
| 5,163,928 A | 11/1992 | Hobbs et al. |
| 5,167,623 A | 12/1992 | Cianci et al. |
| 5,171,216 A | 12/1992 | Dasse et al. |
| 5,171,227 A | 12/1992 | Twardowski et al. |
| 5,178,616 A | 1/1993 | Uemiya et al. |
| 5,188,592 A | 2/1993 | Hakki |
| 5,188,593 A | 2/1993 | Martin |
| 5,190,520 A | 3/1993 | Fenton, Jr. et al. |
| 5,190,529 A | 3/1993 | McCrory et al. |
| 5,191,898 A | 3/1993 | Millar |
| 5,195,962 A | 3/1993 | Martin et al. |
| 5,197,951 A | 3/1993 | Mahurkar |
| 5,197,973 A | 3/1993 | Pang et al. |
| 5,197,976 A | 3/1993 | Herweck et al. |
| 5,201,723 A | 4/1993 | Quinn |
| 5,207,648 A | 5/1993 | Gross |
| 5,207,650 A | 5/1993 | Martin |
| 5,209,723 A | 5/1993 | Twardowski et al. |
| 5,209,725 A | 5/1993 | Roth |
| 5,209,742 A | 5/1993 | Venema et al. |
| 5,215,527 A | 6/1993 | Beck et al. |
| 5,221,255 A | 6/1993 | Mahurkar et al. |
| 5,221,256 A | 6/1993 | Mahurkar |
| 5,222,949 A | 6/1993 | Kaldany |
| 5,226,880 A | 7/1993 | Martin et al. |
| 5,234,438 A | 8/1993 | Semrad |
| 5,236,016 A | 8/1993 | Vogelsang et al. |
| 5,242,398 A | 9/1993 | Knoll et al. |
| 5,246,430 A | 9/1993 | MacFarlane |
| 5,250,034 A | 10/1993 | Appling et al. |
| 5,254,084 A | 10/1993 | Geary |
| 5,273,527 A | 12/1993 | Schatz et al. |
| 5,273,534 A | 12/1993 | Knoepfler |
| 5,279,596 A | 1/1994 | Castaneda et al. |
| 5,279,599 A | 1/1994 | Wilk |
| 5,306,240 A | 4/1994 | Berry |
| 5,312,337 A | 5/1994 | Flaherty et al. |
| 5,312,357 A | 5/1994 | Buijs et al. |
| 5,318,517 A | 6/1994 | Reiman |
| 5,322,519 A | 6/1994 | Ash |
| 5,324,274 A | 6/1994 | Martin |
| 5,330,432 A | 7/1994 | Yoon |
| 5,338,308 A | 8/1994 | Wilk |
| 5,342,295 A | 8/1994 | Imran |
| 5,342,386 A | 8/1994 | Trotta |
| 5,346,471 A | 9/1994 | Raulerson |
| 5,348,536 A | 9/1994 | Young et al. |
| 5,350,358 A | 9/1994 | Martin |
| 5,360,397 A | 11/1994 | Pinchuk |
| 5,360,407 A | 11/1994 | Leonard et al. |
| 5,364,344 A | 11/1994 | Beattie et al. |
| 5,374,245 A | 12/1994 | Mahurkar |
| 5,378,230 A | 1/1995 | Mahurkar |
| 5,380,276 A | 1/1995 | Miller et al. |
| 5,380,290 A | 1/1995 | Makower et al. |
| 5,382,238 A | 1/1995 | Abrahamson et al. |
| 5,389,087 A | 2/1995 | Miraki |
| 5,389,090 A | 2/1995 | Fischell et al. |
| 5,395,316 A | 3/1995 | Martin et al. |
| 5,399,168 A | 3/1995 | Wadsworth, Jr. et al. |
| 5,403,291 A | 4/1995 | Abrahamson |
| 5,405,320 A | 4/1995 | Twardowski et al. |
| 5,405,341 A | 4/1995 | Martin |
| 5,409,463 A | 4/1995 | Thomas et al. |
| 5,417,668 A | 5/1995 | Setzer et al. |
| 5,423,768 A | 6/1995 | Folden et al. |
| 5,431,661 A | 7/1995 | Koch |
| 5,451,026 A | 9/1995 | Smith |
| 5,451,206 A | 9/1995 | Young |
| 5,451,233 A | 9/1995 | Yock |
| 5,458,570 A | 10/1995 | May, Jr. |
| 5,458,582 A | 10/1995 | Nakao |
| 5,462,533 A | 10/1995 | Daugherty |
| 5,472,417 A | 12/1995 | Martin et al. |
| 5,472,432 A | 12/1995 | Martin |
| 5,476,453 A | 12/1995 | Mehta |
| 5,480,380 A | 1/1996 | Martin |
| 5,486,159 A | 1/1996 | Mahurkar |
| 5,489,278 A | 2/1996 | Abrahamson |
| 5,496,292 A | 3/1996 | Burnham |
| 5,496,872 A | 3/1996 | Constancis et al. |
| 5,505,710 A | 4/1996 | Dorsey, III |
| 5,507,723 A | 4/1996 | Keshaviah |
| 5,509,897 A | 4/1996 | Twardowski et al. |
| 5,509,900 A | 4/1996 | Kirkman |
| 5,509,902 A | 4/1996 | Raulerson |
| 5,542,925 A | 8/1996 | Orth |
| 5,545,373 A | 8/1996 | Maziasz et al. |
| 5,556,390 A | 9/1996 | Hicks |
| 5,556,930 A | 9/1996 | Brehm et al. |
| 5,558,635 A | 9/1996 | Cannon |
| 5,562,609 A | 10/1996 | Brumbach |
| 5,562,696 A | 10/1996 | Nobles et al. |
| 5,569,182 A | 10/1996 | Twardowski et al. |
| 5,569,195 A | 10/1996 | Saab |
| 5,571,093 A | 11/1996 | Cruz et al. |
| 5,584,803 A | 12/1996 | Stevens et al. |
| 5,599,304 A | 2/1997 | Shaari |
| 5,599,328 A | 2/1997 | Stevens |
| 5,607,462 A | 3/1997 | Imran |
| 5,624,392 A | 4/1997 | Saab |
| 5,624,413 A | 4/1997 | Markel et al. |
| 5,632,729 A | 5/1997 | Cai et al. |
| 5,637,102 A | 6/1997 | Tolkoff et al. |
| 5,642,270 A | 6/1997 | Green et al. |
| 5,655,867 A | 8/1997 | Gysi et al. |
| 5,662,606 A | 9/1997 | Cimino et al. |
| 5,665,067 A | 9/1997 | Linder et al. |
| 5,674,237 A | 10/1997 | Ott |
| 5,685,867 A | 11/1997 | Twardowski et al. |
| 5,686,867 A | 11/1997 | Sutardja et al. |
| 5,693,030 A | 12/1997 | Lee et al. |
| 5,695,457 A | 12/1997 | St. Goar et al. |
| 5,704,915 A | 1/1998 | Melsky et al. |
| 5,713,849 A | 2/1998 | Bosma et al. |
| 5,713,853 A | 2/1998 | Clark et al. |
| 5,717,216 A | 2/1998 | McCoy et al. |
| 5,718,678 A | 2/1998 | Fleming, III |
| 5,718,692 A | 2/1998 | Schon et al. |
| 5,720,735 A | 2/1998 | Dorros |
| 5,738,649 A | 4/1998 | Macoviak |
| 5,741,329 A | 4/1998 | Agrawal et al. |
| 5,743,873 A | 4/1998 | Cai et al. |
| 5,752,939 A | 5/1998 | Makoto |
| 5,769,796 A | 6/1998 | Palermo et al. |
| 5,772,643 A | 6/1998 | Howell et al. |
| 5,776,096 A | 7/1998 | Fields |
| 5,776,111 A | 7/1998 | Tesio |
| 5,785,686 A | 7/1998 | Runge |
| 5,792,094 A | 8/1998 | Stevens et al. |
| 5,792,123 A | 8/1998 | Ensminger |
| 5,797,869 A | 8/1998 | Martin et al. |

(56) References Cited

U.S. PATENT DOCUMENTS

| | | | |
|---|---|---|---|
| 5,800,384 A | 9/1998 | Russell et al. |
| 5,800,414 A | 9/1998 | Cazal et al. |
| 5,800,516 A | 9/1998 | Fine et al. |
| 5,807,311 A | 9/1998 | Palestrant |
| 5,807,318 A | 9/1998 | St. Goar et al. |
| 5,807,329 A | 9/1998 | Gelman |
| 5,809,897 A | 9/1998 | Powell et al. |
| 5,810,789 A | 9/1998 | Powers et al. |
| 5,814,016 A | 9/1998 | Valley et al. |
| 5,830,184 A | 11/1998 | Basta |
| 5,830,196 A | 11/1998 | Hicks |
| 5,833,671 A | 11/1998 | Macoviak et al. |
| 5,843,048 A | 12/1998 | Gross |
| 5,858,009 A | 1/1999 | Jonkman |
| 5,861,010 A | 1/1999 | Boussignac et al. |
| 5,868,717 A | 2/1999 | Prosl |
| 5,873,865 A | 2/1999 | Horzewski et al. |
| 5,876,366 A | 3/1999 | Dykstra et al. |
| 5,876,426 A | 3/1999 | Kume et al. |
| 5,882,347 A | 3/1999 | Mouris-Laan et al. |
| 5,891,111 A | 4/1999 | Ismael et al. |
| 5,904,670 A | 5/1999 | Schreiner |
| 5,911,715 A | 6/1999 | Berg et al. |
| 5,913,848 A | 6/1999 | Luther et al. |
| 5,916,208 A | 6/1999 | Luther et al. |
| 5,919,160 A | 7/1999 | Sanfilippo, II |
| 5,944,732 A | 8/1999 | Raulerson et al. |
| 5,947,937 A | 9/1999 | Urrutia et al. |
| 5,947,953 A | 9/1999 | Ash et al. |
| 5,957,879 A | 9/1999 | Roberts et al. |
| 5,957,893 A | 9/1999 | Luther et al. |
| 5,957,912 A | 9/1999 | Heitzmann |
| 5,961,486 A | 10/1999 | Twardowski et al. |
| 5,964,796 A | 10/1999 | Imran |
| 5,976,103 A | 11/1999 | Martin |
| 5,976,120 A | 11/1999 | Chow et al. |
| 5,980,551 A | 11/1999 | Summers et al. |
| 5,984,908 A | 11/1999 | Davis et al. |
| 5,989,206 A | 11/1999 | Prosl et al. |
| 5,989,213 A | 11/1999 | Maginot |
| 6,001,079 A | 12/1999 | Pourchez |
| 6,033,382 A | 3/2000 | Basta |
| 6,036,654 A | 3/2000 | Quinn et al. |
| 6,059,771 A | 5/2000 | Balbierz et al. |
| 6,074,374 A | 6/2000 | Fulton |
| 6,086,555 A | 7/2000 | Eliasen et al. |
| 6,090,096 A | 7/2000 | St. Goar et al. |
| 6,099,513 A | 8/2000 | Spehalski |
| 6,103,778 A | 8/2000 | Hyon et al. |
| 6,106,540 A | 8/2000 | White et al. |
| 6,113,572 A | 9/2000 | Gailey et al. |
| 6,117,117 A | 9/2000 | Mauch |
| 6,120,494 A | 9/2000 | Jonkman |
| 6,126,631 A | 10/2000 | Loggie |
| 6,143,013 A * | 11/2000 | Samson ............. A61M 25/005 604/264 |
| 6,146,354 A | 11/2000 | Beil |
| 6,146,373 A | 11/2000 | Cragg et al. |
| 6,152,909 A | 11/2000 | Bagaoisan et al. |
| 6,156,016 A | 12/2000 | Maginot |
| 6,161,547 A | 12/2000 | Barbut |
| 6,178,356 B1 | 1/2001 | Chastain et al. |
| 6,180,059 B1 | 1/2001 | Divino, Jr. et al. |
| 6,190,349 B1 * | 2/2001 | Ash ................... A61M 25/0021 138/115 |
| 6,190,371 B1 | 2/2001 | Maginot et al. |
| 6,193,685 B1 | 2/2001 | Goodin |
| 6,196,996 B1 | 3/2001 | Teirstein |
| 6,206,849 B1 | 3/2001 | Martin et al. |
| 6,210,365 B1 | 4/2001 | Afzal |
| 6,210,380 B1 | 4/2001 | Mauch |
| 6,217,527 B1 | 4/2001 | Selmon et al. |
| 6,224,622 B1 | 5/2001 | Kotzev |
| 6,238,406 B1 | 5/2001 | Ellis et al. |
| 6,264,627 B1 | 7/2001 | Liska et al. |
| 6,273,879 B1 | 8/2001 | Keith et al. |
| 6,280,413 B1 | 8/2001 | Clark et al. |
| 6,280,423 B1 | 8/2001 | Davey et al. |
| 6,287,326 B1 | 9/2001 | Pecor |
| 6,293,927 B1 | 9/2001 | McGuckin, Jr. |
| 6,293,958 B1 | 9/2001 | Berry et al. |
| 6,296,631 B2 | 10/2001 | Chow |
| 6,299,631 B1 | 10/2001 | Shalaby |
| 6,322,551 B1 | 11/2001 | Brugger |
| 6,328,730 B1 | 12/2001 | Harkrider, Jr. |
| 6,342,120 B1 | 1/2002 | Basta |
| 6,361,529 B1 | 3/2002 | Goodin et al. |
| 6,383,172 B1 | 5/2002 | Barbut |
| 6,394,141 B2 | 5/2002 | Wages et al. |
| 6,394,142 B1 | 5/2002 | Woelfel et al. |
| 6,409,700 B1 | 6/2002 | Siegel, Jr. et al. |
| 6,413,228 B1 | 7/2002 | Hung et al. |
| 6,428,513 B1 | 8/2002 | Abrahamson |
| 6,443,922 B1 | 9/2002 | Roberts et al. |
| 6,450,988 B1 | 9/2002 | Bradshaw |
| 6,453,185 B1 | 9/2002 | O'Keefe |
| 6,454,997 B1 | 9/2002 | Divino, Jr. et al. |
| 6,463,335 B1 | 10/2002 | Munch et al. |
| 6,468,287 B1 | 10/2002 | Baugh |
| 6,475,207 B1 | 11/2002 | Maginot et al. |
| 6,475,209 B1 | 11/2002 | Larson et al. |
| 6,478,789 B1 | 11/2002 | Spehalski et al. |
| 6,482,169 B1 | 11/2002 | Kuhle |
| 6,533,763 B1 | 3/2003 | Schneiter |
| 6,565,594 B1 | 5/2003 | Herweck et al. |
| 6,576,001 B2 | 6/2003 | Werneth et al. |
| 6,582,459 B1 | 6/2003 | Lau et al. |
| 6,585,705 B1 | 7/2003 | Maginot et al. |
| 6,592,565 B2 | 7/2003 | Twardowski |
| 6,595,966 B2 | 7/2003 | Davey et al. |
| 6,620,118 B1 | 9/2003 | Prosl et al. |
| 6,638,242 B2 | 10/2003 | Wilson et al. |
| 6,659,134 B2 | 12/2003 | Navis |
| 6,682,498 B2 | 1/2004 | Ross |
| 6,682,519 B1 | 1/2004 | Schon |
| 6,691,625 B2 | 2/2004 | Duncan |
| 6,695,832 B2 | 2/2004 | Schon et al. |
| 6,702,776 B2 | 3/2004 | Quinn |
| 6,712,797 B1 | 3/2004 | Southern, Jr. |
| 6,712,798 B2 | 3/2004 | Constantz |
| 6,719,717 B1 | 4/2004 | Johnson et al. |
| 6,719,749 B1 | 4/2004 | Schweikert et al. |
| 6,723,084 B1 | 4/2004 | Maginot et al. |
| 6,723,114 B2 | 4/2004 | Shalaby |
| 6,730,299 B1 | 5/2004 | Tayot et al. |
| 6,752,827 B2 | 6/2004 | Ross et al. |
| 6,755,851 B2 | 6/2004 | Noda et al. |
| 6,758,836 B2 | 7/2004 | Zawacki |
| 6,786,664 B2 | 9/2004 | Claramunt et al. |
| 6,786,884 B1 | 9/2004 | DeCant, Jr. et al. |
| 6,796,991 B2 | 9/2004 | Nardeo |
| 6,797,107 B2 | 9/2004 | Kotzey |
| 6,808,510 B1 | 10/2004 | DiFiore |
| 6,814,718 B2 | 11/2004 | McGuckin, Jr. et al. |
| 6,819,951 B2 | 11/2004 | Patel et al. |
| 6,821,287 B1 | 11/2004 | Jang |
| 6,824,554 B1 | 11/2004 | Jang |
| 6,835,452 B1 | 12/2004 | Hamerski |
| 6,837,864 B1 | 1/2005 | Bertolero et al. |
| 6,852,079 B2 | 2/2005 | Miyano |
| 6,852,097 B1 | 2/2005 | Fulton, III |
| 6,858,019 B2 | 2/2005 | McGuckin, Jr. et al. |
| 6,872,198 B1 | 3/2005 | Wilson et al. |
| 6,878,143 B2 | 4/2005 | Andersen |
| 6,881,211 B2 | 4/2005 | Schweikert et al. |
| 6,884,253 B1 | 4/2005 | McFarlane |
| 6,911,014 B2 | 6/2005 | Wentling et al. |
| 6,913,601 B2 | 7/2005 | St. Goar et al. |
| 6,916,313 B2 | 7/2005 | Cunningham |
| 6,921,396 B1 | 7/2005 | Wilson et al. |
| 6,921,411 B2 | 7/2005 | Yock |
| 6,934,142 B2 | 8/2005 | Grosse et al. |
| 6,966,886 B2 | 11/2005 | Appling |
| 6,969,381 B2 | 11/2005 | Voorhees |

(56) References Cited

U.S. PATENT DOCUMENTS

| | | |
|---|---|---|
| 6,979,318 B1 | 12/2005 | McDonald et al. |
| 6,991,625 B1 | 1/2006 | Gately et al. |
| D515,211 S | 2/2006 | Chesnin |
| 6,997,894 B2 | 2/2006 | Caresio |
| 7,008,395 B1 | 3/2006 | Loggie |
| 7,011,645 B2 | 3/2006 | McGuckin, Jr. et al. |
| 7,018,384 B2 | 3/2006 | Skakoon |
| 7,029,467 B2 | 4/2006 | Currier et al. |
| 7,066,914 B2 | 6/2006 | Andersen |
| 7,066,925 B2 | 6/2006 | Gately et al. |
| 7,074,213 B2 | 7/2006 | McGuckin, Jr. et al. |
| 7,077,829 B2 | 7/2006 | McGuckin, Jr. et al. |
| 7,087,053 B2 | 8/2006 | Vanney |
| 7,090,654 B2 | 8/2006 | Lotito et al. |
| 7,108,674 B2 | 9/2006 | Quinn |
| D530,420 S | 10/2006 | Chesnin |
| 7,128,734 B1 | 10/2006 | Wilson et al. |
| 7,130,700 B2 | 10/2006 | Gardeski et al. |
| 7,141,035 B2 | 11/2006 | Haggstrom |
| RE39,451 E | 12/2006 | Kuhle |
| 7,182,746 B2 | 2/2007 | Haarala et al. |
| 7,300,430 B2 | 11/2007 | Wilson et al. |
| 7,322,953 B2 | 1/2008 | Redinger |
| 7,347,852 B2 | 3/2008 | Hobbs et al. |
| 7,381,204 B2 | 6/2008 | Wilson et al. |
| 7,393,339 B2 | 7/2008 | Zawacki et al. |
| 7,422,571 B2 | 9/2008 | Schweikert et al. |
| 7,465,286 B2 | 12/2008 | Patterson et al. |
| 7,485,107 B2 | 2/2009 | DiFiore et al. |
| 7,569,029 B2 | 8/2009 | Clark |
| 7,575,563 B2 | 8/2009 | Appling |
| 7,651,482 B2 | 1/2010 | Harris |
| 7,686,823 B2 | 3/2010 | Pingleton et al. |
| 7,798,999 B2 | 9/2010 | Bailey et al. |
| 7,972,465 B2 | 7/2011 | Patterson et al. |
| 8,021,321 B2 | 9/2011 | Zawacki |
| 8,066,660 B2 | 11/2011 | Gregersen et al. |
| 8,092,415 B2 | 1/2012 | Moehle |
| 8,100,863 B2 | 1/2012 | Moehle et al. |
| 8,152,951 B2 | 4/2012 | Zawacki et al. |
| 8,206,371 B2 | 6/2012 | Nimkar et al. |
| 8,292,841 B2 | 10/2012 | Gregersen |
| 8,500,939 B2 | 8/2013 | Nimkar et al. |
| 8,540,661 B2 | 9/2013 | Gregersen |
| 8,597,275 B2 | 12/2013 | Nimkar et al. |
| 8,696,614 B2 | 4/2014 | Gregersen et al. |
| 8,808,227 B2 | 8/2014 | Zawacki et al. |
| 8,894,601 B2 | 11/2014 | Moehle et al. |
| 8,992,454 B2 | 3/2015 | Anand |
| 2001/0041857 A1 | 11/2001 | Sansoucy |
| 2001/0041873 A1 | 11/2001 | Dopper et al. |
| 2002/0013569 A1 | 1/2002 | Sterman et al. |
| 2002/0026156 A1* | 2/2002 | Quinn ............................ 604/264 |
| 2002/0086047 A1 | 7/2002 | Mueller et al. |
| 2002/0087108 A1 | 7/2002 | Maginot et al. |
| 2002/0087145 A1 | 7/2002 | Ehwald et al. |
| 2002/0091362 A1 | 7/2002 | Maginot et al. |
| 2002/0091430 A1 | 7/2002 | Dobak et al. |
| 2002/0099326 A1* | 7/2002 | Wilson ................. A61M 1/3653 604/43 |
| 2002/0099327 A1 | 7/2002 | Wilson et al. |
| 2002/0107506 A1 | 8/2002 | McGuckin et al. |
| 2002/0138031 A1 | 9/2002 | Ross |
| 2002/0169490 A1 | 11/2002 | Noda et al. |
| 2002/0177904 A1 | 11/2002 | Huxel et al. |
| 2003/0023198 A1 | 1/2003 | Twardowski |
| 2003/0088213 A1 | 5/2003 | Schweikert et al. |
| 2003/0093027 A1 | 5/2003 | McGuckin et al. |
| 2003/0097091 A1 | 5/2003 | Hobbs et al. |
| 2003/0144623 A1 | 7/2003 | Heath et al. |
| 2003/0149395 A1 | 8/2003 | Zawacki |
| 2003/0153898 A1 | 8/2003 | Schon et al. |
| 2003/0187411 A1 | 10/2003 | Constantz |
| 2003/0204179 A1 | 10/2003 | Davey et al. |
| 2004/0039350 A1 | 2/2004 | McKittrick |
| 2004/0054321 A1 | 3/2004 | Schon et al. |
| 2004/0059314 A1 | 3/2004 | Schon et al. |
| 2004/0064086 A1 | 4/2004 | Gottlieb et al. |
| 2004/0065333 A1 | 4/2004 | Wilson et al. |
| 2004/0075198 A1 | 4/2004 | Schweikert et al. |
| 2004/0087892 A1 | 5/2004 | Cunningham |
| 2004/0092863 A1 | 5/2004 | Raulerson et al. |
| 2004/0097863 A1 | 5/2004 | Appling |
| 2004/0097903 A1 | 5/2004 | Raulerson |
| 2004/0122418 A1 | 6/2004 | Voorhees |
| 2004/0147903 A1 | 7/2004 | Latini |
| 2004/0167463 A1 | 8/2004 | Zawacki et al. |
| 2004/0171997 A1 | 9/2004 | Wilson et al. |
| 2004/0172003 A1 | 9/2004 | Wilson et al. |
| 2004/0176739 A1 | 9/2004 | Stephens et al. |
| 2004/0193102 A1 | 9/2004 | Haggstrom |
| 2004/0210180 A1 | 10/2004 | Altman |
| 2004/0210187 A1 | 10/2004 | Zawacki |
| 2004/0210237 A1 | 10/2004 | Ross et al. |
| 2004/0220550 A1 | 11/2004 | Schryver |
| 2004/0230204 A1 | 11/2004 | Wortley et al. |
| 2004/0243095 A1 | 12/2004 | Nimkar et al. |
| 2004/0249337 A1 | 12/2004 | DiFiore |
| 2005/0003322 A1 | 1/2005 | Logan et al. |
| 2005/0004504 A1 | 1/2005 | Frye et al. |
| 2005/0013341 A1 | 1/2005 | Baghai |
| 2005/0025641 A1 | 2/2005 | Shibata et al. |
| 2005/0027282 A1 | 2/2005 | Schweikert et al. |
| 2005/0027289 A1 | 2/2005 | Castellano et al. |
| 2005/0033222 A1 | 2/2005 | Haggstrom et al. |
| 2005/0033264 A1 | 2/2005 | Redinger |
| 2005/0054989 A1 | 3/2005 | McGuckin et al. |
| 2005/0055012 A1 | 3/2005 | Trerotola |
| 2005/0059925 A1 | 3/2005 | Maginot et al. |
| 2005/0070842 A1 | 3/2005 | Lotito et al. |
| 2005/0080398 A1 | 4/2005 | Markel et al. |
| 2005/0085765 A1 | 4/2005 | Voorhees |
| 2005/0096585 A1 | 5/2005 | Schon et al. |
| 2005/0113904 A1 | 5/2005 | Shank et al. |
| 2005/0131341 A1 | 6/2005 | McGuckin et al. |
| 2005/0171469 A1 | 8/2005 | Cunningham |
| 2005/0187535 A1 | 8/2005 | Wilson et al. |
| 2005/0215977 A1 | 9/2005 | Uschold |
| 2005/0228339 A1 | 10/2005 | Clark |
| 2005/0245900 A1 | 11/2005 | Ash |
| 2005/0251190 A1 | 11/2005 | McFarlane |
| 2005/0256461 A1 | 11/2005 | DiFiore et al. |
| 2005/0261663 A1 | 11/2005 | Patterson et al. |
| 2005/0267400 A1 | 12/2005 | Haarala et al. |
| 2005/0277862 A1 | 12/2005 | Anand |
| 2005/0283111 A1 | 12/2005 | Maurice |
| 2005/0288623 A1 | 12/2005 | Hjalmarsson |
| 2005/0288706 A1 | 12/2005 | Widomski et al. |
| 2006/0004316 A1 | 1/2006 | Difiore et al. |
| 2006/0004325 A1 | 1/2006 | Hamatake et al. |
| 2006/0009783 A1 | 1/2006 | Rome et al. |
| 2006/0015072 A1 | 1/2006 | Raulerson |
| 2006/0015130 A1 | 1/2006 | Voorhees et al. |
| 2006/0030827 A1 | 2/2006 | Raulerson et al. |
| 2006/0047267 A1 | 3/2006 | Gately et al. |
| 2006/0047268 A1 | 3/2006 | Stephens |
| 2006/0058775 A1 | 3/2006 | Stevens et al. |
| 2006/0064072 A1 | 3/2006 | Gately et al. |
| 2006/0095062 A1 | 5/2006 | Stephens |
| 2006/0100572 A1 | 5/2006 | DiMatteo et al. |
| 2006/0161100 A1 | 7/2006 | Hamboly |
| 2006/0184142 A1 | 8/2006 | Schon et al. |
| 2006/0189922 A1 | 8/2006 | Amarasinghe et al. |
| 2006/0200111 A1 | 9/2006 | Moehle et al. |
| 2006/0206094 A1 | 9/2006 | Chesnin et al. |
| 2006/0251612 A1 | 11/2006 | Kotzev et al. |
| 2006/0253063 A1 | 11/2006 | Schweikert |
| 2006/0271012 A1 | 11/2006 | Canaud et al. |
| 2007/0005003 A1 | 1/2007 | Patterson et al. |
| 2007/0019181 A1 | 1/2007 | Sinclair et al. |
| 2007/0066964 A1 | 3/2007 | Atkins |
| 2007/0078478 A1 | 4/2007 | Atkins et al. |
| 2007/0106206 A1 | 5/2007 | Appling |
| 2007/0129704 A1 | 6/2007 | O'Mahony et al. |

(56) References Cited

U.S. PATENT DOCUMENTS

| | | |
|---|---|---|
| 2007/0167925 A1 | 7/2007 | Jacqmein |
| 2007/0191810 A1 | 8/2007 | Kennedy |
| 2007/0225661 A1 | 9/2007 | Ash et al. |
| 2007/0225682 A1 | 9/2007 | Ash et al. |
| 2007/0282274 A1 | 12/2007 | Chesnin |
| 2008/0021417 A1 | 1/2008 | Zawacki et al. |
| 2008/0039774 A1 | 2/2008 | Zawacki et al. |
| 2008/0065029 A1 | 3/2008 | Racz |
| 2008/0082079 A1 | 4/2008 | Braga et al. |
| 2008/0082080 A1 | 4/2008 | Braga |
| 2008/0097409 A1 | 4/2008 | Stephens |
| 2008/0172012 A1 | 7/2008 | Hiniduma-Lokuge et al. |
| 2008/0214980 A1 | 9/2008 | Anand |
| 2008/0214992 A1 | 9/2008 | Haarala et al. |
| 2009/0112153 A1 | 4/2009 | Gregersen et al. |
| 2009/0118661 A1 | 5/2009 | Moehle et al. |
| 2009/0118701 A1 | 5/2009 | Nimkar et al. |
| 2009/0118707 A1 | 5/2009 | Schweikert et al. |
| 2009/0118755 A1 | 5/2009 | Maliglowka et al. |
| 2009/0138034 A1 | 5/2009 | Maliglowka et al. |
| 2009/0157051 A1 | 6/2009 | Appling et al. |
| 2009/0187141 A1 | 7/2009 | Lareau et al. |
| 2009/0192435 A1 | 7/2009 | Gregersen |
| 2009/0204052 A1 | 8/2009 | Nimkar et al. |
| 2009/0204079 A1 | 8/2009 | Nimkar et al. |
| 2009/0204083 A1 | 8/2009 | O'Donnell et al. |
| 2009/0205189 A1 | 8/2009 | Nimkar et al. |
| 2009/0209940 A1 | 8/2009 | Nimkar et al. |
| 2009/0292248 A1 | 11/2009 | Schon et al. |
| 2010/0081986 A1 | 4/2010 | Matson et al. |
| 2010/0331780 A1 | 12/2010 | Bellisario et al. |
| 2011/0020418 A1 | 1/2011 | Bosley, Jr. et al. |
| 2012/0059304 A1 | 3/2012 | Gregersen et al. |
| 2012/0089070 A1 | 4/2012 | Moehle et al. |
| 2013/0018405 A1 | 1/2013 | Onishi et al. |
| 2013/0079752 A1 | 3/2013 | Gregersen |
| 2013/0253445 A1 | 9/2013 | Nimkar et al. |
| 2014/0025042 A1 | 1/2014 | Gregersen |
| 2014/0088510 A1 | 3/2014 | Nimkar et al. |
| 2014/0228742 A1 | 8/2014 | Gregersen et al. |
| 2014/0276472 A1 | 9/2014 | VanderStek et al. |
| 2014/0277052 A1 | 9/2014 | Haselby et al. |
| 2014/0336687 A1 | 11/2014 | Iwase et al. |
| 2015/0073336 A1 | 3/2015 | Moehle et al. |
| 2015/0088100 A1 | 3/2015 | Oborn et al. |

FOREIGN PATENT DOCUMENTS

| | | |
|---|---|---|
| CA | 2474351 A1 | 8/2003 |
| CN | 2788836 Y | 6/2006 |
| CN | 101918067 A | 12/2010 |
| CN | 201310073124 | 3/2013 |
| CN | 103170050 A | 6/2013 |
| CN | 101918066 B | 7/2013 |
| DE | 8815869 U1 | 2/1989 |
| DE | 9108132 U1 | 9/1991 |
| DE | 102005051211 A1 | 5/2007 |
| EP | 0030854 A2 | 6/1981 |
| EP | 0132344 A2 | 1/1985 |
| EP | 0301854 | 2/1989 |
| EP | 0332366 A2 | 9/1989 |
| EP | 0386408 A1 | 9/1990 |
| EP | 0453234 A1 | 10/1991 |
| EP | 0476796 A1 | 3/1992 |
| EP | 0495263 A1 | 7/1992 |
| EP | 0650740 A1 | 5/1995 |
| EP | 0711574 A1 | 5/1996 |
| EP | 1471966 A1 | 11/2004 |
| EP | 1599247 A2 | 11/2005 |
| GB | 1503469 | 3/1978 |
| JP | 56-136569 A | 10/1981 |
| JP | 8-510935 T | 11/1996 |
| JP | 2001137350 | 5/2001 |
| JP | 2008500081 A | 1/2008 |
| JP | 4827377 B2 | 11/2011 |
| SU | 459237 A1 | 2/1975 |
| WO | 9108132 A1 | 6/1991 |
| WO | 9316741 A1 | 9/1993 |
| WO | 9316752 A1 | 9/1993 |
| WO | 9709086 A1 | 3/1997 |
| WO | 9717102 | 5/1997 |
| WO | 9722374 A1 | 6/1997 |
| WO | 9737699 | 10/1997 |
| WO | 9904844 A1 | 2/1999 |
| WO | 0023137 A1 | 4/2000 |
| WO | 02058776 A2 | 8/2002 |
| WO | 02083223 A1 | 10/2002 |
| WO | 03030960 A2 | 4/2003 |
| WO | 03033049 A2 | 4/2003 |
| WO | 03066148 A1 | 8/2003 |
| WO | 04075962 A2 | 9/2004 |
| WO | 04096334 | 11/2004 |
| WO | 04112876 | 12/2004 |
| WO | 2005018712 A2 | 3/2005 |
| WO | 2005023336 A2 | 3/2005 |
| WO | 2005077449 | 8/2005 |
| WO | 2005084741 A1 | 9/2005 |
| WO | 2005118039 A1 | 12/2005 |
| WO | 2006034877 | 4/2006 |
| WO | 2009051967 A1 | 4/2009 |
| WO | 2009055332 A1 | 4/2009 |
| WO | 2009059220 A1 | 5/2009 |
| WO | 2015077560 A1 | 5/2015 |

OTHER PUBLICATIONS

Hull, et al., The Groshong Catheter: Initial Experience and Early Results of Imaging-guided Placementl, Radiology, 1992, vol. 185, pp. 803-807.

Ignotus, et al., Review of Radiological Insertion of Indwelling Central Venous Catheters, Minimally Invasive Therapy, 1992, 1:373-388.

Instructions for Use (Copyright Dated 1990) for Polycath Polyurethane Central Venous Catheter; believed to have been packaged with product and sold in the United States before Jan. 4, 2000 and with related marketing materials.

Instructions for Use (Copyright Dated 1992) for FloLock Single Lumen Bi-directional Valved Catheter; believed to have been packaged with product and sold in the United States before Jan. 2000.

Instructions for Use (not dated) for Infuse-a-Cath Polyurethance Central Venous Catheter; believed to have been packaged with product and sold in the United States before Jan. 2000.

Instructions for Use for Diatek Cannon Catheter Product First Sold in the United States in Sep. 2001.

Jones, et al., Efficacy of the Supraclavicular Route for Temporary Hemodialysis Access, Southern Medical Journal, 1992, vol. 85, No. 7, pp. 725-726.

JP 2010-532299 filed Apr. 30, 2010 Official Action dated Apr. 23, 2012.

JP App. No. 2003-565569 filed Feb. 7, 2003, Translated Decision of Refusal mailed Dec. 24, 2009.

JP App. No. 2003-565569 filed Feb. 7, 2003, Translated Official Action mailed May 28, 2009.

JP App. No. 2003-565569 filed Feb. 7, 2003, Translated Official Action mailed Nov. 7, 2008.

Kapoian et al. Dialysis as Treatment of End-Stage Renal Disease, Chapter 5: Dialysis Access and Recirculation, © 1999.

Kaupke, et al., Perforation of the Superior Vena Cava by a Subclavian Hemodialysis Catheter: early detection by angiography, The International Journal of Artificial Organs, 1992, vol. 15, No. 11, pp. 666-668.

Kelber, et al., Factors Affecting Delivery of High-Efficiency Dialysis Using Temporary Vascular Access, American Journal of Kidney Diseases, 1993, vol. 22, No. 1, pp. 24-29.

Lumsden, et al., Hemodialysis Access in the Pediatric Patient Population, The American Journal of Surgery, 1994, vol. 168, pp. 197.

Lund, "Percutaneous Translumbar Inferior Vena Cava Cannulation and other Alternative Vascular Access Techniques" in Venous Interventional Radiology with Clinical Perspectives, Savader et al, eds. pp. 251-61, Apr. 10, 2000.

(56) References Cited

OTHER PUBLICATIONS

Lund, et al., Percutaneous Translumbar Inferior Vena Cava Cannulation for Hemodialysis, American Journal of Kidney Diseases, 1995, vol. 25, No. 5, pp. 732-737.
Maki, D., Pathogenesis, Prevention, and Management of Infections Due to Intravascular Devices Used for Infusion Therapy, in Infections Associated with Indwelling Medical Devices, Bisno et al, eds, American Society for Microbiology, 1989, pp. 161-177.
Malviya et al., "Vascular Access in Gynecological Cancer Using the Groshong Right Atrial Catheter", Gynecological Oncology.
Mauro, et al., Radiologic Placement of Long-term Central Venous Catheters: A Review, JVIR, 1993, vol. 4, No. 1, pp. 127-137.
McGee, et al, Accurate placement of central venous catheters: A prospective, randomized, multicenter trial, Critical Care Medicine, 1993, vol. 21, No. 8, pp. 1118-1123.
Medcomp, For Access via the Internal Jugular Vein . . . The Medcomp TESIO Catheter is the Solution: The Short and Long Term Solution to Subclavian Venin Stenosis and Difficult Access Problems, Brochure, 4 pages, 1991.
Medcomp® Brochure, "Ash Split Cath™ XL", Dec. 2001, PN 2291.
Medcomp® Brochure, "Ash Split Cath™", Guidewire Weave Insertion Technique, Jan. 2002, PN 2296.
Medcomp® Brochure, "Ash Split Cath™", Jul. 2001, PN 2114.
Medcomp® Brochure, "Ash Split Cath™", Nov. 1997, PN 2050.
Medcomp® Brochure, "Ash Split Cath® II ", Aug. 2002, PN 2334.
Medcomp® Brochure, "Magna™ High Flow Catheter", Mar. 2002, PN 2321.
Moss et al, Use of Silicone Dual-Lumen Catheter with a Dacron Cuff as a Long Term Vascular Access for Hemodialysis Patients, Amer J Kidney Diseases, vol. XVI, No. 3, pp. 211-215, Sep. 1990.
Moss, et al., Use of a Silicone Catheter With a Dacron Cuff for Dialysis Short-Term Vascular Access, American Journal of Kidney Diseases, 1988, vol. XII, No. 6, pp. 492-498.
Myers, R.D. et al, New Double-lumen Polyethylene Cannula for Push-pull Perfusion of Brain Tissue in Vivo, Journal of Neuroscience Methods, pp. 205-218, vol. 12, 1985.
Northsea, C., Using Urokinase to Restore Patency in Double Lumen Catheters, ANNA Journal 1994, vol. 21, No. 5, pp. 261-273.
OriGen, OriGen Biomedical Dual Lumen Catheter, from <http://origen.neticatheter.html>, downloaded May 13, 2009, 4 pages (reprinted for submission on Jul. 21, 2011).
Parsa, et al., Establishment of Intravenous Lines for Long-term Intravenous Therapy and Monitoring, Surgical Clinics of N. Am. 1985, vol. 65, No. 4, pp. 835-865.
Parsa, et al., Vascular Access Techniques, Textbook of Critical Care, W.B. Saunders, Philadelphia, PA (1989), pp. 122-127.
Pasquale, et al., Groshong® Versus Hickman® Catheters, Surgery, Gynecology & Obstetrics, 1992, vol. 174, pp. 408-410.
Passaro, et al., Long-term Silastic Catheters and Chest Pain, Journal of Parenteral and Enteral Nutrition, 1994, vol. 18, No. 3, pp. 240-242.
Patel et al., "Sheathless Technique of Ash Split-Cath Insertion", 12 JVIR 376-78 (Mar. 2001).
Paulsen, et al., Use of Tissue Plasminogen Activator for Reopening of Clotted Dialysis Catheters, Nephron, 1993, vol. 64, pp. 468-470.
PCT/US2003/003751 filed Feb. 7, 2003 Preliminary Examination Report dated May 5, 2004.
PCT/US2003/003751 filed Feb. 7, 2003 Search Report dated Jul. 3, 2003.
PCT/US2004/005102 filed Feb. 19, 2004 Preliminary Report Patenability dated Aug. 29, 2005.
PCT/US2004/005102 filed Feb. 19, 2004 Search Report dated Dec. 27, 2004.
PCT/US2004/005102 filed Feb. 19, 2004 Written Opinion dated Aug. 21, 2005.
PCT/US2008/078551 filed Oct. 2, 2008 International Preliminary Report on Patentability dated Apr. 20, 2010.
PCT/US2008/078551 filed Oct. 2, 2008 Search Report dated Mar. 13, 2009.
PCT/US2008/078551 filed Oct. 2, 2008 Written Opinion dated Mar. 13, 2009.

PCT/US2008/078560 filed Oct. 2, 2008 Preliminary Report on Patentability dated Aug. 26, 2010.
Arrow Cannon II Plus Brochure, 2006.
*Arrow International, Inc. et al v. Spire Biomedical, Inc.*, U.S. Dist Ct Dist MA CA No. 06-CV-11564-DPW, Declaration of Dr. Karim Valji (Jul. 17, 2008).
*Arrow International, Inc. et al v. Spire Biomedical, Inc.*, U.S. Dist Ct Dist MA CA No. 06-CV-11564-DPW, Declaration of Kenneth Todd Cassidy (Jul. 16, 2008).
*Arrow International, Inc. et al v. Spire Biomedical, Inc.*, U.S. Dist Ct Dist MA CA No. 06-CV-11564-DPW, Declaration of Rebecca R. Eisenberg in Opposition to Defendant's Motion for Partial Summary Judgment of Invalidity (Jun. 8, 2009).
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity [Redacted Pursuant to Jun. 10, 2008 Order on Motion to Seal].
*Arrow International, Inc. et al v. Spire Biomedical, Inc.*, U.S. Dist Ct Dist MA CA No. 06-CV-11564-DPW, Memorandum of Law in Support of Defendant's Motion for Summary Judgment on Invalidity Exhibit a (Jul. 10, 2009).
*Arrow International, Inc. et al v. Spire Biomedical, Inc.*, U.S. Dist Ct Dist MA CA No. 06-CV-11564-DPW, Plaintiffs Memorandum in Opposition to Defendant's Motion for Summary Judgement on Non-Infringement (Jul. 17, 2008).
*Arrow International, Inc. et al. v. Spire Biomedical, Inc.*, U.S. Dist. Ct. Dist. MA CA No. 06-CV-11564-DPW, Defendant's Omnibus Statement of Material Facts in Support of its Motions for Summary Judgment (Jun. 10, 2008) [Redacted Pursuant to Jun. 10, 2008 Order on Motion to Seal].
Bander, et al., Central Venous Angioaccess for Hemodialysis and Its Complications, Seminars in Dialysis, 1992, vol. 5, No. 2, pp. 121-128.
Baranowski, L., Central Venous Access Devices, Journal of Intravenous Nursing, 1993, vol. 16, No. 3, pp. 167-194.
Bard Access Systems Hickman@, Leonard@, and Broviac® Central Venous Catheters (Long Term), Instructions for Use, 31 pages, 1999.
Bard Access Systems Hickman@, Leonard@, and Broviac® Central Venous Catheters, Nursing Procedural Manual, 52 pages, Jun. 1994.
Bard Davol® Hickman® Round Dual Lumen Catheters for Central Venous Access Informational Brochure, 4 pages, 1994.
Bard Hickman® Catheters Informational Brochure, 3 pages, 1994.
Believed to be an unpublished sketch of a conception by Dr. John Frusha; date of sketch believed to be Jun. 24, 1997.
Berkoben, et al., Maintenance of Permanent Hemodialysis Vascular Access Patency, ANNA Journal, 1995, vol. 22, No. 1, pp. 17-24.
Bolz, et al., Catheter Malfunction and Thrombus Formation on Double-Lumen Hemodialysis Catheters: An Intravascular Ultrasonographic Study, American Journal of Kidney Diseases, 1995, vol. 25, No. 4, pp. 597-602.
Bour, et al., Experience With the Double Lumen Silastic® Catheter for Hemoaccess, Surgery, Gynecology & Obstetrics, 1990, vol. 171, pp. 33-39.
Camp, "Care of the Groshong Catheter", Oncol Nurs Forum, vol. 15, No. 6, 1988.
Campbell, et al., Radiological Insertion of Long-term Venous Access Devices, Seminars in Interventional Radiology, 1994, vol. II, No. 4, pp. 366-375.
Canaud, B et al, Permenant Twin Catheter: A Vascular Access Option of Choice for Haemodialysis in Elderly Patients, pp. 82-88, vol. 17 No. 7, 1994.
Claim Construction Order of Federal District Court dated May 9, 2003 in *Thierry Pourchez and Bard Access Systems, Inc.* v. *Diatek, Inc. and Arrow International, Inc.* litigation (S.D. N.Y. 03 Civ.0972).
Claim Construction Order of Federal District Court dated Oct. 31, 2006 in *Arrow Int'l Inc.and Arrow Int'l. Investment Corp.* v. *Spire Biomedical, Inc.* litigation (D. Mass. Civil Action No. 06-CV-11564).
CN 200880121182.0 filed Oct. 20, 2008 First Office Action dated May 2, 2012.
CN 200880121183.5 filed Oct. 2, 2008 First Office Action dated Mar. 28, 2012.

(56) References Cited

OTHER PUBLICATIONS

CN 200880121183.5 filed Oct. 2, 2008 Second Office Action dated Aug. 17, 2012.
CN 200880121183.5 filed Oct. 2, 2008 Third Office Action dated Dec. 11, 2012.
CN 200880123095.9 filed Oct. 20, 2008 First Office Action dated Feb. 13, 2012.
CN 200880123095.9 filed Oct. 20, 2008 Second Office Action dated Dec. 18, 2012.
CN 200880123533.1 filed Jun. 30, 2008 First Office Action dated May 28, 2012.
CN 200880123533.1 filed Jun. 30, 2008 Notice of Grant dated Dec. 24, 2012.
Declaration of Gregory S. Haas (Plaintiff's Exhibit 88 in Haas Deposition), Mar. 13, 2003, *Thierry Pourchez and Bard Access Systems, Inc. v. Diatek, Inc. and Arrow International, Inc.*, Civil Action No. 03-CV-0972 (S.D.N.Y.).
Defendant's Exhibits DX78-DX114, *Thierry Pourchez and Bard Access Systems, Inc. v. Diatek, Inc. and Arrow International, Inc.*, Civil Action No. 03-CV-0972 (S.D.N.Y.), 2003.
Defendants' Reponses and Objections to Plaintiffs' Second Set of Interrogatories (Excerpt), *Thierry Pourchez and Bard Access Systems, Inc. v. Diatek, Inc. and Arrow International, Inc.*, Civil Action No. 03-CV-0972 (S.D.N.Y.) (Oct. 8, 2003).
Delmore et al., "Experience with the Groshong Long-Term Central Venous Catheter", Gynecologic Oncology 34, 216-218 (1989).
Dialysis Vascular Access, SchonXL® Temporary Dialysis (AngioDynamics Inc.) brochure, Nov. 1998.
Dialysis Vascular Access, Technological Innovations Improving Flow (AngioDynamics Inc.) Brochure, 4 pages, Nov. 1998.
Difiore, "Central Venous Dialysis Catheter Evaluatio in Swine", Journal of Vascular Access Devices, Fall 2000.
Donaldson, et al., Peripherally Inserted Central Venous Catheters: US-guided Vascular Access in Pediatric Patientsl, Radiology, 1995, vol. 197, pp. 542-544.
Dunea, et. al., A Survey of Permanent Double Lumen Catheters in Hemodialysis Patients. Asaio Transac. 1991; 37: M276-7.
Dupont et al, Long-term development of Permacath Quinton catheters used as a vascular access route for extra-renal detoxification; Néphrologie, vol. 15, pp. 105-110, 1994.
EP 04712925.9 filed Feb. 19, 2004 Office Action dated Nov. 7, 2008.
EP 08839196.6 filed Oct. 2, 2008 Examination Report dated Jan. 16, 2013.
EP 08839196.6 filed Oct. 2, 2008 Search Opinion dated Jul. 12, 2011.
EP 08839196.6 filed Oct. 2, 2008 Search Report dated Jul. 12, 2011.
EP 08872340.8 filed Oct. 2, 2008 Extended European Search Report and an Opinion dated Apr. 19, 2012.
Gallichio, et al., Placement of a Double Lumen Silastic Catheter for Hemodialysis Access Through the Cephalic Vein, Journal of the American College of Surgeons, 1994, vol. 179, pp. 171-172.
Gravenstein, et al., In Vitro Evaluation of Relative Perforating Potential of Central Venous Catheters: Comparison of Materials, Selected Models, Number of Lumens, and Angles of Incidence to Simulated Membrane, Journal of Clinical Monitoring, 1991, vol. 7, pp. 1-6.
Haindl, H., Technical complications of port-catheter systems, Reg. Cancer Treat, 1989, 2:238-242.
U.S. Appl. No. 10/842,586 filed May 10, 2004 Non-Final Office Action dated Jan. 7, 2008.
U.S. Appl. No. 10/842,586 filed May 10, 2004 Non-Final Office Action dated Jun. 16, 2009.
U.S. Appl. No. 10/842,586 filed May 10, 2004 Non-Final Office Action dated Nov. 13, 2008.
U.S. Appl. No. 10/842,586 filed May 10, 2004 Non-Final Office Action dated Nov. 23, 2009.
U.S. Appl. No. 10/874,298 filed Jun. 9, 2004 Advisory Action dated Feb. 19, 2009.
U.S. Appl. No. 10/874,298 filed Jun. 9, 2004 Final Office Action dated Jul. 15, 2008.
U.S. Appl. No. 10/874,298 filed Jun. 9, 2004 Final Office Action dated Jul. 7, 2010.
U.S. Appl. No. 10/874,298 filed Jun. 9, 2004 Final Office Action dated Mar. 18, 2014.
U.S. Appl. No. 10/874,298 filed Jun. 9, 2004 Non-Final Office Action dated Aug. 1, 2013.
U.S. Appl. No. 10/874,298 filed Jun. 9, 2004 Non-Final Office Action dated Aug. 18, 2011.
U.S. Appl. No. 10/874,298 filed Jun. 9, 2004 Non-Final Office Action dated Dec. 30, 2009.
U.S. Appl. No. 10/874,298 filed Jun. 9, 2004 Non-Final Office Action dated Feb. 2, 2011.
U.S. Appl. No. 10/874,298 filed Jun. 9, 2004 Non-Final Office Action dated Jul. 23, 2009.
U.S. Appl. No. 10/874,298 filed Jun. 9, 2004 Non-Final Office Action dated May 23, 2006.
U.S. Appl. No. 10/874,298 filed Jun. 9, 2004 Non-Final Office Action dated May 24, 2007.
U.S. Appl. No. 11/859,106 filed Sep. 21, 2007 Final Office Action dated Sep. 1, 2009.
U.S. Appl. No. 11/859,106 filed Sep. 21, 2007 Non-Final Office Action dated Feb. 5, 2009.
U.S. Appl. No. 11/859,106 filed Sep. 21, 2007 Non-Final Office Action dated Mar. 30, 2011.
U.S. Appl. No. 11/859,106 filed Sep. 21, 2007 Non-Final Office Action dated Jun. 25, 2008.
U.S. Appl. No. 11/874,447 filed Oct. 18, 2007 Decision on Appeal dated Dec. 26, 2012.
U.S. Appl. No. 11/874,447 filed Oct. 18, 2007 Examiners Answer dated Apr. 28, 2010.
U.S. Appl. No. 11/874,447 filed Oct. 18, 2007 Final Office Action dated Jul. 22, 2009.
U.S. Appl. No. 11/874,447 filed Oct. 18, 2007 Non-Final Office Action dated Jan. 6, 2009.
U.S. Appl. No. 11/874,447 filed Oct. 18, 2007 Non-Final Office Action dated Jul. 12, 2013.
U.S. Appl. No. 11/874,447 filed Oct. 18, 2007 Non-Final Office Action dated Jul. 9, 2008.
U.S. Appl. No. 11/874,447 filed Oct. 18, 2007 Notice of Allowance dated Apr. 18, 2014.
U.S. Appl. No. 12/048,871 filed Mar. 14, 2008 Examiner's Answer dated Feb. 9, 2012.
U.S. Appl. No. 12/048,871 filed Mar. 14, 2008 Final Office Action dated Jan. 20, 2011.
U.S. Appl. No. 12/048,871 filed Mar. 14, 2008 Non-Final Office Action dated Jan. 7, 2010.
U.S. Appl. No. 12/048,871 filed Mar. 14, 2008 Non-Final Office Action dated Jul. 7, 2010.
U.S. Appl. No. 12/048,871 filed Mar. 14, 2008 Non-Final Office Action dated May 12, 2009.
U.S. Appl. No. 12/244,514 filed Oct. 2, 2008 Final Office Action dated Jun. 19, 2012.
U.S. Appl. No. 12/244,514 filed Oct. 2, 2008 Non-Final Office Action dated Jan. 17, 2012.
U.S. Appl. No. 12/244,559 filed Oct. 2, 2008 Examiners Answer dated Mar. 27, 2013.
U.S. Appl. No. 12/244,559 filed Oct. 2, 2009 Final Office Action dated Jul. 3, 2012.
U.S. Appl. No. 12/244,559 filed Oct. 2, 2009 Non-Final Office Action dated Mar. 14, 2012.
U.S. Appl. No. 12/244,514 filed Oct. 2, 2008 Advisory Action dated Sep. 5, 2012.
U.S. Appl. No. 12/244,514 filed Oct. 2, 2008 Final Office Action dated Jul. 11, 2011.
U.S. Appl. No. 12/244,514 filed Oct. 2, 2008 Non-Final Office Action dated Jan. 19, 2011.
U.S. Appl. No. 12/244,544 filed Oct. 2, 2008 Final Office Action dated Jul. 11, 2011.
U.S. Appl. No. 12/244,544 filed Oct. 2, 2008 Non-Final Office Action dated Dec. 22, 2010.
U.S. Appl. No. 12/244,554 filed Oct. 2, 2008 Final Office Action dated Dec. 27, 2010.
U.S. Appl. No. 12/244,554 filed Oct. 2, 2008 Non-Final Office Action dated Jul. 6, 2010.

(56) References Cited

OTHER PUBLICATIONS

U.S. Appl. No. 12/253,870 filed Oct. 17, 2008 Non-Final Office Action dated Jan. 21, 2011.
U.S. Appl. No. 12/253,870 filed Oct. 17, 2008 Notice of Allowance dated Aug. 19, 2011.
U.S. Appl. No. 12/262,820 filed Oct. 31, 2008 Non-Final Office Action dated Feb. 18, 2011.
U.S. Appl. No. 12/262,820 filed Oct. 31, 2008 Notice of Allowance dated Sep. 28, 2011.
U.S. Appl. No. 12/263,141 filed Oct. 31, 2008 Advisory Action dated Aug. 17, 2011.
U.S. Appl. No. 12/263,141 filed Oct. 31, 2008 Final Office Action dated May 26, 2011.
U.S. Appl. No. 12/263,141 filed Oct. 31, 2008 Non-Final Office Action dated Jan. 5, 2011.
U.S. Appl. No. 12/414,467 filed Mar. 30, 2009 Final Office Action dated Feb. 7, 2012.
U.S. Appl. No. 12/414,467 filed Mar. 30, 2009 Notice of Allowance dated May 31, 2012.
U.S. Appl. No. 12/414,467 filed Mar. 30, 2009 Non-Final Office Action dated Aug. 11, 2011.
U.S. Appl. No. 13/294,941 filed Nov. 11, 2011 Non-Final Office Action dated May 31, 2013.
U.S. Appl. No. 13/294,941 filed Nov. 11, 2011 Notice of Allowance dated Nov. 27, 2013.
U.S. Appl. No. 13/445,713 filed Apr. 12, 2012 Advisory Action dated Aug. 8, 2013.
U.S. Appl. No. 13/445,713 filed Apr. 12, 2012 Final Office Action dated May 30, 2013.
U.S. Appl. No. 13/445,713 filed Apr. 12, 2012 Non-Final Office Action dated Jan. 2, 2013.
U.S. Appl. No. 13/445,713 filed Apr. 12, 2012 Notice of Allowance dated Oct. 18, 2013.
US Patent File History U.S. Pat. No. 5,403,291 (Abrahamson), issued Apr. 4, 1995.
US Patent File History U.S. Pat. No. 5,489,278 (Abrahamson), issued Feb. 6, 1996.
US Patent File History U.S. Pat. No. 5,685,867 (Twardowski et al.), issued Nov. 11, 1997.
Wechsler, et al., Thrombosis and Infection Caused by Thoracic Venous Catheters: Pathogenesis and Imagings Findings, AJR, 1993; 160:467-471.
Weitzel, et al, Successful Use of Indwelling Cuffed Femoral Vein Catheters in Ambulatory Hemodialysis Patients, American Journal of Kidney Diseases, 1993, vol. 22, No. 3, pp. 426-429.
PCT/US2008/078560 filed Oct. 2, 2008 Search Report dated Mar. 16, 2009.
PCT/US2008/078560 filed Oct. 2, 2008 Written Opinion dated Mar. 16, 2009.
PCT/US2008/078566 filed Oct. 2, 2008 International Preliminary Report on Patentability dated Apr. 20, 2010.
PCT/US2008/078566 filed Oct. 2, 2008 Search Report dated Mar. 19, 2009.
PCT/US2008/078566 filed Oct. 2, 2008 Written Opinion dated Mar. 19, 2009.
PCT/US2008/078571 filed Oct. 2, 2008 Preliminary Report on Patentability dated Aug. 26, 2010.
PCT/US2008/078571 filed Oct. 2, 2008 Search Report dated Mar. 20, 2009.
PCT/US2008/078571 filed Oct. 2, 2008 Written Opinion dated Mar. 20, 2009.
PCT/US2008/080463 filed Oct. 20, 2008 Preliminary Report on Patentability dated Apr. 27, 2010.
PCT/US2008/080463 filed Oct. 20, 2008 Search Report dated Mar. 16, 2009.
PCT/US2008/080463 filed Oct. 20, 2008 Written Opinion dated Apr. 16, 2009.
PCT/US2008/082106 filed Oct. 31, 2008 International Preliminary Report on Patentability dated May 4, 2010.
PCT/US2008/082106 filed Oct. 31, 2008 Search Report dated Jan. 12, 2009.
PCT/US2008/082106 filed Oct. 31, 2008 Written Opinion dated Jan. 12, 2009.
Picture of Device believed to be partial sample of a product believed to have been sold in the United States with Polycath and/or Infuse-a-Cath Instructions for Use, 1 page, 2011.
Quinton® Catheter Products (1993).
Raaf Dual Lumen Right Atrial Catheters Brochure—Quinton Instrument Co., 6 pages, 1993.
Raaf, et al., Open Insertion of Right Atrial Catheters Through the Jugular Veins, Surgery, Gynecology & Obstetrics, 1993, vol. 177, pp. 295-298.
Rawn, et al., The Hemodialysis Access, Chapter 9, pp. 9.1-9.11, available at <<http://msl1.mit.edu/ESD10/kidneys/HndbkPDF/Chap09.pdf>>, last accessed Jun. 4, 2012.
Schwab, et al., Prospective Evaluation of a Dacron Cuffed Hemodialysis Catheter for Prolonged Use, American Journal of Kidney Diseases, 1988, vol. XI, No. 2, pp. 166-169.
Schwab, et al., Vascular Access: Case Oriented Discussions of Selected Critical Issues: Hemodialysis Catheters for Permanent Use, 1999.
Shaffer, D., Catheter-Related Sepsis Complicating Long-Term Tunnelled Central Venous Dialysis Catheters: Management by Guidewire Exchange, American Journal of Kidney Diseases, 1995, vol. 25, No. 4, pp. 593-596.
Shaffer, D., Lessons From Vascular Access Procedures for Hemodialysis, Surgical Oncology Clinics of North America, 1995, vol. 4, No. 3, pp. 537-549.
Sioshansi, P., New Processes for Surface Treatment of Catheters, Artificial Organs, 1994, 18(4):266-271.
Swartz, et al., Successful Use of Cuffed Centrol Venous Hemodialysis Catheters Inserted Percutaneously, J. Am. Soc. Nephrol., 1994, 4:1719-1725.
Tal, Michael G, Comparison of Recirculation Percentage of the Palindrome Catheter and Standard Hemodialysis Catheters in a Swine Model, J Vasc Intery Radiol, pp. 1237-1240, vol. 16, No. 9, 2005.
Tesio, et al., Double Catheterization of the Internal Jugular Vein for Hemodialysis: Indications, Techniques, and Clinical Results, Artificial Organs, 1994, vol. 18, No. 4, pp. 301-304.
The Groshong™ Peripherally Inserted Central Venous Catheter Brochure—Cath-tech®, 4 pages, 1988.
Transcript of Videotaped Deposition of Gregory Haas (Excerpt), Sep. 23, 2003, *Thierry Pourchez and Bard Access Systems, Inc.* v. *Diatek, Inc. and Arrow International, Inc.*, Civil Action No. 03-Cv-0972 (S.D.N.Y.).
Transcript of Videotaped Deposition of Thierry Pourchez, vol. 1, Oct. 16, 2003, *Thierry Pourchez and Bard Access Systems, Inc.* v. *Diatek, Inc. and Arrow International, Inc.*, Civil Action No. 03-CV-0972 (S.D.N.Y.).
Transcript of Videotaped Deposition of Thierry Pourchez, vol. 2, Oct. 17, 2003, *Thierry Pourchez and Bard Access Systems, Inc.* v. *Diatek, Inc. and Arrow International, Inc.*, Civil Action No. 03-CV-0972 (S.D.N.Y.).
Treiman, et al., Chronic Venous Access in Patients with Cancer, Cancer, 1993, vol. 72, No. 3, pp. 760-765.
Twardowski et al. "Side Holes at the Tip of Chronic Hemodialysis Catehters are Harmful," The Journal of Vascular Access 2001; 2:8-16.
Twardowski et al., "Blood Recirculation in Intravenous Catheters for Hemodialysis" J. Am. Soc. Nephrol. 3:1978-81 (1993).
Tyco Healthcare, Mahurkar Dual Lumen Catheters, Informational Brochure, 2 pages, 2004.
Tyco Healthcare, Mahurkar QPlus High Flow Acute Care Catheter, Informational Brochure, 2 pages, 2004.
Tyco Healthcare, Tal Palindrome™ Dual Lumen Catheters Order Information, Features and Benefits, Frequently Asked Questions, printed from http://www.kendallvasculartherapy.com/VascularTherapy, 6 pages, on Mar. 1, 2007.
Uldall, P., Subclavian Cannulation Is No Longer Necessary or Justified in Patients with End-Stage Renal Failure, Seminars in Dialysis, 1994, vol. 7, No. 3, pp. 161-164.
U.S. Appl. No. 10/371,774 filed Feb. 21, 2003 Final Office Action dated Jan. 19, 2007.

(56) References Cited

OTHER PUBLICATIONS

U.S. Appl. No. 10/371,774 filed Feb. 21, 2003 Final Office Action dated Mar. 7, 2007.
U.S. Appl. No. 10/371,774 filed Feb. 21, 2003 Non-Final Office Action dated Jul. 17, 2006.
U.S. Appl. No. 10/371,774 filed Feb. 21, 2003 Notice of Allowance dated Jun. 1, 2007.
U.S. Appl. No. 10/445,731 filed May 27, 2003 Non-Final Office Action dated Apr. 13, 2007.
U.S. Appl. No. 10/445,731 filed May 27, 2003 Non-Final Office Action dated Dec. 12, 2008.
U.S. Appl. No. 10/445,731 filed May 27, 2003 Non-Final Office Action dated May 30, 2008.
U.S. Appl. No. 10/842,586 filed May 10, 2004 Advisory Action dated Oct. 9, 2008.
U.S. Appl. No. 10/842,586 filed May 10, 2004 Final Office Action dated Jul. 29, 2008.
U.S. Appl. No. 10/842,586 filed May 10, 2004 Final Office Action dated May 25, 2010.
CN 201310073124.8 filed Mar. 7, 2013 First Office Action dated May 5, 2014.
JP 2010-532299 filed Apr. 30, 2010 Final Notice of Reason for Rejection dated Feb. 8, 2013.
PCT/US2014/066811 filed Nov. 21, 2014 International Search Report and Written Opinion dated Apr. 15, 2015.
Septum, Wikipedia, The Free Encyclopedia, hhtp://en.wikipedia.org/wiki/Septum (last visited Dec. 18, 2012) (defining "septum" as "a wall, dividing a cavity or structure into smaller ones").
Taber's Cyclopedic Medical Dictionary 1662 (16th ed. 1989) (defining "septum" as a "wall dividing two cavities").
U.S. Appl. No. 10/874,298 filed Jun. 9, 2004 Non-Final Office Action dated Jul. 9, 2014.
U.S. Appl. No. 12/048,871 filed Mar. 14, 2008 Decision on Appeal dated Feb. 2, 2015.
U.S. Appl. No. 13/329,156 filed Dec. 16, 2011 Non-Final Office Action dated May 16, 2014.
U.S. Appl. No. 13/897,292 filed May 17, 2013 Final Office Action dated Apr. 9, 2015.
U.S. Appl. No. 13/897,292 filed May 17, 2013 Non-Final Office Action dated Nov. 20, 2014.
U.S. Appl. No. 14/032,858 filed Sep. 20, 2013 Final Office Action dated Mar. 31, 2015.
U.S. Appl. No. 14/032,858 filed Sep. 20, 2013 Non-Final Office Action dated Nov. 4, 2014.
U.S. Appl. No. 14/252,567 filed Apr. 14, 2014 Non-Final Office Action dated Mar. 31, 2015.
U.S. Appl. No. 14/094,534, filed Dec. 2, 2013 Non-Final Office Action dated Feb. 24, 2016.

* cited by examiner

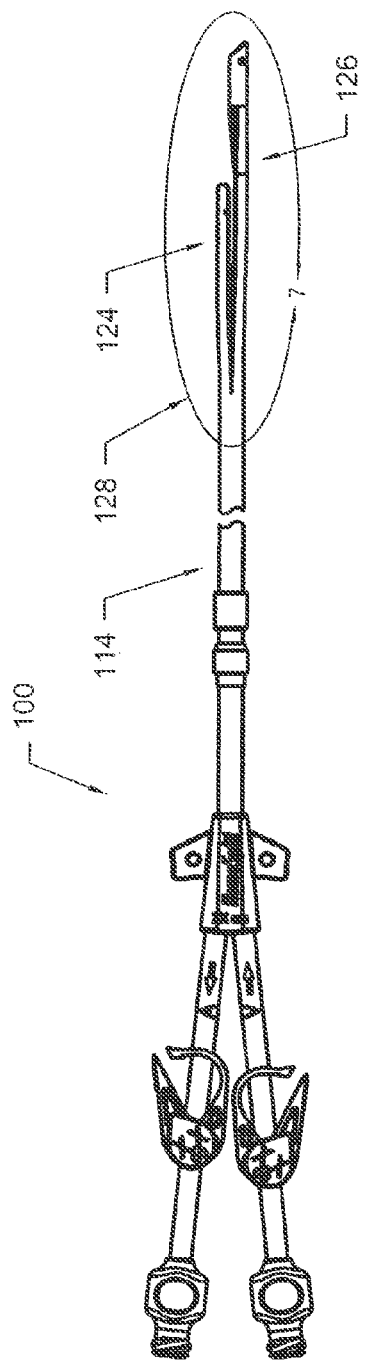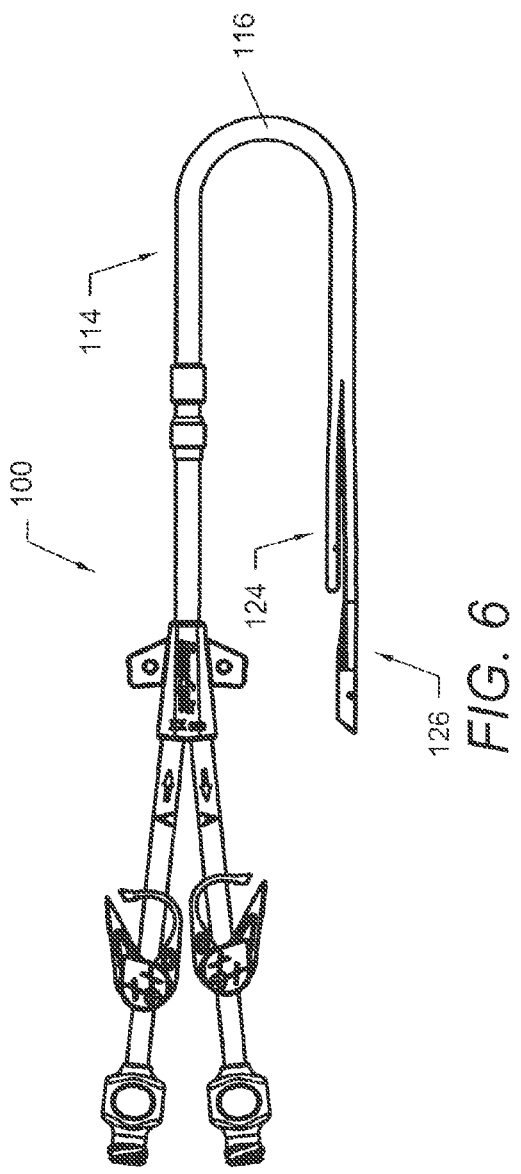

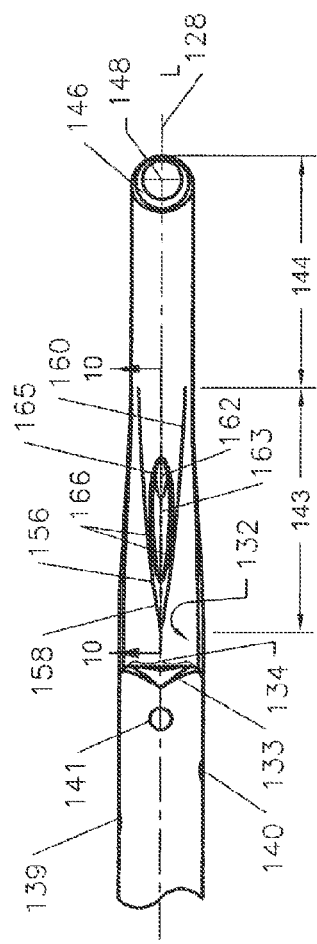
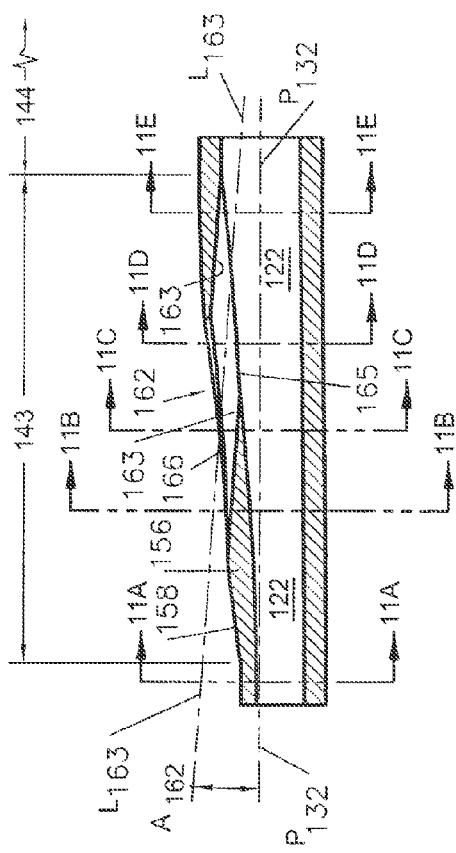
FIG. 9
FIG. 10

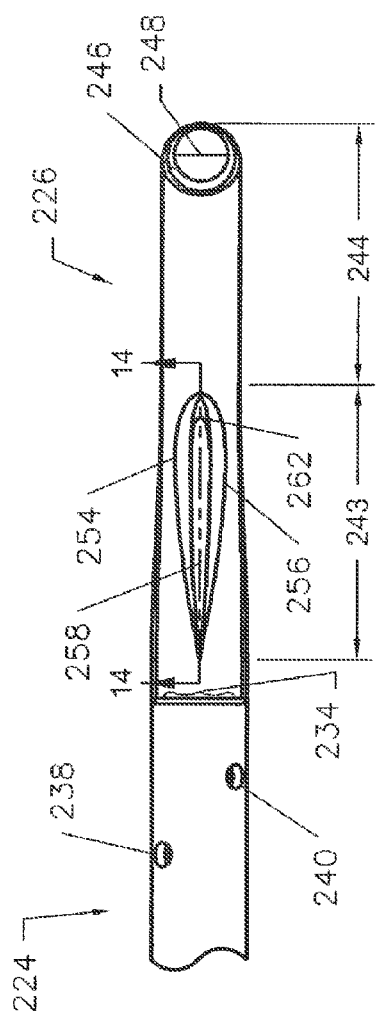
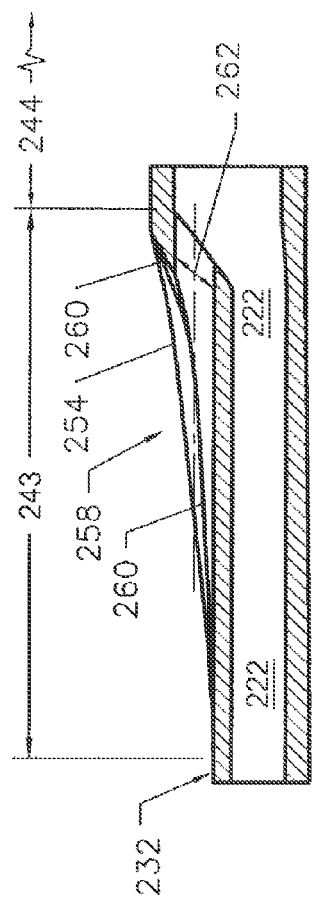
FIG. 13
FIG. 14

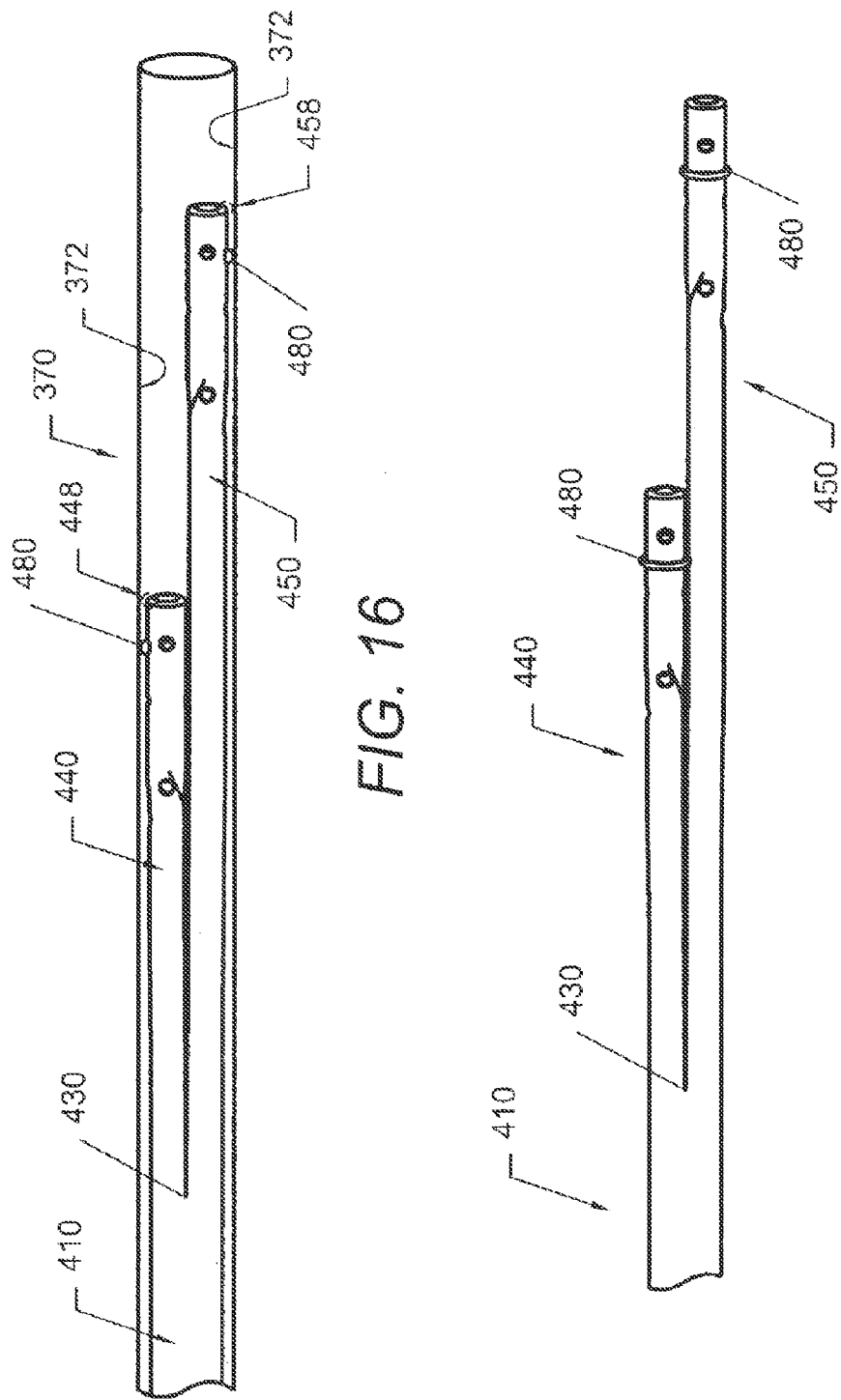

US 9,387,304 B2

MULTI-LUMEN CATHETER WITH SEPARATE DISTAL TIPS

PRIORITY

This application is a continuation of U.S. patent application Ser. No. 11/874,447, filed Oct. 18, 2007, now U.S. Pat. No. 8,808,227, which is a continuation of U.S. patent application Ser. No. 10/371,774, filed Feb. 21, 2003, now U.S. Pat. No. 7,393,339, each of which is incorporated by reference into this application as if fully set forth herein.

FIELD OF THE INVENTION

The present invention relates generally to a multi-lumen catheter having a plurality of separate distal tips and more particularly to an improved split-tip catheter.

BACKGROUND OF THE INVENTION

Multi-lumen catheters are used for the purpose of creating two or more separate fluid pathways, such as in hemodialysis applications. A primary goal of hemodialysis access is to provide a reliable and effective means of dialysis, which means that a sufficient volume of blood over a period of time must be removed from and returned to the patient. Because the contaminated and cleansed blood must be kept separate for an effective dialysis procedure, a dual lumen catheter is generally used. These dual lumen catheters are usually configured so that there is a shorter lumen that aspirates blood from a blood vessel of a patient to a dialysis machine where it is processed for the removal of toxins, and a longer lumen that infuses the purified blood to the patient. The shorter lumen utilized for aspiration is generally referred to as the "arterial lumen," while the longer lumen utilized for infusion is generally referred to as the "venous lumen." The reason for the different lengths is to minimize co-mingling of aspirated and infused blood.

The primary problems occurring in dual lumen dialysis catheters are blood clotting (thrombosis) and fibrin (the protein formed during normal blood clotting that is the essence of the clot) sheath formation. Thrombus and fibrin sheath formation can occlude distal tips of the dialysis catheter lumens, resulting in loss of catheter function when such an occlusion prevents blood flow. This typically occurs initially in the arterial lumen used for aspiration of blood from a patient. A secondary problem relates to the arterial lumen "sucking" against the vessel wall, in which the arterial lumen openings become fully occluded by the patient's vasculature.

To specifically address these problems, a new type of dialysis access catheter has been designed that utilizes independent "free floating" distal tip sections that separate at a distal end of the catheter to theoretically reduce the likelihood of potential occlusion and "sucking" during dialysis treatment. U.S. Pat. No. 6,001,079 to Pourchez and U.S. Pat. Nos. 5,947, 953 and 6,190,349 to Ash et al., all incorporated by reference herein, are directed to said new type of catheter, hereinafter referred to as a "split-tip catheter."

Catheters used for hemodialysis are generally inserted according to standard technique. This includes identifying the location of the central veins in which the catheter is to be inserted, utilizing the Seldinger technique to cannulate the central vein with a guidewire, and passing various instruments over the guidewire until the catheter is in place. In the case of a small diameter catheter made of relatively stiff material (i.e., a percutaneous catheter for acute access), the catheter itself can be passed over the guidewire and into the central vein. In the case of a larger diameter catheter, the passage to the central vein must be widened through the use of dilator(s), after which the catheter can be passed over the guidewire. Another possibility available to the physician is to use an introducer sheath, which is passed over the guidewire (after dilation or simultaneously therewith) forming a path for the catheter to access the central vein.

Due to the configuration of the split-tip catheter, standard insertion techniques must be modified. With respect to non-sheath insertions, the separate distal tip sections must each be passed over the guidewire to ensure their arrival at the targeted central vein without attendant problems. Suggested means for accomplishing this (in a dual lumen catheter) is to pass the back end of the guide wire through the distal end hole of one tip section and out a side hole thereof into the distal end hole of the other tip section (Patel et al., J. Vasc. Interv. Radiol. (2001), vol. 12, pages 376-378). However, such a method can become problematic depending on the placement of the side holes and, in fact, may be impossible in the event that no side holes are provided. With respect to sheathed insertions, the separate distal tip sections may tend to flare outward and catch or "snag" on the inner wall of the delivery sheath thereby preventing smooth delivery of the catheter to the central vein.

There is a need for improvements to split-tip catheters and new configurations thereof, which enhance the design and further alleviate concerns with regard to typical problems encountered in hemodialysis catheters. There is also a need for new configurations and new methods for insertion of split-tip catheters to overcome problems associated therewith

SUMMARY OF THE INVENTION

In accordance with the present invention, several embodiments are described, which may be improvements to prior art split-tip catheters or may be novel catheter embodiments heretofore undisclosed. As used herein, the following terms have the following meanings:

"Split-tip catheter" refers to a catheter having a body enclosing at least two lumens and a dividing point that separates at least two tip sections from one another distal thereto, each of the tip sections enclosing at least one lumen and being separated or separable from one another along their length.

"Dividing point" refers to a point along the length of the split-tip catheter distal to which at least two tip sections are separated or are separable from one another.

"Tip section" refers to a portion of the split-tip catheter, enclosing at least one lumen, which is separable or is separated from another tip section along its length distal to a dividing point.

"Inner surface" refers to a surface on a tip section that is facing or adjacent a companion tip section (a tip section that separates or is separable distal to the same dividing point).

"Outer surface" refers to a surface on a tip section that is not facing a companion tip section.

"Separation force" refers to a force required to separate the tip sections from one another.

"Excessive separation force" refers to a force required to separate the tip sections from one another, which is too great to be considered practical for a clinician in a typical setting. By definition, an excessive separation force is required to separate the tip sections of the split tip catheter from one another proximal to the dividing point.

"Cylindrical" is used according to its ordinary meaning (i.e., a shape having a constant circular cross-section).

One improvement to prior art split-tip catheters comprises a unique configuration of each tip section to improve flow characteristics, provide ease of delivery and overcome typical problems associated with hemodialysis catheters. In a dual lumen embodiment, the split-tip catheter comprises a shorter arterial tip section comprising a semi-cylindrical shape with a rounded distal end, and a longer venous tip section comprising a semi-cylindrical shape in a proximal portion which smoothly transitions in a transition region to a cylindrical shape in a distal portion, the cross-sectional size of the distal portion being greater than the cross-sectional size of the proximal portion, the distal portion terminating in an inward bevel. Another improvement comprises the strategic placement of openings placed on the tip sections of the split-tip catheter. With particular respect to an arterial tip section in a dual lumen configuration, the openings are offset both longitudinally and circumferentially so that full 360° fluid flow is realized and problems related to "sucking" against the vessel wall are mitigated.

Another improvement to the prior art split-tip catheters comprises a means for reducing dead space on the surface of the tip sections of a split-tip catheter in the region of separation, which includes, but is not limited to, an opening or openings located on an inner surface of one or more tip sections near a dividing point of the split-tip catheter. In one embodiment of the invention, a hole or opening is positioned on an aspirating lumen tip section. In another embodiment of the invention, a hole or opening is positioned on an infusion lumen tip section. In each of these embodiments, there could be multiple holes or openings on the lumen tip sections. Additionally, the hole(s) or opening(s) could be positioned in many different locations along the length of the tip sections and/or catheter.

An additional improvement to prior art split-tip catheters is related to the delivery thereof either with or without the use of a delivery sheath. With respect to a non-sheathed delivery, the improvement concerns strategic placement of a guidewire opening in the distal end of the venous tip section so that the guidewire is easily passed through the venous tip section and into the arterial tip section. With respect to a sheathed delivery, the improvement relates to a friction-reducing means for reducing friction between the catheter and a delivery sheath. As discussed above, movement of the delivery sheath with respect to the split-tip catheter can result in the inside surface of the delivery sheath engaging the tip sections, which can cause tears in the delivery catheter, problems in the delivery process and other unwanted occurrences.

Thus, in one embodiment of the invention, a bump or protrusion of material is positioned on the outer surface of one or more tip sections adjacent the inside surface of the delivery sheath. In another embodiment of the invention, a ring of material is positioned around the end of one or more tip sections. In yet another embodiment of the invention, an inflatable material is positioned on the outer surface of the catheter in one or more locations to be inflated during delivery to provide a buffer zone for prevention of direct contact of the tip sections with the inside surface of the delivery sheath. Following delivery of the split-tip catheter, said material would be deflated. In still another embodiment, bumps or protrusions of material are positioned on the inside surface of the sheath.

With respect to prior art split-tip catheters that are releasably joined or "splittable," an improvement is described in which tip sections that are initially joined together distal to a dividing point can be separated along a predetermined length thereof upon an application of a particular separation force. In this aspect of the invention, the separation force required to disjoin the tip sections varies along the length of the tip sections (in the described embodiments the separation force increases from the distal end to the proximal end of the catheter) as the bond between the tip sections is varied.

Thus, in one embodiment, the splittable tip sections are releasably joined to one another distal to a dividing point, enabling split and joined configurations to be interchangeable. In another embodiment of the invention, the bond between the splittable tip sections varies in a continuous fashion along their length in such a way that the force required to separate them is progressively increased in a straight line fashion as measured from a distal end of the tip sections to the dividing point. In yet another embodiment of the invention, the required separation force increases in incremental steps as measured from a distal end of the tip sections to the dividing point. In each of these embodiments, while the tip sections are splittable along a predetermined length of the catheter distal to a dividing point, it should be appreciated that said dividing point is a fixed point beyond which separation can not take place without use of excessive separation force.

These and other embodiments, features and advantages of the present invention will become more apparent to those skilled in the art when taken with reference to the following more detailed description of the invention in conjunction with the accompanying drawings that are first briefly described

BRIEF DESCRIPTION OF THE DRAWINGS

FIG. 5 is a perspective view of a straight version of a split-tip catheter according to the present invention.

FIG. 6 is a perspective view of a precurved version of a split-tip catheter according to the present invention.

FIG. 9 is a perspective view of FIG. 7 taken along line 9-9.

FIG. 10 is a cross-sectional view of FIG. 9, taken along line 10-10.

FIG. 13 is a perspective view of FIG. 12 taken along line 13-13.

FIG. 14 is a cross-sectional view of FIG. 13, taken along line 14-14.

FIG. 16 is a perspective view of the tip sections of a split-tip catheter according to one embodiment of the present invention.

FIG. 17 is a perspective view of the tip sections of a split-tip catheter according to another embodiment the present invention.

DETAILED DESCRIPTION OF THE INVENTION

The following detailed description should be read with reference to the drawings, in which like elements in different drawings are identically numbered. The drawings, which are not necessarily to scale, depict selected preferred embodiments and are not intended to limit the scope of the invention.

The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

The present invention is directed to multi-lumen catheters with separate distal tips in the form of improvements over prior art split-tip catheters as well as new configurations and embodiments. While the examples and embodiments of a multi-lumen catheter are discussed herein in terms of a dialysis catheter, it should be appreciated that there are many other possible uses for a multi-lumen catheter of the type presented herein. Also, while a currently preferred material is medical grade polyurethane, it should be appreciated that a variety of suitable materials could be utilized to form the multi-lumen catheter of the present invention. Importantly, the material chosen should possess characteristics such as flexibility, durability and relative softness and conformability when placed within a blood vessel.

Figure 1:
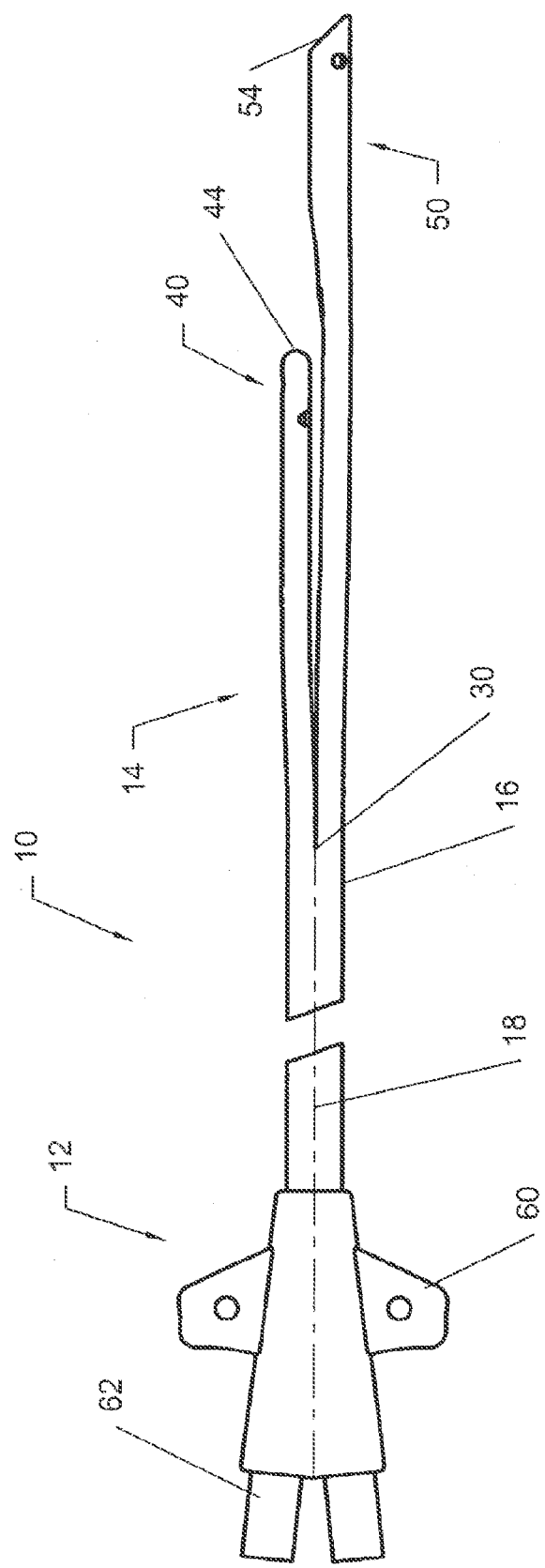
FIG. 1 is a perspective view of a split-tip catheter according to the present invention.

Referring now to FIG. 1, a split-tip catheter 10 is shown having a proximal end 12 and a distal end 14. The proximal end of the catheter 12 is attached to a Y-connector 60, which in turn is connected to extension tubing 62, as is standard in dialysis catheters. The catheter 10 has two lumens defined by an outer wall 16 and a bisecting planar septum 18. The two lumens extend from the proximal end of the catheter 12 to the distal end of the catheter 14 and have a D-shape configuration due to the planar septum 18. Of course, this is not the only possible configuration and certainly the lumens could assume a variety of shapes, including circular, crescent-shaped, oval, etc. The Y-connector 60 and extension tubing 62 fluidly connect the lumens to a blood treatment unit or dialysis machine (not shown). The distal end 14 of the catheter 10 is separated into tip sections 40 and 50 distal to a dividing point 30. While only two tip sections are shown in FIG. 1, it is certainly possible for a plurality of tip sections to branch from the dividing point 30, depending, for example, on the number of lumens within the catheter 10. Thus, it is contemplated that three, four or more tip sections could separate or be separable distal to the dividing point 30, corresponding to three, four or more lumens within the catheter 10.

Figure 2:
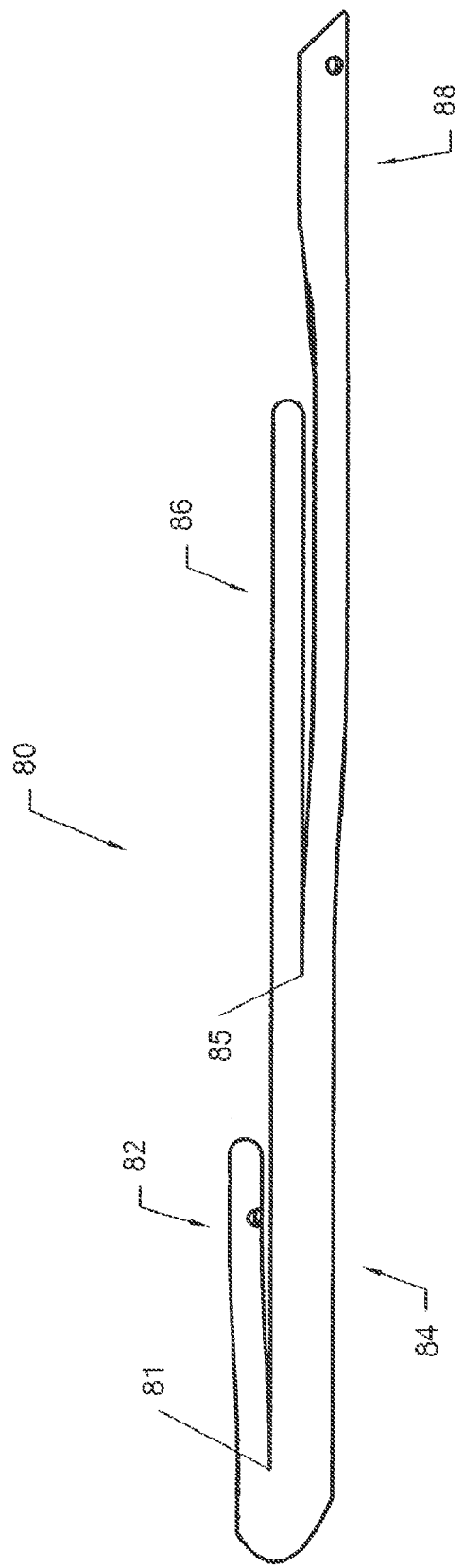
FIG. 2 is a perspective view of an alternate embodiment of a split-tip catheter according to the present invention.

In addition, although only one dividing point is illustrated in FIG. 1, it is contemplated that two or more could be utilized, which is shown as an alternate embodiment in FIG. 2. A multi-lumen catheter 80 has a first tip section 82 and a second tip section 84 distal to a first dividing point 81 and a third tip section 86 and a fourth tip section 88 distal to a second dividing point 85 distal to the first dividing point 81 along the second tip section 84. Of course, it would be possible to have additional dividing points and tip sections, which could accommodate any number of multi-lumen configurations. Referring back to FIG. 1, the two lumens of the catheter 10 continue from the proximal end 12 to the distal end 14 into respective tip sections 40 and 50 distal to the dividing point 30. The lumens can be of equal size and shape from proximal to distal end or can vary in one or more locations. Thus, for example, if it was desirable to increase the flow of blood, the lumen in tip section 50 could increase in cross-sectional area distal to the dividing point 30 so that blood flowing out of tip section 50 would have a reduced velocity.

Figure 3:
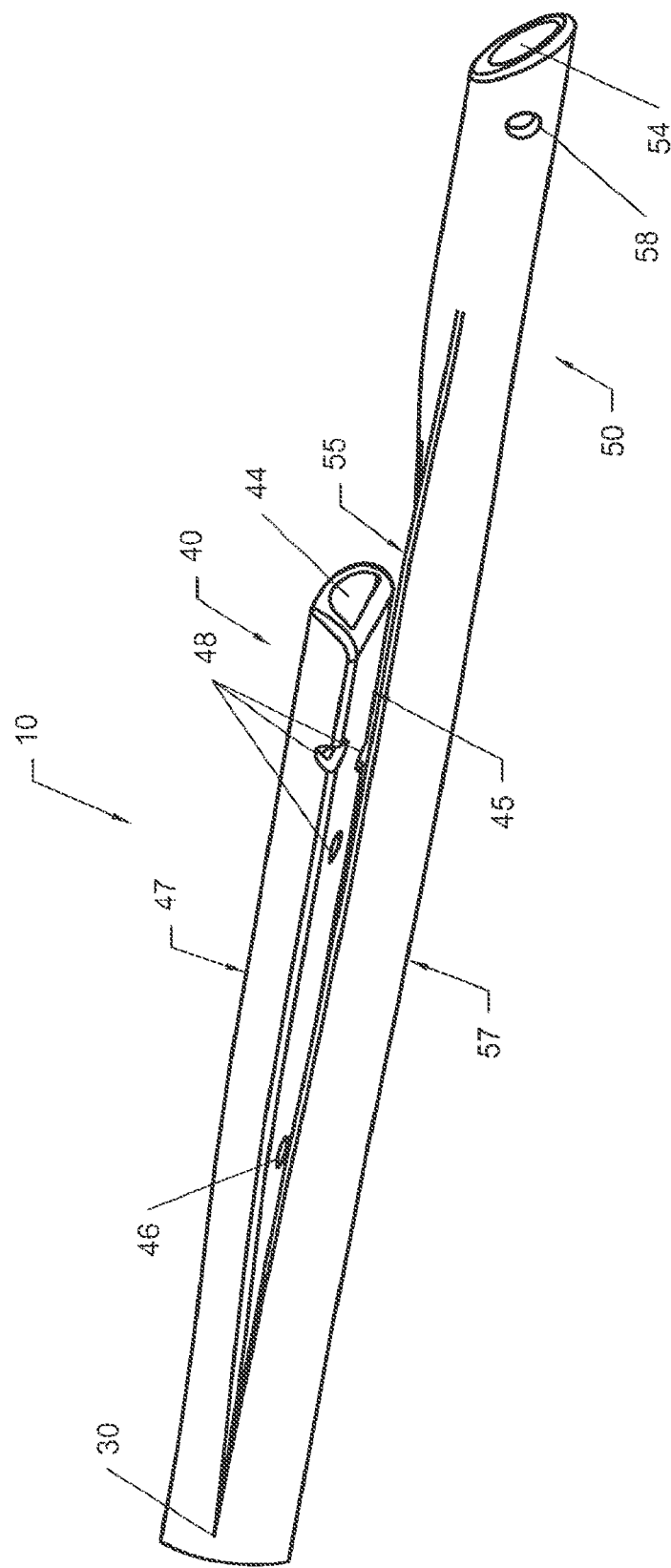
FIG. 3 is a close-up view of the tip sections of the split-tip catheter of FIG. 1, illustrating the positioning of openings therein.

Referring now to FIG. 3, the cross-sectional shape of the lumen within tip section 50 transitions from a D-shape to a circular shape, the transition occurring distal to the end opening 44 of tip section 40. Such a configuration for the tip section 50 is optimal for many reasons, which will be explored below with reference to FIGS. 7-14. Importantly, the overall configuration for the distal end 14 of the catheter 10, including the shape of tip sections 40 and 50, has been found to be optimal regarding delivery of the catheter into a body lumen as well as with respect to its performance in vivo.

As shown in FIGS. 1 and 3, tip section 40 terminates in a rounded configuration and tip section 50 terminates in a beveled configuration, providing end openings 44 and 54 therethrough. While certainly there are many degrees of angles that can be used for the bevel cut according to the present invention, the currently preferred range is between approximately 25° and 75°, while the angle shown is approximately 45°. Of course, there are a multitude of end configurations possible for each tip section in addition to those shown, including blunt, tapered, curved, notched, etc. In particular, a reverse bevel or notched (area removed from the end) configuration could be formed in the tip section 40 to minimize the opportunity for "sucking" against the wall of the superior vena cava or right atrium during a dialysis procedure. As is standard for dialysis catheters, tip section 40 is used to aspirate blood from the patient, while tip section 50 is used to infuse treated blood from a dialysis machine, as discussed above.

FIG. 3 illustrates one of the stated improvements over the prior art split-tip catheters, namely the presence of an opening in close proximity to the dividing point, by showing the tip sections of FIG. 1 in more detail. Tip sections 40 and 50 distal to dividing point 30 have inner surfaces 45 and 55 and outer surfaces 47 and 57 respectively. In close proximity to the dividing point 30 on inner surface 45 is positioned an opening 46, providing an additional inlet on the tip section 40 for the aspiration of blood. Importantly, opening 46 addresses an apparent problem with certain split-tip catheter designs with respect to clotting and fibrin sheath formation at or near the dividing point. This phenomenon is likely due to the unused surface area proximal to the arterial and venous end openings 44 and 54, which increases the surface area for platelet adhesion. By positioning opening 46 in close proximity to the dividing point 30, blood flow therethrough acts to dislodge any clot formation on the inner surfaces 45 and 55. In addition, the presence of one or more openings in close proximity to the dividing point may permit slow leaching of heparin along the inner surfaces 45 and 55, which also would prevent clot formation as the catheter lumens are flushed between dialysis treatments. As used herein, the term "close proximity" refers to a distance that is nearer the dividing point than the distal end of the subject tip section and can refer to any point along the length of the subject tip section in that range.

Figure 4:
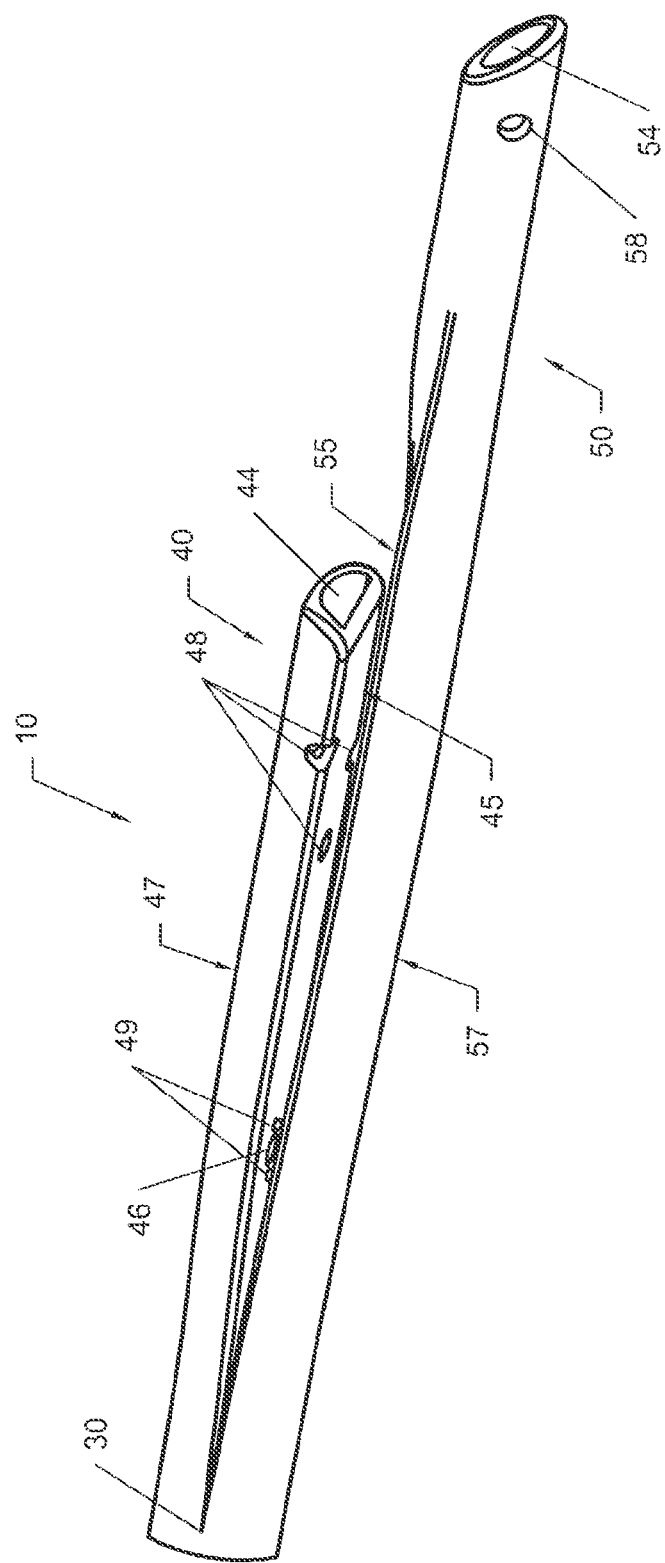
FIG. 4 is a similar view to FIG. 3, illustrating an alternate embodiment thereof.

It should be appreciated that even though one hole on inner surface 45 is shown in FIG. 3, a plurality of openings are also possible and may even be preferable, depending on the particular application. In addition, although a small circular opening 46 is shown, certainly other shapes and sizes would be equally within the scope of the invention, including oval shapes, slits, etc. For example, an opening near the dividing point could comprise a valve such as that described in U.S. Pat. No. 4,549,879 to Groshong et al., which is incorporated by reference herein. By utilizing a valve, leaching may be controlled, which could be advantageous in certain situations, depending on the patient's disposition. In an alternate embodiment, small mounds of material or protrusions 49 are positioned adjacent the opening 46 on either side thereof as shown in FIG. 4. Of course, while two protrusions 49 are shown, certainly any number of protrusions 49 are contemplated. The protrusions 49 serve at least two purposes, including maintaining separation between the tip sections 40 and 50 and preventing opening 46 from becoming occluded.

While the embodiment shown in FIG. 3 illustrates opening 46 on inner surface 45, it may instead be preferable to place one or more openings on the inner surface 55 of tip section 50. Alternatively, it may be desirable to place one or more openings on both inner surfaces 45 and 55 at similar positions or offset from one another. Similar arrangements are also contemplated with respect to the presence of an opening or openings near the dividing point in catheters having more than two tip sections or more than one dividing point as discussed above, as well as with respect to the use of protrusions near or around the openings. In a split-tip catheter having tip sections that are releasably joined, an opening or openings could be placed at intervals along the length of at least one of the tip sections on an inner surface thereof.

Both tip sections 40 and 50 may include side hole(s) 48 and 58 respectively, positioned near their terminal end for enhanced fluid flow into and out of the tip sections 40 and 50. As should be appreciated by one of skill in the art, many embodiments with respect to the side hole(s) are possible, including an embodiment with no side holes. The side hole(s) 48 and 58 can be positioned at various locations around the circumference of the tip sections 40 and 50 and can be one or several in number. As shown in the embodiment of FIG. 3, tip section 50 has one side hole 58 in the side thereof, while tip section 40 has four side holes spaced in different locations around its circumference and offset lengthwise from the end opening 44. This particular configuration will be explored below in reference to FIGS. 7-8.

FIGS. 5-11 illustrate an embodiment of the split-tip catheter of the present invention similar to that depicted in FIG. 1. FIG. 5 depicts a straight configuration of a split-tip catheter 100, while FIG. 6 depicts a precurved configuration thereof. In each instance the split-tip catheter 100 includes a flexible cylindrical catheter tube 114 that encloses a pair of distinct lumens. In the precurved configuration in FIG. 6, a medial portion of the catheter tube 114 is formed into a bend 116. The distal end 128 of the split-tip catheter 100 is bifurcated into a pair of distal tip sections 124, 126, which are distal to a dividing point as discussed above. Each of the tip sections 124, 126 enclose a lumen that is respectively continued from the pair of distinct lumens enclosed in the catheter tube 114.

Figure 7:
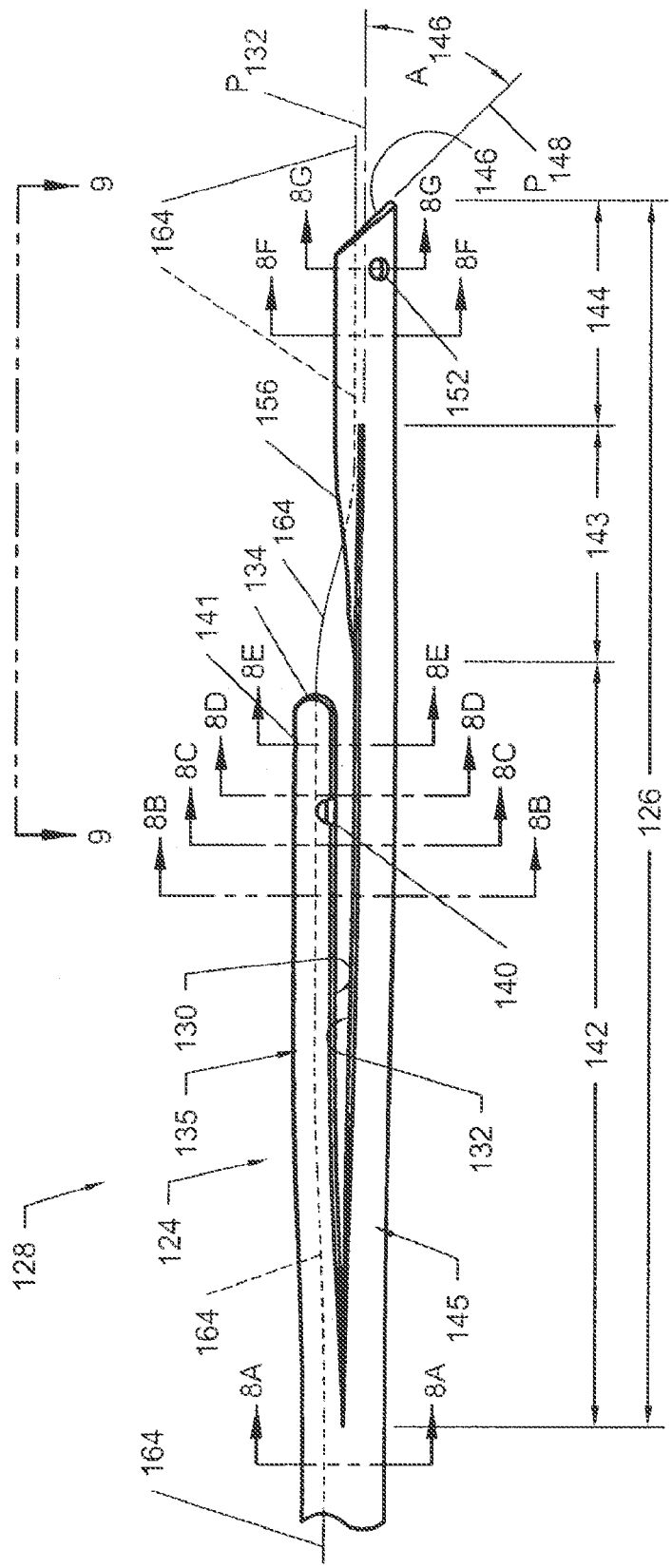
FIG. 7 is a close-up view of the distal end of the split-tip catheter of FIGS. 5 and 6.
Figure 8:
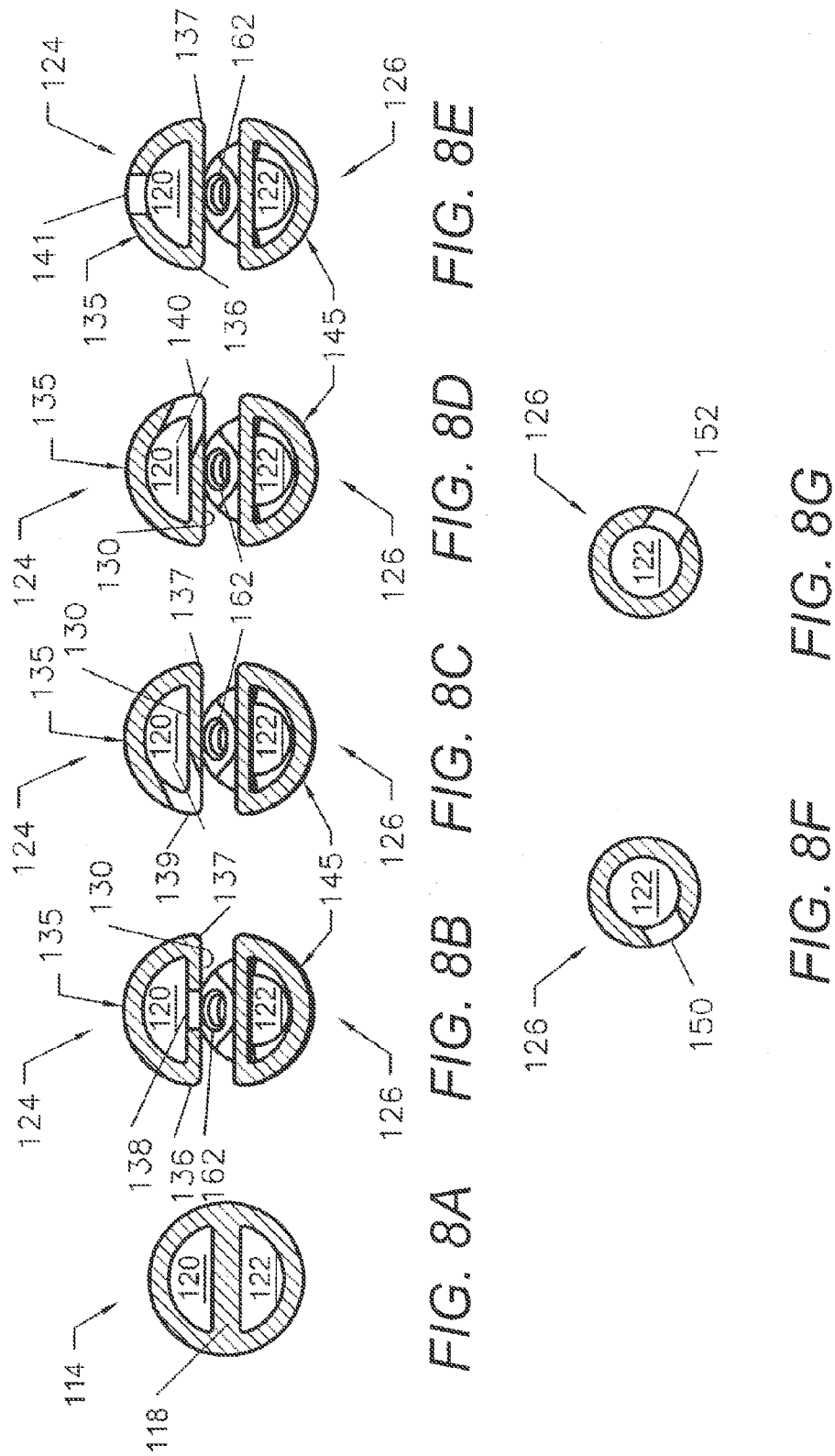
FIGS. 8A-8G are cross-sectional views of the distal end of the split-tip catheter of FIG. 7, taken along lines 8A-8A, 8B-8B, 8C-8C, 8D-8D, 8E-8E, 8F-8F, 8G-8G, respectively.

FIGS. 7-8 illustrate the distal tip sections 124, 126 in greater detail. As seen in FIG. 8A, the catheter tube 114 encloses substantially similar D-shaped lumens 120, 122 separated by a planar septum 118. These lumens 120, 122 continue on into the distal tip sections 124, 126 respectively, the lumen 120 and associated tip section 124 being the shorter arterial lumen and tip section that is used to withdraw blood from the cardiovascular system for dialysis treatment outside the body, and the lumen 122 and associated tip section 126 being the longer venous lumen and tip section that is used to return blood to the cardiovascular system following said dialysis treatment. The arterial tip section 124 has a planar surface 130 which faces and is adjacent to a planar surface 132 of the venous tip section 126, each of the planar surfaces 130, 132 being extensions of the planar septum 118 distal to the dividing point.

Similar to the embodiment shown in FIG. 1, the distal arterial tip section 124 terminates in an end opening 134 that assumes a semicircular profile when viewed from the side (FIG. 7). While the lumen 120 is D-shaped and continues through the end opening 134 as such (i.e., the lumen 120 does not taper or enlarge), the side view shows a semicircular profile due to the edges of the distal end of the arterial tip section 124 being rounded. This rounding can be seen in greater detail in FIGS. 3 and 4 as well as in FIG. 9, which illustrates a view from the side of the arterial tip section 124 identified by line 9-9 in FIG. 7. As shown, an edge 133 of the distal end of the arterial tip section 124 assumes a scalloped configuration as a result of the rounding process. Such rounding is accomplished by heating with radio frequency (RF) energy, although certainly many other methods of heating could be utilized, but is not limited to the distal end of the arterial tip section 124. Indeed, rounding of the split-tip catheter 100 can be employed on various edges and ends thereof.

As mentioned, the D-shape of the arterial tip section 124 is unchanged along the full length thereof, having planar surface 130 and a semicircular surface 135 that interconnects rounded corners 136 and 137 at the lateral ends of the arterial tip section 124 (see FIGS. 8B-8E) and having an end opening 134 as explained above. Arterial tip section 124 also has four additional openings for withdrawing blood and for maintaining patency of the lumen 120 and arterial tip section 124 in the event that the end opening 134 is somehow blocked, the four openings being strategically placed in a longitudinal and circumferential pattern for maximum effect. Specifically, opening 141 can be seen in FIG. 9 (and FIG. 8E), just proximal to the end opening 134 in the semicircular surface 135, while FIGS. 8B-8D show openings 138, 139 and 140.

In FIG. 8B, opening 138 is through the planar surface 130 of arterial tip section 124, to provide a pathway for blood flow between the arterial and venous tip sections 124, 126, thereby reducing blood stagnation between the tip sections as discussed above in connection with FIGS. 3 and 4 (showing openings adjacent the dividing point 30). Opening 138 is positioned at a longitudinal location proximal to opening 141. FIGS. 8C and 8D show openings 139 and 140 respectively through the corners 136, 137. These side or corner openings 139 and 140 are offset as can be appreciated from FIG. 7, opening 139 being positioned at a longitudinal location proximal of opening 140, each of which openings are proximal of opening 141. As depicted, the openings are approximately equidistant from one another, or more precisely, the distance between each consecutive opening 138-141 in the arterial tip section 124 is substantially the same. It should be specifically noted that side openings 139 and 140 are multi-planar in nature having portions formed through adjacent sides of the catheter (i.e., planar surface 130 and semicircular surface 135). The multi-planar aspect of the side openings 139 and 140 is particularly advantageous with respect to prevention of occlusion of the arterial lumen due to the remote possibility that either of the openings could be completely obstructed by a vessel wall.

The positioning of the openings 138-141, as well as the distance therebetween, is very important with respect to the stated goals of facilitating blood flow and maintaining patency of the catheter. By positioning each opening at longitudinal locations offset from one another (and in this case approximately equidistant from one another) as well as at different points around the circumference of the arterial tip section 124, alternative flow through the arterial tip section 124 is permitted, preventing thrombus and fibrin formation as well as "sucking" against the vessel wall. More specifically, the offset positioning on four different sides enables 360° multi-planar flow into the arterial tip section 124 with five effective sides (including the end opening 134) for the receipt of blood, such that total occlusion of the arterial tip section 124 is largely eliminated.

The distal venous tip section 126 comprises a proximal portion 142, a transition region 143 and a distal portion 144. The proximal portion 142 has a semicircular cross-section similar to the arterial tip section 124 that is unchanged from the dividing point to the transition region 143 as can be appreciated by viewing the cross-sections shown in FIGS. 8B-8E. The planar surface 132 of the venous tip section 126 forms a planar outer wall of the proximal portion 142 on the side of the venous tip section 126 adjacent to the arterial tip section 124 as explained above. A semicircular wall 145 interconnects the lateral ends of the venous tip section 126 to complete an enclosure of the venous lumen 122. As with the arterial lumen 120, venous lumen 122 is the same size as its counterpart in the catheter tube 114, although as mentioned above many variations are possible.

The transition region 143 connects the proximal portion 142 to the distal portion 144 and comprises a transition shoulder 156. The transition region 143 continuously changes in cross-sectional shape along its length in transitioning from the semicircular shape of the proximal portion 142 to the circular shape of the distal portion 144. As shown, the transition shoulder 156 is positioned on a side of the venous tip section 126 adjacent the arterial tip section 124, although certainly other configurations are possible with respect to positioning of the transition shoulder. In addition, configurations including multiple transition shoulders are contemplated herein.

The shape of the venous lumen 122 transitions from a D-shape in the proximal portion 142 to a circular shape in the distal portion 144, although the actual cross-sectional area of each shape can be manipulated to accommodate the particular application (i.e., the cross-sectional area of the distal portion with respect to the proximal portion can increase, decrease or remain substantially equivalent). In one embodiment, the cross-sectional area for the venous lumen 122 in the distal portion 144 of the venous tip section 126 is standardized to permit all sizes of the catheter to be tunneled subcutaneously during implantation using a single size of tunneling trocar. Thus, the cross-sectional area of the lumen 122 in the proximal portion 142 of the venous tip section 126 (as well as the cross-sectional area of the proximal portion 142 itself) would vary depending on the size of the catheter. One possibility, therefore, would include an increase in cross-sectional area of the venous lumen 122 from the proximal portion 142 to the distal portion 144 of the venous tip section 126. This could have advantages in that the discharge velocity of fluid flowing out of the end 146 would be reduced, translating into less trauma to the vessel and minimized effects related to shear stress. Of course, it should be apparent to one of skill in the art that various combinations of cross-sectional shapes and sizes for the venous lumen 122 are possible along the length thereof, each of which could enjoy certain advantages and benefits.

The distal portion 144 has a cylindrical shape with an open end 146 that is inwardly beveled in the proximal direction toward a plane $P_{132}$. End opening 148 through the open end 146 is contained in a plane $P_{148}$ that is shown in FIG. 7 as being oriented at a bevel angle $A_{146}$ to plane $P_{132}$. As a result of the bevel, the end opening 148 is necessarily oval shaped. The bevel angle $A_{146}$ is shown as approximately 45°, although as stated above in connection with FIGS. 1 and 3, certainly many other angles are possible, the preferred range being between approximately 25° and 75°. The open end 146 of the venous tip section 126 is rounded (represented by the double line in FIGS. 7 and 9) similar to the end of the arterial tip section 124. Referring to FIGS. 8F and 8G, the distal portion 144 of the venous tip section 126 contains two openings 150 and 152 that are longitudinally offset from one another. As with the various openings described above, openings 150 and 152 can be provided in different shapes and sizes and can be positioned at various points along the venous tip section 126 to provide additional outlets for the flow of blood in the event that a blockage occurs.

FIG. 9 is a view of the distal end 128 of the split-tip catheter 100 perpendicular to plane $P_{132}$ identified in FIG. 7 by line 9-9. FIG. 10 is an enlarged longitudinal sectional view of the venous tip section 126 taken along line 10-10 in FIG. 9, illustrating the transition region 143. Various transverse cross-sectional views of venous tip section 126 taken along various lines in FIG. 10 are shown in FIGS. 11A-11E. Taken together, FIGS. 9-11 reveal that in transition region 143 a shoulder 156 of continuously longitudinally varying width and height projects outwardly from the planar surface 132 of proximal portion 142. Referring to FIG. 9 along with FIGS. 11B-11D, it can be seen that the transition shoulder 156 has a semicircular cross-sectional aspect with a width and a height above the planar surface 132 that increase from the proximal portion 142 to the distal portion 144 such that shoulder 156 is equal to the outer diameter of the distal portion 144 at the distal end thereof.

In FIG. 9, shoulder 156 is shown as having linear lateral boundaries 160 at which the exterior surface of the shoulder 156 emerges from the planar surface 132 of venous tip section 126. The lateral boundaries 160 intersect at a proximal end 158 of the shoulder 156 and are symmetrically disposed on opposite sides of the longitudinal axis $L_{128}$ of the distal end 128 of the catheter 100. While a specific configuration for a transition shoulder is described above, it should be understood that other configurations are possible and are contemplated herein, including, for example, a transition shoulder that decreases in width from the proximal portion 142 to the distal portion 144. In any case, the slope of the shoulder 156 should be positive, although it can be formed with varying degrees with respect to plane $P_{132}$. Thus, although a positive slope of approximately 5° is shown in FIG. 10, certainly many other possibilities exist that would be within the scope of the invention.

The shoulder 156 is penetrated obliquely by a somewhat longitudinally-aligned guidewire aperture 162 that communicates between the exterior of the venous tip section 126 and the venous lumen 122 in transition region 143 and distal portion 144. As clearly seen in FIG. 7, the guidewire 164 is shown extending from arterial lumen 120 through the open end 134 of arterial tip section 124 and through a guidewire aperture 162 in the transition shoulder 156 into the venous lumen 122 of the venous tip section 126, thereby seamlessly connecting the two lumens and tip sections. While threading a guidewire through adjacent tip sections has been preliminarily explored in the prior art, the embodiments disclosed herein are advantageous for several important reasons. For example, the configuration of the tip sections with respect to one another in combination with a transition shoulder having a positive slope and having a guidewire therethrough affords a streamlined approach to connecting the tip sections for ease of delivery to a targeted lumen. In addition, the particular configuration of the inner wall of the guidewire aperture imposes minimal binding stresses on an insertion guidewire, making the split-tip catheter freely slidable thereon.

Although the examples herein with respect to a guidewire aperture are discussed in terms of passage of a guidewire therethrough, it will be appreciated by one of skill in the art that an aperture could also be configured for passage of a stylet or other instrument, such as the applicator discussed in U.S. Pat. No. 5,405,341 to Martin, which is incorporated by reference herein. Assuming a larger diameter for a stiffening stylet when compared to a standard guidewire, such an aperture would tend to be greater in size than the described guidewire aperture, although certainly many sizes and shapes are possible, including slits.

Figure 11:
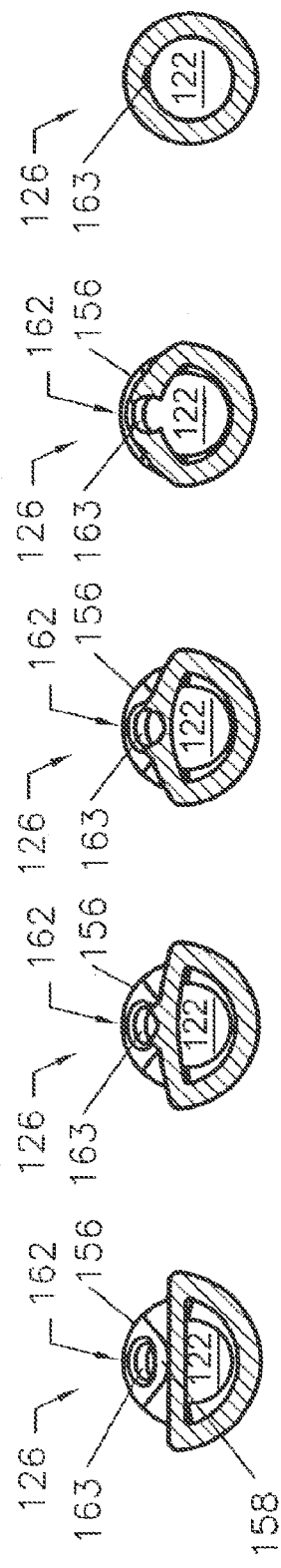
FIGS. 11A-11E are cross-sectional views of FIG. 10, taken along lines 11A-11A, 11B-11B, 11C-11C, 11D-11D, 11E-11E, respectively.

Referring to the transition shoulder 156 as seen in FIGS. 9-11, the guidewire aperture 162 is formed therein, which is bound by an encircling interior wall 163 that has an inner periphery 165 and an outer periphery 166. The interior wall 163 defines an open cylindrical space through the transition shoulder 156 and has a longitudinal central axis $L_{163}$. The guidewire aperture 162 is formed through the wall of the transition shoulder 156 at the point through which it is formed at an angle $A_{162}$, which is the measurement between plane $P_{132}$ and longitudinal axis $L_{163}$. This angle facilitates free slidability of the guidewire through the arterial and venous tip sections 124, 126. It is important to note that many different values for angle $A_{162}$ can be provided, which should equally result in the desired slidability with respect to an insertion guidewire. In particular, it has been discovered that angles (as measured between plane $P_{132}$ and longitudinal axis $L_{163}$) within the range of approximately 0° to 80° provide the desired functionality, with the optimum range being approximately 0° to 45°. The guidewire aperture 162 should be large enough to accommodate passage of a standard 0.038 inch guidewire, but not so large as to permit significant back flow of blood therethrough. In particular, with respect to a 0.038 inch guidewire, it has been discovered that an opening having a radius in the range of approximately 0.039 inch to 0.050 inch is sufficient to allow passage while minimizing unwanted back flow, with the optimum range being approximately 0.039 inch to 0.041 inch. Certainly, however, other radius possibilities exist and would be within the scope of the invention.

In implanting the split-tip catheter 100, the insertion guidewire 164 is threaded into the catheter 100 by first passing the proximal end thereof into end opening 148 of the venous tip section 126 and along the venous lumen 122 within the distal portion 144, through the guidewire aperture 162 and into the end opening 134 of the arterial tip section 124 where it is advanced along the full length of arterial lumen 120 to exit the catheter tube 114 at a proximal end thereof. This course taken by the guidewire 164 is shown in FIG. 7. During implantation into a target vessel, the distal end 128 of the split-tip catheter 100 is slid in a distal direction along guidewire 164 to a desired location, the guidewire having been previously extended thereto.

In another embodiment of the present invention, a guidewire lumen is formed through the distal portion of the venous tip section, but is separate from the venous lumen. Thus, in this embodiment the distal portion of the venous tip section comprises two lumens whereas the proximal portion of the venous tip section comprises only one. This would be possible, for example, by providing a transition region similar to that shown in FIG. 7, where the size of the venous tip section increases from proximal to distal portions. In such a configuration, the venous lumen could remain approximately the same size from the proximal to distal portions with the additional cross-sectional size of the distal portion of the venous tip section being utilized for an additional lumen therethrough. The additional lumen ideally would be positioned at a location in the venous tip section closest in proximity to the arterial tip section (i.e., above the venous lumen in reference to FIG. 7) so that an instrument passing therethrough will have to bend only slightly or not at all when passing out of the arterial tip section and into the venous tip section.

The presence of an additional lumen permits the use of a stiffening stylet as described above, without having to increase the size of the guidewire aperture (which may be advantageous to avoid excessive loss of blood therethrough). Thus, the described embodiment could be formed with or without a guidewire aperture. In the case that a guidewire aperture was not formed through the transition region, the additional lumen could accommodate a guidewire, stiffening stylet or both (in addition to possible other medical instruments). In the case that a guidewire aperture is formed through the transition region, a guidewire and stiffening stylet could be used simultaneously if so desired.

Figure 12:
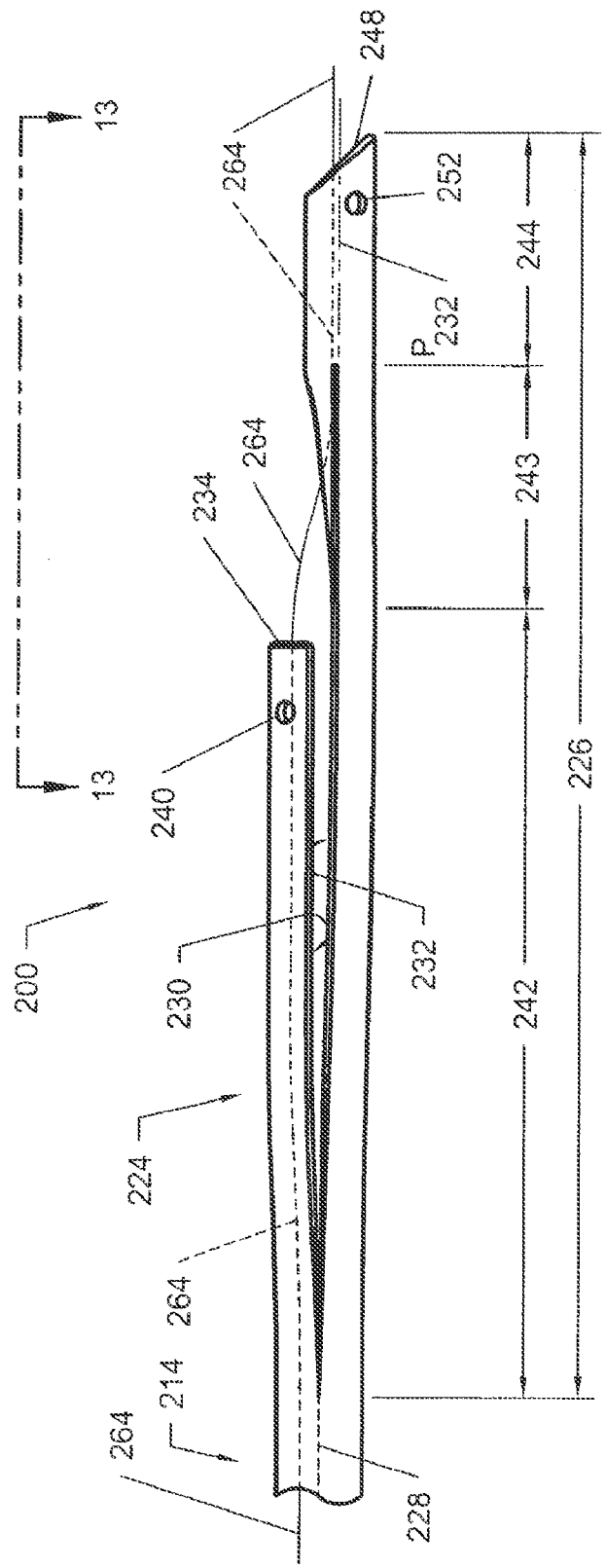
FIG. 12 is an alternate embodiment of the split tip catheter of the present invention, showing a close-up view of a distal end thereof.

An alternate embodiment of the present invention with respect to the configuration of the tip sections is provided in FIGS. 12-14. A split-tip catheter 200 is shown having arterial tip section 224 and venous tip section 226 in FIG. 12, the arterial tip section 224 having a planar surface 230 extending from a dividing point and venous tip section 126 having a planar surface 232 in facing relation thereto. Planar surfaces 230, 232 extend from a planar septum 228, which divides a catheter tube 214 into a pair of distinct lumens that continue into the arterial tip section 224 and the venous tip section 226 respectively distal to the dividing point. Arterial tip section 224 has a terminal end that is cut perpendicular to a longitudinal axis thereof through which an end opening 234 is formed. Arterial tip section 224 contains three additional openings spaced approximately 120 degrees from one another around the circumference of the arterial tip section 224, which are offset longitudinally approximately equidistant from one another. Openings 238 and 240 can be seen in FIG. 13, while the third opening is positioned through the planar surface 230 of the arterial tip section 224.

The venous tip section 226 has a proximal portion 242, a transition region 243 and a distal portion 244 and has an end 246 with an opening 248 therethrough (see FIG. 13). Similar to the above-described embodiment, venous tip section 226 has two openings on opposite sides of the distal portion 244, of which opening 252 is shown in FIG. 12. These openings are offset longitudinally along the length of the distal portion 244. The proximal portion 242 has a cross-sectional semicircular shape, while the distal portion 244 has a cross-sectional cylindrical shape. The transition region 243 increases in width and height in a distal direction moving from the proximal portion 242 to the distal portion 244. The transition region 243 includes a pair of longitudinally extending, parallel reinforcing ridges 254, 256 (FIG. 13), which reduce the bending of the transition region 243 in response to forces imposed on the venous tip section 226 during disposition in the cardiovascular system of a patient. Between the reinforcing ridges 254, 256, the surface of the transition region 243 forms a longitudinally extending recess 258 having a floor 260 (FIG. 14) that rises smoothly and continuously from the planar surface 232 of the proximal portion 242 to the curved outer wall of the cylindrical distal portion 244.

In the vicinity of the curved outer wall of the cylindrical distal portion 244, the floor 260 of the recess 258 is penetrated by a guidewire aperture 262 that communicates between the exterior of the venous tip section 226 and the venous lumen 222 (FIG. 14). The planar surface 232 of venous tip section 226 is extended to a longitudinal point where the floor 260 of the transition region 243 merges with the wall of the cylindrical distal portion 244 so that an overhead view (FIG. 13) does not reveal the guidewire aperture 262. This forms a ledge of sorts that, in combination with parallel reinforcing ridges 254, 256, directs the guidewire 264 and maintains it in position as the split-tip catheter 200 is slid therealong into the cardiovascular system of the patient. To prepare for use, the insertion guidewire 264 is threaded into the split-tip catheter 200 by first passing the proximal end thereof into end opening 248 of the venous tip section 226 and along the venous lumen 222 within the distal portion 244, through the guidewire aperture 262 and into the end opening 234 of the arterial tip section 224 where it is advanced along the full length of arterial lumen 220 to exit the catheter tube 214 at a proximal end thereof.

While the split-tip catheters 100 and 200 are configured to allow for sheathless delivery into a cardiovascular system of a patient due to the presence of guidewire apertures 162 and 262, respectively, an improvement to related to the sheathed delivery of split-tip catheters is illustrated in FIGS. 15-20. With respect to FIGS. 15A-15B, a prior art split-tip catheter 310 is shown within a delivery sheath 370 to illustrate a potential problem solved by the present invention. Tip sections 340 and 350 are shown distal to dividing point 330. Each tip section 340 and 350 transitions at a distal end from a D-shaped lumen to a lumen that is circular in cross-section and each has a terminal end that is cut perpendicular to a longitudinal axis thereof. As shown in FIG. 15A, edges 348 and 358 located at the terminal ends of tip sections 340 and 350 abut the inside surface 372 of the sheath 370. Thus, as shown in FIG. 15B, when the catheter 310 is moved out of delivery sheath 370 and into a blood vessel in a direction 390, the opposing friction force 392 forces the tip sections in an outward direction into the sheath 370 as indicated by arrows 394 and 396. This movement of the tip sections 340 and 350 into the inside surface 372 of the delivery sheath 370 causes the edges 348 and 358 to catch or "snag" on the inside surface 372, resulting in difficult insertions or other attendant problems with the delivery process.

One potential method for alleviating this problem would be to use a larger diameter sheath so that the tip sections will have a greater distance to travel to come in contact with the inside surface of the sheath when the friction forces act on the tip sections, thereby minimizing the chance of a snag. However, this solution is flawed in that snags are still possible and the risk of air embolism is amplified due to the increase in surface area between the catheter and the sheath. FIG. 16 illustrates one embodiment of the present invention that addresses a solution to the sheathed delivery problems described. In particular, a multi-lumen catheter 410 having tip sections 440 and 450 distal to a dividing point 430 is shown, the catheter 410 being positioned within delivery sheath 370 having an inside surface 372. To prevent the terminal ends of the tip sections from catching or "snagging" on the inside surface 372 of the delivery sheath 370, a friction reducing structure is provided.

In FIG. 16, the friction reducing structure is illustrated as a slight protrusion or "bump" of material 480, which is positioned on the outside surface of tip sections 440 and 450 near the terminal ends thereof. Thus, as friction forces tend to push the tip sections outward from a central axis of the catheter 410 upon removal from the sheath 370 and into the blood vessel (as described above), the protrusion 480 provides a buffer to prevent edges 448 and 458 from coming into direct contact with the inside surface 372 of the delivery sheath 370 and also provides a relatively small surface area for contact. Of course, there are many ways for reducing friction utilizing the protrusions as discussed above, including using a plurality of protrusions on the catheter tip sections in various locations along their length. However, the embodiment shown in FIG. 16 is advantageous due to the small surface area utilized, the ease of manufacture and the wide-ranging applicability for use with a variety of catheter configurations.

FIG. 17 illustrates an alternate embodiment for reducing friction, wherein each of the tip sections 440 and 450 have a ring of material 482 around an end thereof distal to the dividing point 430. The rings 482, similar to the protrusions 480, distance the sharp edges of the tip sections 440 and 450 from the inside surface of a delivery sheath and therefore reduce friction forces associated with the delivery of a split-tip catheter from a delivery sheath and into a patient's vessel. The rings 480 may also act as a buffer of sorts for the tip sections 440 and 450 while within a patient's vessel by acting to keep the distal ends from coming into direct contact with the walls of the vessel.

Figure 18:
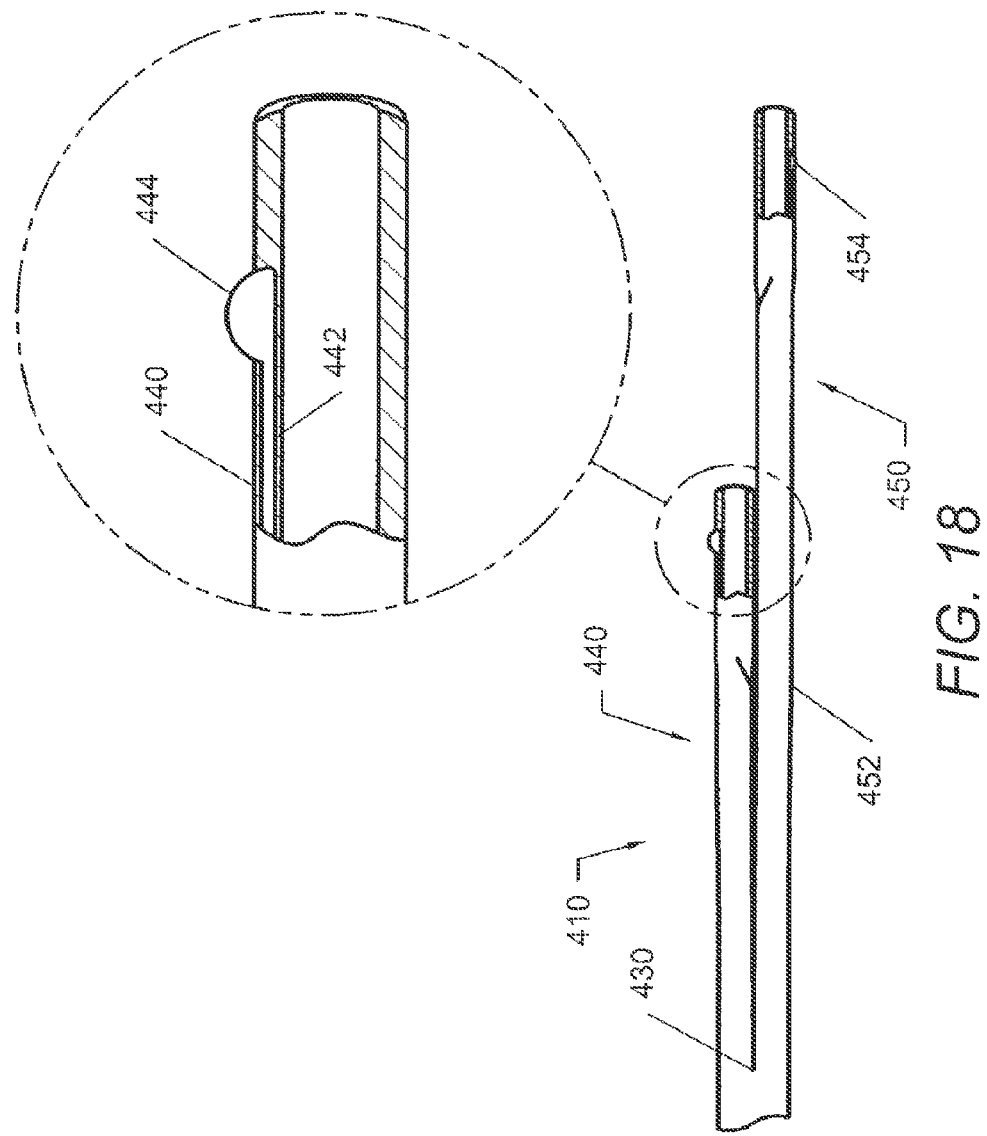
FIG. 18 is a perspective view of the tip sections of yet another embodiment of a split-tip catheter according to the present invention

Another embodiment for reducing friction comprises an inflatable material being positioned on one or more points along the catheter. In this embodiment, a small inflation lumen is positioned on the inner or outer of either or both arterial or venous lumens, extending from the proximal end of the catheter to the point on the catheter containing the inflatable material. When the catheter is positioned for delivery within a delivery sheath, air, gas or liquid is transmitted through the inflation lumen to the inflatable material, expanding said material into contact with the inner of the delivery sheath. Preferably, the inflatable material would be positioned close to the distal end of the catheter on the tip sections so that the goal of preventing the edges of the tip sections from coming into contact with the inside surface of the delivery sheath can be realized. Alternatively or in addition to the goal of reducing friction, placement of inflatable material on various areas on a surface of the catheter could act to remove clots and/or fibrin through the inflation thereof (i.e., by knocking the formations off of the surface upon inflation). Referring now to FIG. 18, the catheter 410 has balloons 444 and 454 positioned near the distal ends of the tip sections 440 and 450, respectively, and are connected to respective inflation lumens 442 and 452. Balloon 444 is shown in its inflated, expanded position for ready contact with the inside surface of a delivery sheath such as delivery sheath 370. Balloon 454 is shown in its deflated, unexpanded position.

Figure 20:
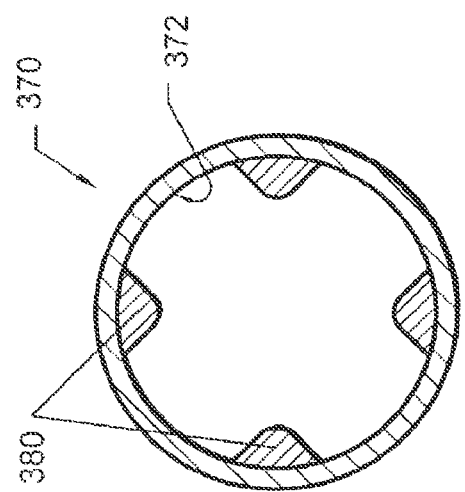
FIG. 20 is a cross-sectional view of FIG. 11 taken along line 20-20.
Figure 19:
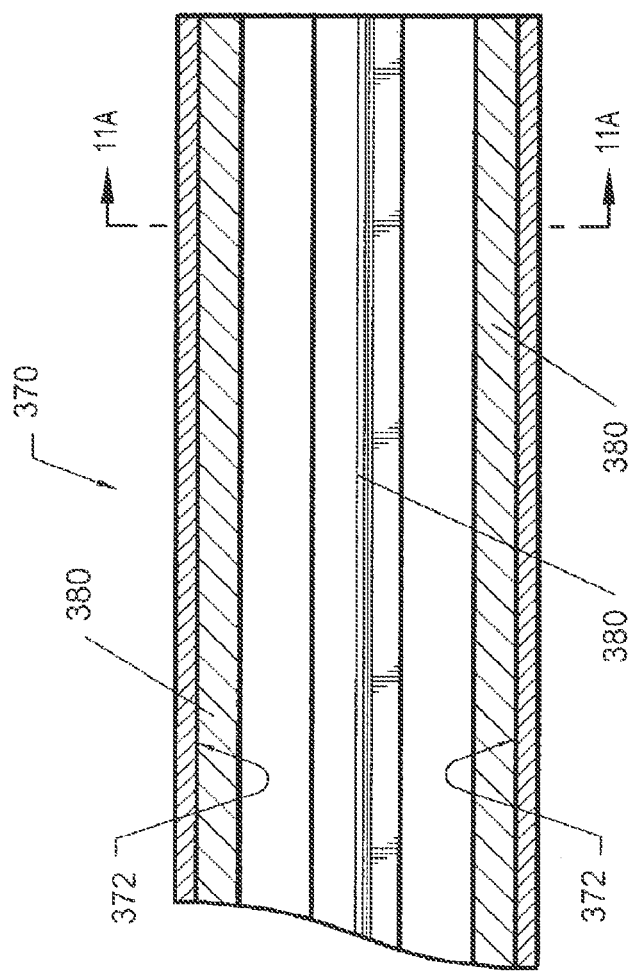
FIG. 19 is an inside view of an introducer sheath according to one embodiment of the present invention.

In yet another embodiment of the present invention, a friction reducing structure is provided by positioning a ridge or ridges 380 on the inside surface 372 of delivery sheath 370, as shown in FIGS. 19 and 20. As with the embodiments involving protrusions positioned on the surface of the catheter, the ridge(s) 380 prevent direct contact of any sharp edges of a tip section with the inside surface 372 of the delivery sheath 370. The ridges 380 can be formed from a mound or bump of material or could also be formed from balloons as described with reference to FIG. 18.

Figure 15A:
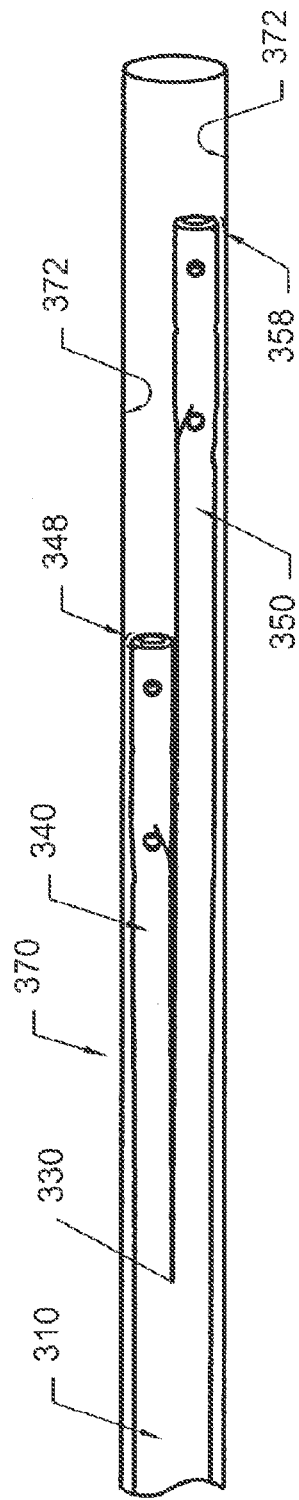
FIG. 15A is an inside view of an introducer sheath containing a prior art split-tip catheter.
Figure 15B:
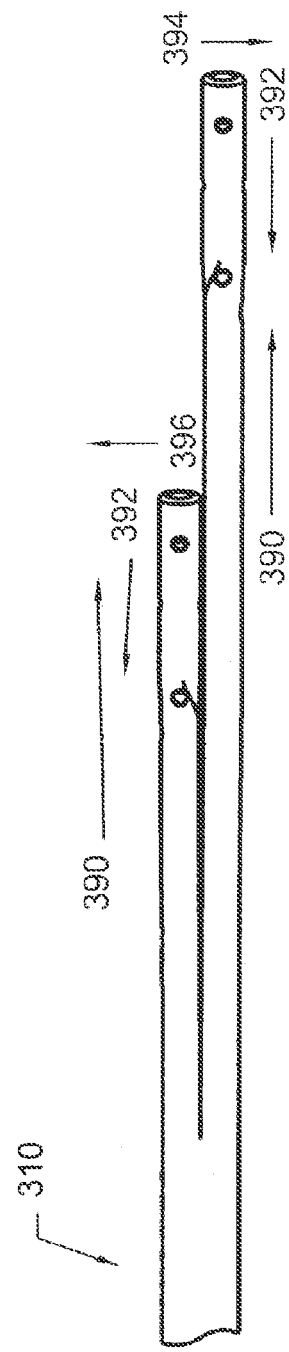
FIG. 15B is a close-up view of the prior art catheter of FIG. 15A, showing forces acting thereon upon delivery out of the introducer sheath.

It is noted that although the delivery problems presented with reference to FIGS. 15A and 15B are certainly more likely to be presented in terminal ends such as those shown, other tip configurations could also present problems with snags or tears, which problems can be minimized through any of the friction reducing structures described above.

Referring now to FIGS. 21A-21H, an improvement to prior art split-tip catheters that are releasably joined or "splittable" distal to the dividing point is illustrated, wherein increasing separation force is required to separate the tip sections from one another. An increasing separation force as used herein means that the bond strength between the tip sections of the catheter will be greater as measured from a distal end toward the dividing point. However, the releasably joined or splittable region need not extend over the entire length of the tip sections and need not begin adjacent the dividing point. Thus, while the releasably joined or splittable region could extend the entire distance from a terminal end of one or more tip sections to the dividing point, it could also span a much shorter distance along the tip sections such that the releasably joined or splittable region is not adjacent either the dividing point or a terminal end of one or more tip sections.

The creation of an increasing separation force between tip sections can be accomplished in a variety of ways, as one of skill in the art should appreciate, some of which ways will be described in detail below (though certainly many others would be within the scope of the present invention). In addition, although the examples herein are described with respect to an increasing separation force, the production of a decreasing separation force is also contemplated, the implementation of which should be apparent to one of skill in the art in light of the discussion regarding an increasing separation force. Further, the discussion with respect to the separation of splittable tip sections herein encompasses both permanent and temporary (i.e., releasably joined) separation.

Figure 21B:
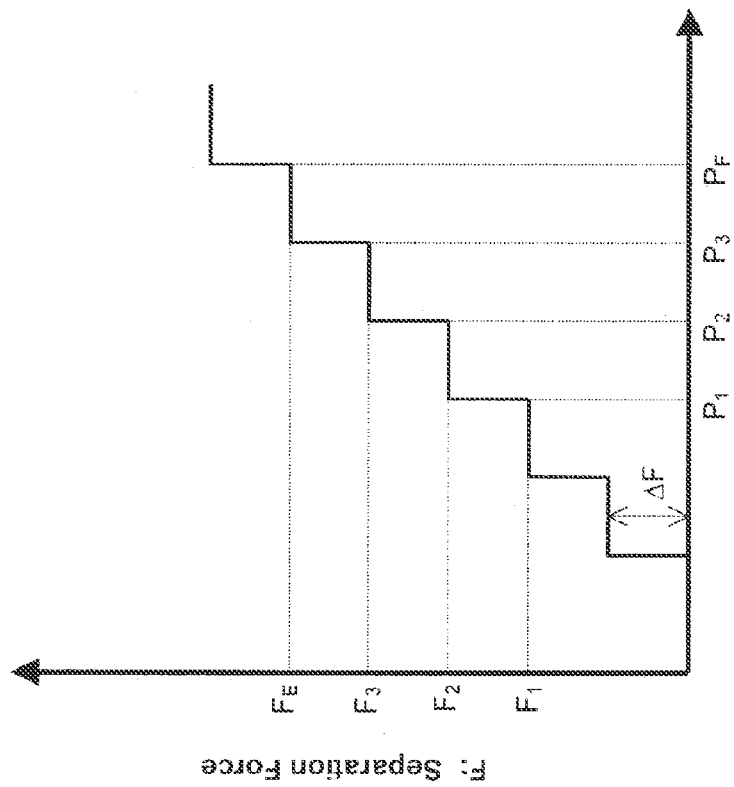
FIG. 21B is a graph illustrating an incremental separation force F as a function of position P of the tip sections.
Figure 21A:
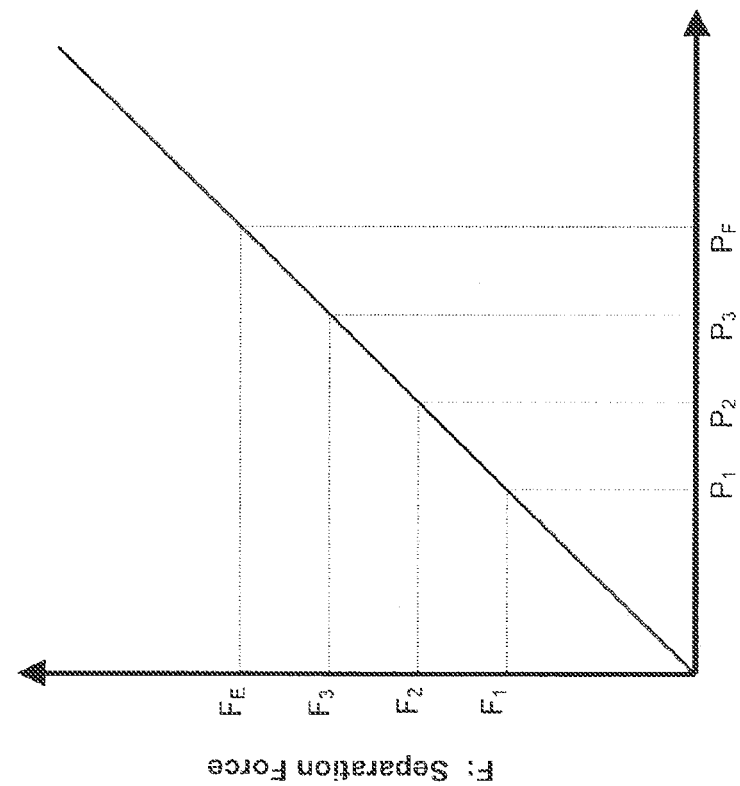
FIG. 21A is a graph illustrating a continuous separation force F as a function of position P of the tip sections.

The concept of increasing the required separation force to separate tip sections from one another is illustrated by way of example, not limitation, through the graphs in FIGS. 21A and 21B. In each of these graphs, the y-axis represents the separation force F required to separate the tip sections from one another and the x-axis represents the position P along the joined portion of the tip sections as measured beginning at a distal end thereof and moving toward the dividing point. The points on the graph, $P_1$, $P_2$ and $P_3$ are points along the joined portion of the tip sections (as further illustrated in FIGS. 21C-21H), having corresponding increasing separation forces $F_1$, $F_2$ and $F_3$. While three distinct points are shown, certainly any number of points are possible and are contemplated herein. The point $P_F$ corresponds to $F_E$, which is the excessive separation force as defined above.

The graphs in FIGS. 21A and 21B illustrate two possibilities for varying the separation force along the length of a split-tip catheter, wherein said force is increasing as a function of position of joined portion of the tip sections when measured beginning at the a distal end thereof and moving in a proximal direction toward the dividing point. FIG. 21A illustrates a straight line continuous separation force, while FIG. 21B illustrates an incremental separation force accomplished in discreet steps, meaning that the change in force ☐ F is too great for spontaneous splitting.

Figure 21C:
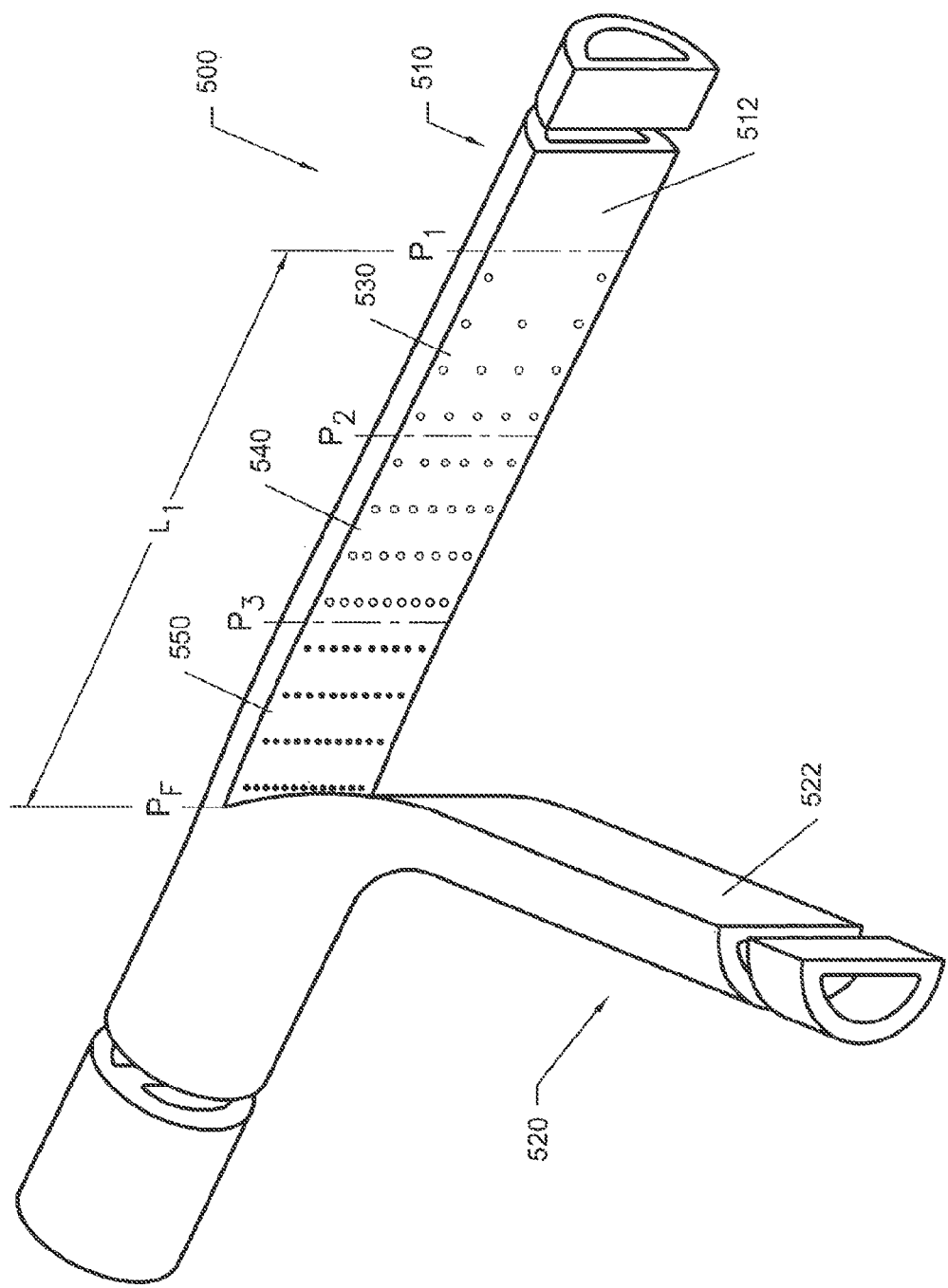
FIG. 21C is a representative view of a split-tip catheter, showing one embodiment of the present invention regarding varying separation force required to separate the tip sections.

One embodiment of tip sections having an increasing separation force is illustrated in FIG. 21C, where fusion points are shown on an inner surface 512 of a tip section 510 of a catheter 500 along a predetermined length $L_1$ (tip section 510 is shown as separated from an adjacent tip section 520 for purposes of illustration). As used herein, the term "fusion point" refers to a fused surface area between a splittable interface and should not be restricted to a "point" per se. Thus, referring to FIG. 21C, the fusion points would be fused surface areas between the inner surface 512 of the tip section 510 and the inner surface 522 of the tip section 520 (even though the tip sections are shown as separate). In this embodiment, the fusion points will preferentially detach upon application of a consistent force relative to the surface area of the fusion.

As shown in FIG. 21C, the fusion points of a first zone 530, formed between $P_1$ and $P_2$, are lighter in shading than the fusion points of a second zone 540, formed between $P_2$ and $P_3$, which in turn are lighter in shading than the fusion points of a third zone 550, formed between $P_3$ and $P_F$. While the shading is shown to be uniform within each zone, one contemplated variation would be to increase the shading (i.e., fusion strength) within each zone when moving toward a higher number (i.e., $P_1$ to $P_2$) as shown in FIG. 21E. In effect, such a configuration creates subzones or additional fusion zones. The darker shaded fusion point in these embodiments represents a fusion point having a greater bond strength, meaning that the fusion points of the third zone 550 would have a greater bond strength than those of the second zone 540, which in turn would have a greater bond strength than those of a first zone 530. This effect could be accomplished, for example, by utilizing different adhesives or solvents for different zones, using various dilutions of adhesives or solvents for different zones, utilizing varying application times of the adhesive or solvent for different zones or using variable pressure upon bonding (more force on one end than another) for different zones, as will be described in greater depth below.

In addition to greater bond strength for the fusion points in adjacent zones in FIG. 21C, the number (density) of the fusion points are increased in each successive zone and within each fusion zone, with the third zone 550 having a greater number of fusion points than the second zone 540, in turn having a greater number of fusion points than the first zone 530. With a greater number of fusion points comes an increased surface area for fusion between inner surface 512 of the tip section 510 and inner surface 522 of the tip section 520, thereby increasing the required separation force when moving from the distal end of the catheter 500 to the proximal end of the catheter 500. Also, with the number of fusion points progressively increasing within each fusion zone, a continuous configuration is created. The combination of greater bond strength in fusion points between adjacent fusion zones and increasing number of fusion points within each fusion zone creates a hybrid continuous/stepped configuration, wherein the separation force increases within each zone following a continuous curve (as represented in FIG. 21A) and increases in a stepped manner with respect to adjacent zones (as represented in FIG. 21B).

Figure 21D:
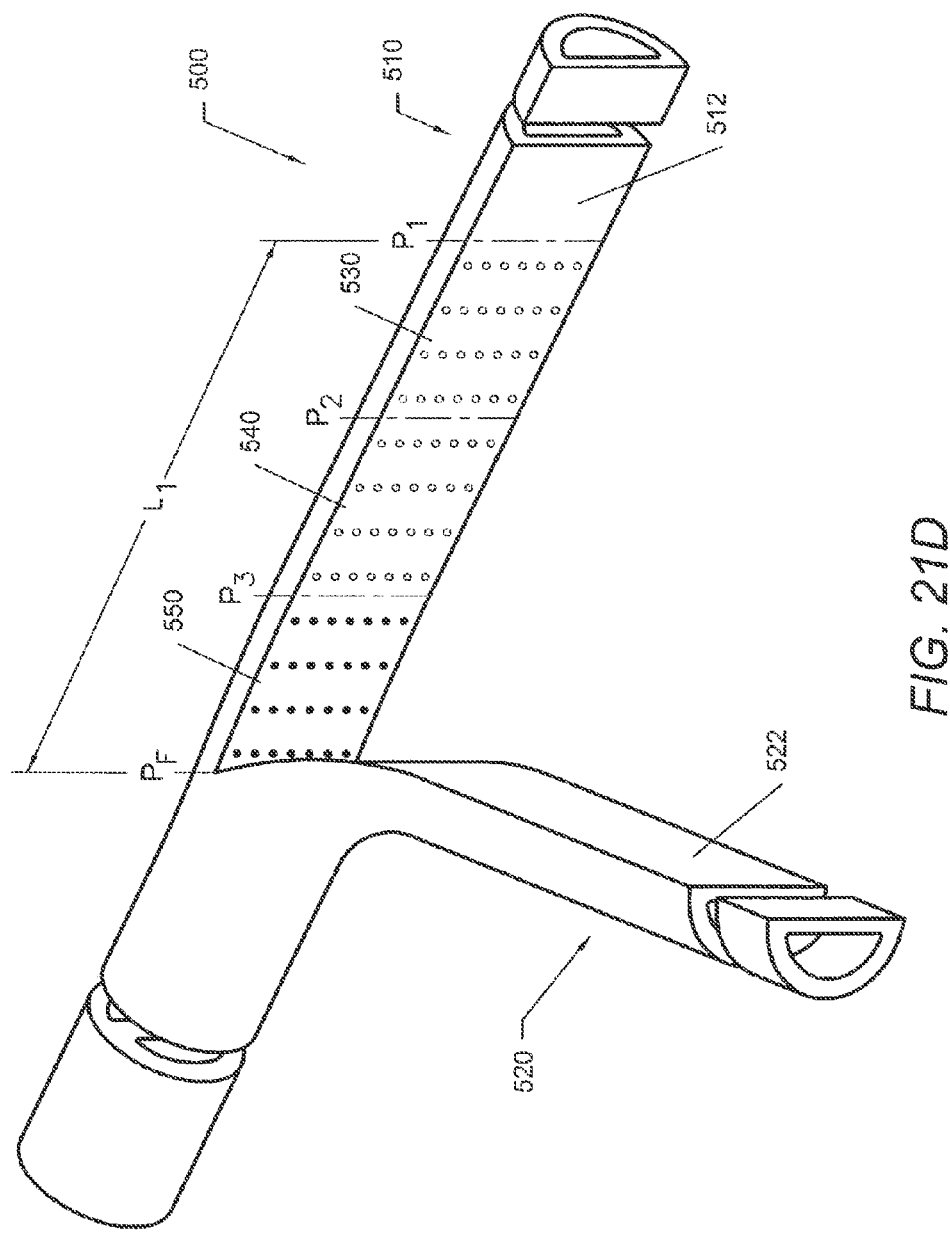
FIG. 21D is a representative view of a split-tip catheter, showing another embodiment of the present invention regarding varying separation force required to separate the tip sections.
Figure 21E:
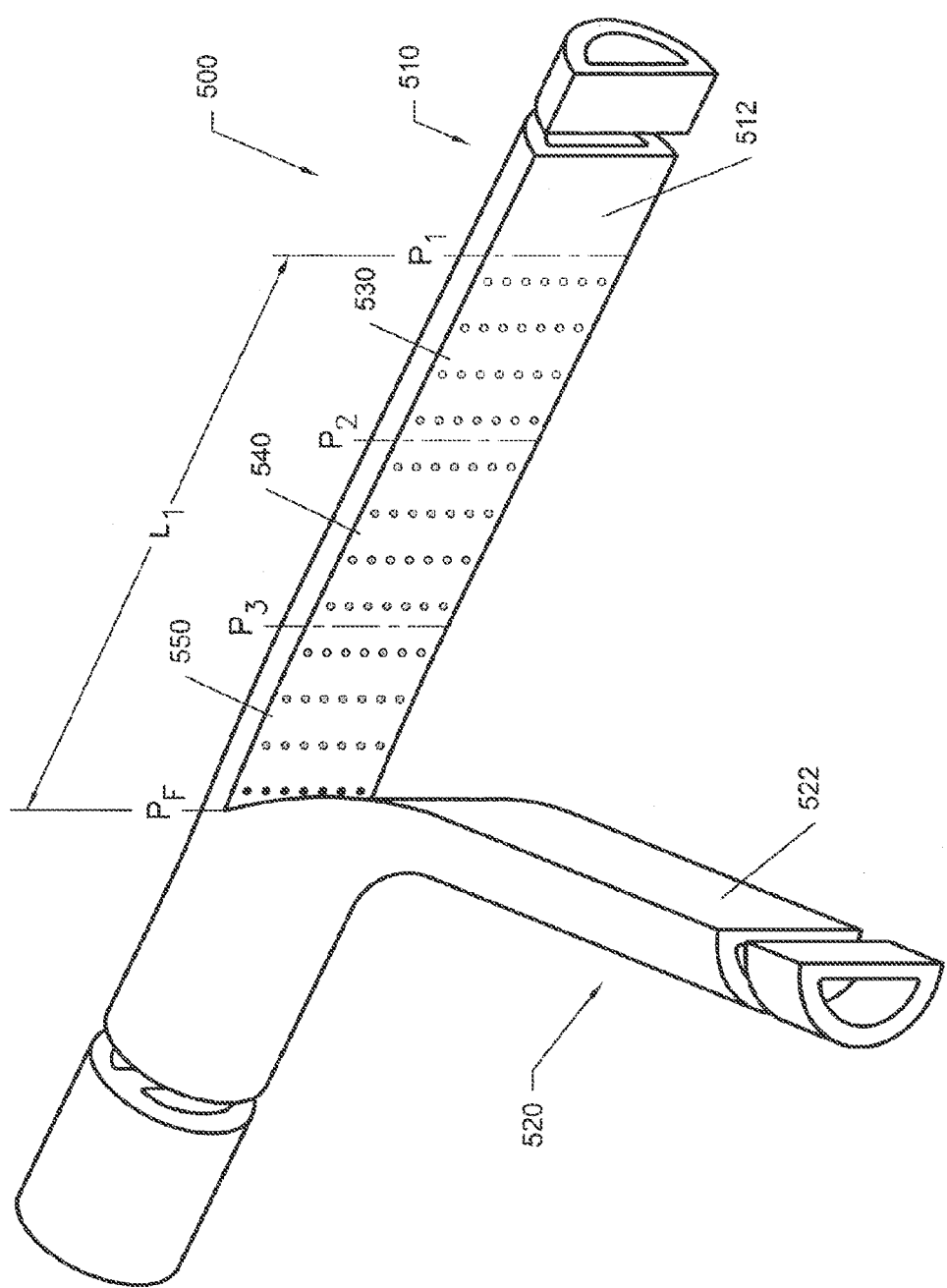
FIG. 21E is a representative view of a split-tip catheter, showing another embodiment of the present invention regarding varying separation force required to separate the tip sections.
Figure 21F:
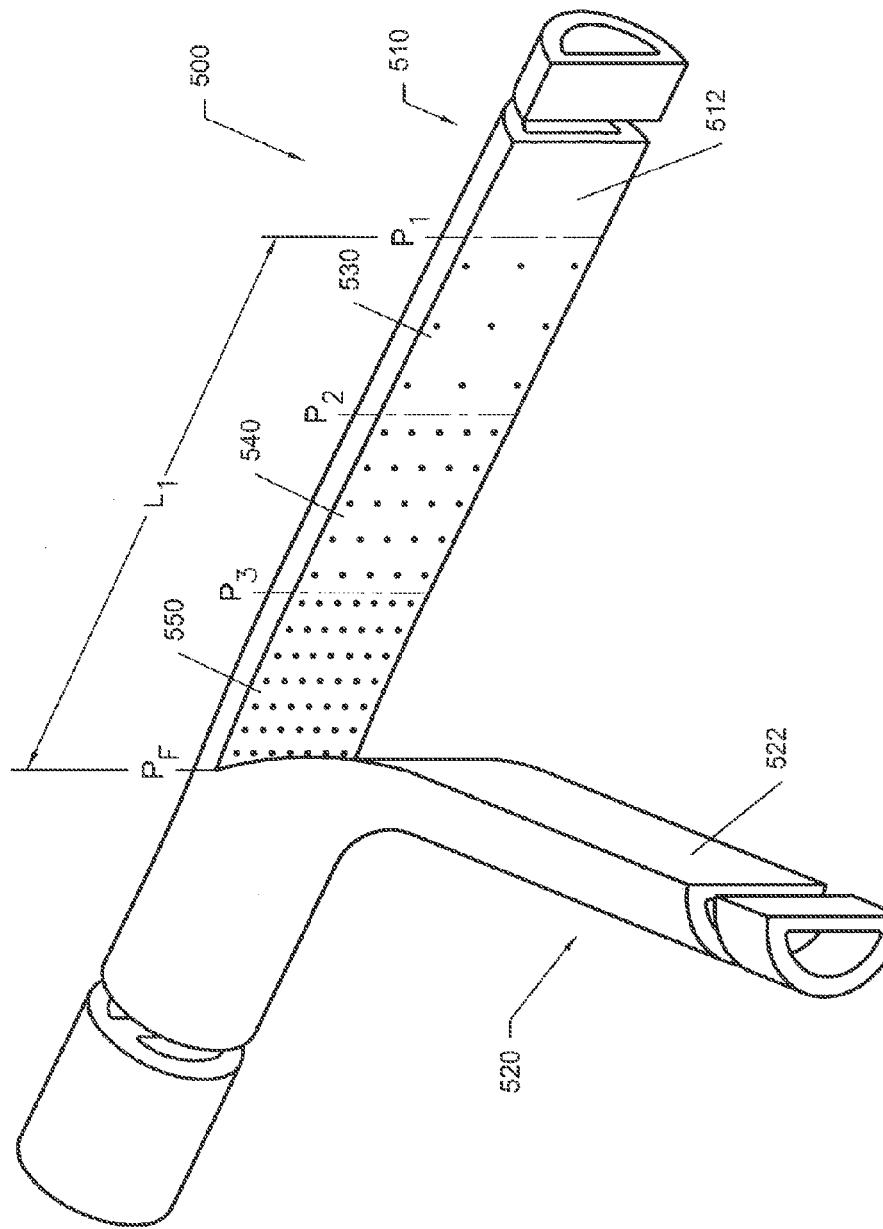
FIG. 21F is a representative view of a split-tip catheter, showing another embodiment of the present invention regarding varying separation force required to separate the tip sections.
Figure 21G:
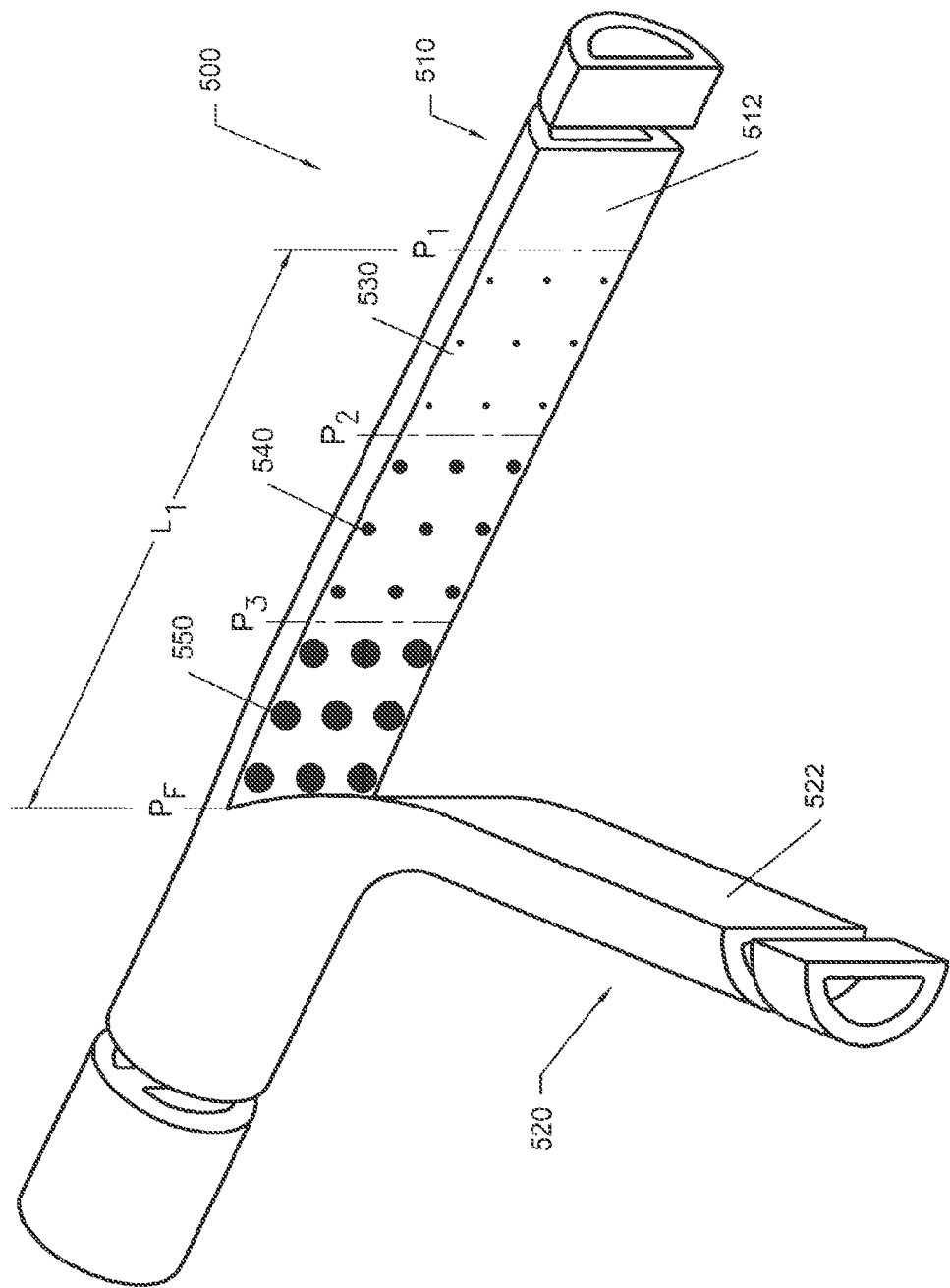
FIG. 21G is a representative view of a split-tip catheter, showing another embodiment of the present invention regarding varying separation force required to separate the tip sections.

FIG. 21D illustrates an embodiment of the present invention following the stepped configuration represented by FIG. 21B, wherein the number of fusion points within each fusion zone is uniform as is the bond strength of the fusion points within each fusion zone, but the bond strength of the fusion points is greater in each successive fusion zone as in FIG. 21C. FIG. 21E follows the continuous configuration represented by FIG. 21A, wherein the number of fusion points is uniform within each fusion zone, but the bond strength of the fusion zones is progressively increased as between fusion zones and within each fusion zone (i.e., the bond strength of the fusion points in the first fusion zone 530 are progressively increased as are those in the second fusion zone 540 and the third fusion zone 550). FIG. 21F follows a stepped configuration as the bond strength of the fusion points is the same in all fusion zones, but the number of fusion points is increased in each successive fusion zone (the number of fusion points is uniform within each zone). In FIG. 21G, the bond strength of the fusion points is the same in all fusion zones, as is the number of fusion points, but the size of the fusion points is increased in successive fusion points, creating a stepped configuration.

Figure 21H:
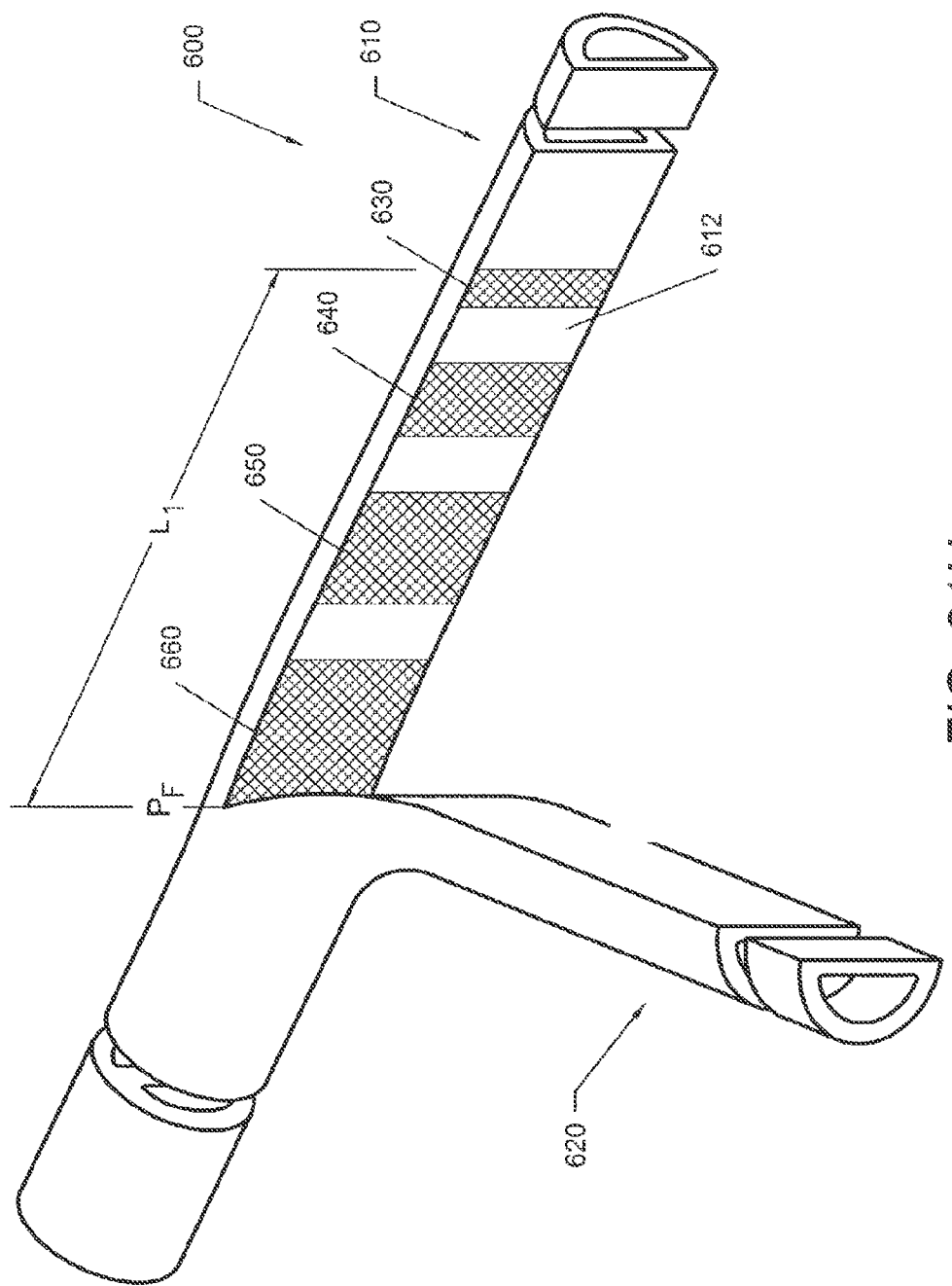
FIG. 21H is a representative view of a split-tip catheter, showing another embodiment of the present invention regarding varying separation force required to separate the tip sections.

Yet another embodiment of the present invention with respect to the establishment of an increasing separation force is illustrated in FIG. 21H, where the zones themselves increase in size. A catheter 600 is shown with tip sections 610 and 620, having four discrete and separate fusion zones, indicated by shading (the shading representing fusion points), on inner surface 612. A first zone 630 is smaller and therefore has less surface area for adhesion than a second zone 640, which in turn is smaller than a third zone 650, which in turn is smaller than a fourth zone 660. In this embodiment, there are free zones that do not have fusion points thereon, positioned in between each of the four stated zones. The first, second, third and fourth zones 630-660 can consist of fusion points as described above, in any combination thereof. Thus, for example, the first zone 630 could have a certain density of fusion points, while the second zone 640 could have a somewhat higher separation force created by a larger size of fusion points.

Figure 21I:
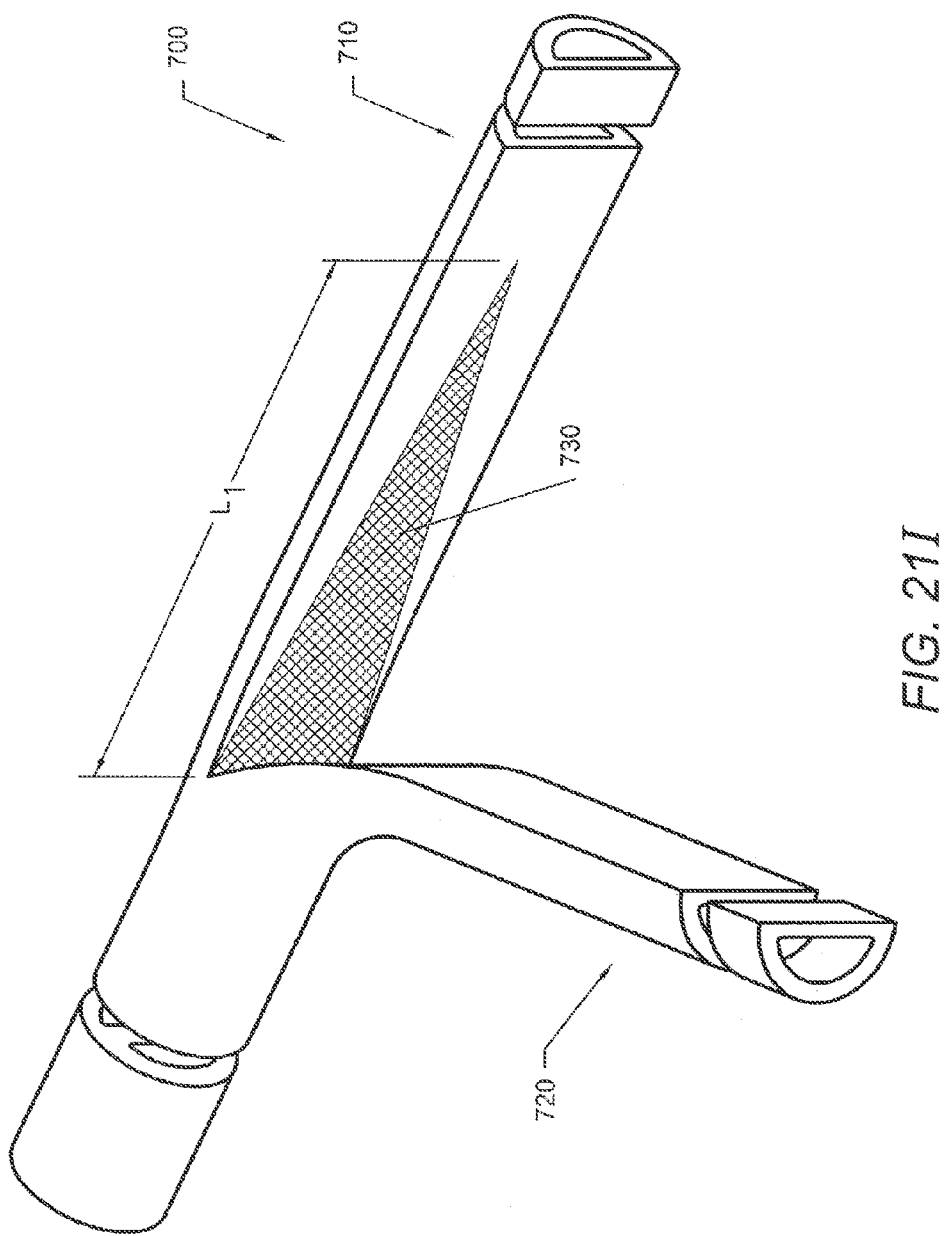
FIG. 21I is a representative view of a split-tip catheter, showing another embodiment of the present invention regarding varying separation force required to separate the tip sections.

A further embodiment of a catheter having a variable separation force is illustrated in FIG. 21I. In this figure, a catheter 700 is shown with tip sections 710 and 720, having a continuous fusion zone 730 that increases in size along $L_1$ from a distal end to a dividing point. Of course, one of skill in the art will appreciate the myriad of possibilities within the scope of the present invention with respect to the varying of fusion points and establishment of an increasing separation force in light of the embodiments illustrated herein.

Methods for producing the desired effects with respect to the establishment of an increasing separation force, as described above, include (but are not limited to) utilizing constant separation stress with a variable area and using a variable separation stress with a constant area. Realization of these embodiments can be accomplished through many different bonding techniques, a few of which are described below.

With respect to constant separation stress over a variable area, a first potential technique is the use of adhesive bonding in creating a varying pattern of adhesive to join the tip sections of a split-tip catheter. Types of adhesive which could be used include epoxy and cyanoacrylates, although certainly other comparable adhesives would also be suitable. This idea has been explored above, for example, with respect to varying the density of the fusion points and the size of the fusion points. A second technique is the use of solvent bonding in creating a varying pattern of solvent to join the tip sections of a split-tip catheter. Examples of the types of solvents that could be employed include Tecoflex® 1-MP (Thermedics), methyl ethyl ketone (MEK), cyclohexanon and alcohol, though certainly others could be used. A third technique is the use of thermal welding, in which heat can be used to join the tip sections of a split-tip catheter. A fourth technique is the use of RF energy to fuse the tip sections of a split-tip catheter. Finally, a fifth technique is the use of variable extrusion where surface area of a joining web could be increased between two lumens during the extrusion process.

In reference to variable separation stress over a constant area, the techniques above would be applicable in a different way. Specifically, in an adhesive bonding technique, the concentration of the adhesive could be varied to produce the variable bond strength. This idea has been explored above with respect to varying the type of adhesive used. In a solvent bonding technique, the solvent could be varied or the pressure utilized to join the tip sections could be varied. In a thermal welding technique, the temperature or dwell time could be varied. In an RF fusion technique, variable RF energy could be utilized. Finally, in a variable extrusion technique, pressure, temperature or dwell time could be varied during the extrusion process.

Figure 22B:
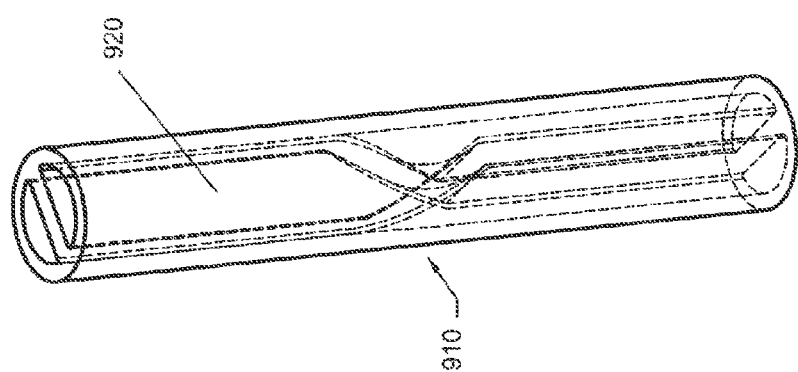
FIG. 22B is a representative view of a split-tip catheter, illustrating a twisted configuration according to another embodiment of the present invention.
Figure 22A:
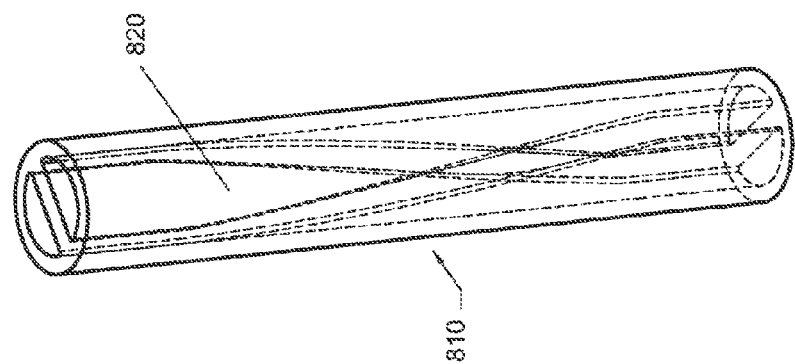
FIG. 22A is a representative view of a split-tip catheter, illustrating a twisted configuration according to one embodiment of the present invention.

Still another embodiment of the present invention with respect to the establishment of an increasing separation force is illustrated in FIGS. 22A and 22B, where the separation force is created by twisting the catheter upon formation thereof. FIG. 22A illustrates a gradual twist being applied to the catheter, while FIG. 22B illustrates a more abrupt twist over a shorter length. The twisting configuration imparts a variable separation force along the length of the catheter, increasing as measured from the distal end to the proximal end. For example, if a constant separation force is applied linearly to tip sections in a catheter having a 90° twisted septum, the force F a distance L away (i.e., the distal end of the catheter) would diminish to zero in the direction needed to continue the splitting, because F would be resolved in the tensile direction of the septum if the tube could not rotate. On the other hand, were the tube able to rotate, the force would not diminish to zero but would be reduced by the energy required to rotate the tube 90°.

The twisting action can be implemented in a number of ways, including employing a mandrel having a desired twist, which when inserted into a still warm tube, imparts the twist to the tube during cooling and utilizing a series of mandrels to force a previously straight tube into a desired twisted pattern, wherein heat is applied to reset the tubing configuration. Another technique would be to employ an extrusion die having a preset desired twist so that the twist is imparted to the catheter during formation thereof. Referring back to FIGS. 22A and 22B, the gradual twist 820 of the catheter 810 permits slow increase in resistance by transferring the splitting energy into rotational force if the catheter 810 is sufficiently flexible to twist when split. Differently, the abrupt twist 920 imparted to catheter 910 creates a tactile "positive stop," which notifies a user when a predetermined position along the length of the catheter 910 has been attained. Multiple twists could also be employed to provide a tactile measurement method for the user, and to provide an incremental separation force as described above in FIG. 21B.

Although improvements to the functioning and usability of a split-tip catheter have been presented separately herein, the improvements described above (for example, openings positioned near a dividing point of a split tip catheter, positioning of a guidewire aperture in a venous tip section, configuration of arterial and venous tip sections with respect to one another, friction reducing structures provided on a delivery sheath and/or a catheter, varying the separation force required to separate tip sections from one another, etc.) should not be considered exclusive and instead should be considered for use in conjunction with one another.

The present invention has been described above in terms of certain preferred embodiments so that an understanding of the present invention can be conveyed. However, there are many alternative arrangements for a multi-lumen catheter not specifically described herein but with which the present invention is applicable. Although specific features have been provided, the multi-lumen catheter of the present invention would equally be embodied by other configurations not specifically recited herein. The scope of the present invention should therefore not be limited by the embodiments illustrated, but rather it should be understood that the present invention has wide applicability with respect to catheter systems generally. All modifications, variations, or equivalent elements and implementations that are within the scope of the appended claims should therefore be considered within the scope of the invention.

What is claimed is:

1. A multi-lumen catheter, comprising:
    a generally cylindrical body enclosing a first and second lumen separated by a generally planar septum;
    a first tip section extending from a distal end of the body, the first tip section comprising:
        a generally planar surface extending from the septum;
        a distal end surface oblique to the generally planar surface; and
        an opening in the distal end surface; and
    a second tip section comprising:
        a proximal segment having a proximal cross-sectional area and a generally planar surface extending from the distal end of the body;
        a transition segment extending from the proximal segment; and
        a distal segment extending from the transition segment, the distal segment having a distal cross-sectional area greater than the proximal cross-sectional area.

2. The multi-lumen catheter according to claim 1, wherein the distal end surface of the first tip section includes rounded corners.

3. The multi-lumen catheter according to claim 1, wherein a distal end of the second tip section includes a beveled surface forming an angle in a range of about 25 degrees and about 75 degrees with a longitudinal axis of the second tip section.

4. The multi-lumen catheter according to claim 1, wherein the planar surface of the first tip section includes a first planar surface opening adjacent the distal end of the body.

5. The multi-lumen catheter according to claim 4, wherein the planar surface of the first tip section includes one or more planar surface openings distal to the first planar surface opening.

6. The multi-lumen catheter according to claim 1, wherein a medial portion of the body is curved.

* * * * *